United States Patent
Power et al.

(10) Patent No.: US 11,587,650 B2
(45) Date of Patent: Feb. 21, 2023

(54) TECHNIQUES FOR MANAGING ACCESS OF USER DEVICES TO THIRD-PARTY RESOURCES

(71) Applicant: Apple Inc., Cupertino, CA (US)

(72) Inventors: Todd D. Power, San Carlos, CA (US); Mark E. Pennell, Redwood City, CA (US); Jorge F. Pozas Trevino, San Mateo, CA (US); Sean R. Moore, Campbell, CA (US); Sami Shaio, New York, NY (US); Sangeeth Sridharan, San Jose, CA (US); Kevin M. Lynch, Woodside, CA (US)

(73) Assignee: Apple Inc., Cupertino, CA (US)

( * ) Notice: Subject to any disclaimer, the term of this patent is extended or adjusted under 35 U.S.C. 154(b) by 860 days.

(21) Appl. No.: 15/884,023

(22) Filed: Jan. 30, 2018

(65) Prior Publication Data
US 2019/0103173 A1     Apr. 4, 2019

Related U.S. Application Data

(60) Provisional application No. 62/566,014, filed on Sep. 29, 2017.

(51) Int. Cl.
*G16H 10/60* (2018.01)
*H04L 67/00* (2022.01)
(Continued)

(52) U.S. Cl.
CPC .............. *G16H 10/60* (2018.01); *H04L 67/12* (2013.01); *H04L 67/34* (2013.01); *H04L 67/53* (2022.05);
(Continued)

(58) Field of Classification Search
CPC ...... G16H 10/60; H04L 67/2838; H04L 67/34; H04L 67/12; H04L 67/20; H04L 67/325; H04L 67/02
See application file for complete search history.

(56) References Cited

U.S. PATENT DOCUMENTS 6,263,335 B1   7/2001  Paik et al.
6,714,936 B1   3/2004  Nevin, III
(Continued)

FOREIGN PATENT DOCUMENTS

CN   105760470 A   7/2016
CN   16845061 A1   6/2017
(Continued)

OTHER PUBLICATIONS

FHIR Release 3 Summary, HL7.org (https://web.archive.org/web/20171013061247/http://hl7.org/fhir) (Year: 2017).*
(Continued)

*Primary Examiner* — David R Lazaro
*Assistant Examiner* — Robert A Shaw
(74) *Attorney, Agent, or Firm* — Kilpatrick Townsend & Stockton

(57) ABSTRACT

Prior to connecting to a gateway associated with an electronic health record system, a user device can check in with a server. The server can send configuration information useable by the user device for connecting to the gateway for downloading medical record data. The configuration information may include an update value that is useable by the user device to determine a time frame for contacting the gateway. In some examples, the user device determines when to contact the gateway without using the update value.

19 Claims, 47 Drawing Sheets

(51) Int. Cl.
    *H04L 67/12*     (2022.01)
    *H04L 67/53*     (2022.01)
    *H04L 67/62*     (2022.01)
    *H04L 67/567*    (2022.01)
    *H04L 67/02*     (2022.01)

(52) U.S. Cl.
    CPC ............ *H04L 67/567* (2022.05); *H04L 67/62* (2022.05); *H04L 67/02* (2013.01)

(56) References Cited

U.S. PATENT DOCUMENTS

| | | |
|---|---|---|
| 6,957,218 B1 | 10/2005 | Wyatt |
| 7,908,552 B2 | 3/2011 | Heinze et al. |
| 8,229,881 B2 | 7/2012 | Pedro et al. |
| 8,428,964 B2 | 4/2013 | Picken |
| 8,429,179 B1 | 4/2013 | Mirhaji |
| 8,799,022 B1 | 8/2014 | O'Brien et al. |
| 8,843,505 B2 | 9/2014 | Campbell et al. |
| 8,850,057 B2 | 9/2014 | Natoli et al. |
| 8,984,006 B2 | 3/2015 | Wang et al. |
| 9,220,463 B2 | 12/2015 | Grubis |
| 9,911,290 B1 | 3/2018 | Zalewski et al. |
| 10,169,454 B2 | 1/2019 | Ait-Mikhtar et al. |
| 10,552,931 B2 | 2/2020 | Sheffer et al. |
| 10,553,308 B2 | 2/2020 | Baldwin |
| 10,628,553 B1 | 4/2020 | Murrish et al. |
| 2001/0054155 A1 | 12/2001 | Hagan et al. |
| 2002/0016719 A1 | 2/2002 | Nemeth et al. |
| 2003/0125017 A1 | 7/2003 | Greene et al. |
| 2004/0034550 A1 | 2/2004 | Menschik et al. |
| 2004/0243712 A1* | 12/2004 | Sakai ............ H04L 41/00 709/227 |
| 2005/0154708 A1 | 7/2005 | Sun |
| 2006/0080246 A1 | 4/2006 | Cook et al. |
| 2006/0100904 A1 | 5/2006 | Jee et al. |
| 2007/0005621 A1 | 1/2007 | Lesh et al. |
| 2007/0168231 A1 | 7/2007 | Sasai |
| 2007/0185732 A1 | 8/2007 | Hicks et al. |
| 2007/0192144 A1 | 8/2007 | Hauer et al. |
| 2008/0046292 A1 | 2/2008 | Myers et al. |
| 2008/0103916 A1 | 5/2008 | Camarador et al. |
| 2008/0147554 A1 | 6/2008 | Stevens et al. |
| 2008/0249386 A1 | 10/2008 | Besterman et al. |
| 2008/0256329 A1 | 10/2008 | Heinze et al. |
| 2009/0006061 A1 | 1/2009 | Thukral et al. |
| 2009/0063187 A1* | 3/2009 | Johnson ............ A61N 1/37282 705/2 |
| 2009/0070140 A1 | 3/2009 | Morsch et al. |
| 2009/0073991 A1* | 3/2009 | Landrum ............ A61B 5/4869 370/400 |
| 2009/0080408 A1 | 3/2009 | Natoli et al. |
| 2009/0106225 A1 | 4/2009 | Smith et al. |
| 2009/0216562 A1 | 8/2009 | Falulner et al. |
| 2009/0276396 A1 | 11/2009 | Gorman et al. |
| 2009/0287837 A1 | 11/2009 | Felsher |
| 2009/0326982 A1* | 12/2009 | Deobhakta ............ G16H 10/60 705/3 |
| 2010/0131900 A1 | 5/2010 | Spetalnick |
| 2010/0268552 A1 | 10/2010 | Schoenberg et al. |
| 2011/0029592 A1 | 2/2011 | Downey et al. |
| 2012/0130734 A1 | 5/2012 | White |
| 2012/0253847 A1 | 10/2012 | Dell'Anno et al. |
| 2013/0054968 A1 | 2/2013 | Gupta |
| 2013/0066886 A1 | 3/2013 | Bagchi et al. |
| 2013/0132109 A1* | 5/2013 | Mruthyunjaya ....... G06Q 10/06 705/2 |
| 2013/0138457 A1 | 5/2013 | Ragusa |
| 2013/0144790 A1 | 6/2013 | Clements |
| 2013/0191513 A1* | 7/2013 | Kamen ................ H04L 67/02 709/219 |
| 2013/0238349 A1 | 9/2013 | Sethumadhavan et al. |
| 2013/0275153 A1 | 10/2013 | Dastmalchi et al. |
| 2013/0346108 A1* | 12/2013 | Kamen ................ G16H 40/67 705/2 |
| 2014/0081669 A1* | 3/2014 | Raduchel ................ G16Z 99/00 705/3 |
| 2014/0095201 A1 | 4/2014 | Farooq et al. |
| 2014/0136237 A1 | 5/2014 | Anderson et al. |
| 2014/0171117 A1 | 6/2014 | LaMarca et al. |
| 2014/0180711 A1* | 6/2014 | Kamen ................ G16H 70/40 705/2 |
| 2014/0188516 A1 | 7/2014 | Kamen et al. |
| 2014/0207518 A1 | 7/2014 | Kannan et al. |
| 2014/0278448 A1 | 9/2014 | Sadeghi et al. |
| 2014/0365210 A1 | 12/2014 | Riskin et al. |
| 2014/0365241 A1 | 12/2014 | Dillie et al. |
| 2015/0025906 A1* | 1/2015 | Wen ................ G16H 40/67 705/2 |
| 2015/0073943 A1 | 3/2015 | Norris et al. |
| 2015/0081332 A1 | 3/2015 | Casper et al. |
| 2015/0154364 A1* | 6/2015 | Biasi .................... A61B 5/0022 709/223 |
| 2015/0186504 A1 | 7/2015 | Gorman et al. |
| 2015/0356248 A1 | 12/2015 | Kogan et al. |
| 2015/0356252 A1 | 12/2015 | Beker |
| 2015/0382263 A1 | 12/2015 | Jain et al. |
| 2016/0019299 A1 | 1/2016 | Boloor et al. |
| 2016/0034713 A1 | 2/2016 | Ramirez |
| 2016/0098389 A1 | 4/2016 | Bruno et al. |
| 2016/0132648 A1 | 5/2016 | Shah et al. |
| 2016/0147954 A1 | 5/2016 | Ng Tari et al. |
| 2016/0147971 A1 | 5/2016 | Kolowitz et al. |
| 2016/0170814 A1 | 6/2016 | Li et al. |
| 2016/0224542 A1 | 8/2016 | Bulgakov et al. |
| 2016/0232242 A1 | 8/2016 | Friscia, III et al. |
| 2016/0300019 A1 | 10/2016 | Baluta |
| 2016/0371446 A1 | 12/2016 | Otin |
| 2017/0068785 A1* | 3/2017 | Experton ............... H04W 12/02 |
| 2017/0103163 A1 | 4/2017 | Emanuel et al. |
| 2017/0132372 A1 | 5/2017 | Sharifi Sedeh et al. |
| 2017/0150939 A1 | 6/2017 | Shah |
| 2017/0161439 A1* | 6/2017 | Raduchel ............... H04W 12/06 |
| 2017/0235885 A1 | 8/2017 | Cox |
| 2017/0286381 A1 | 10/2017 | Fink et al. |
| 2017/0286610 A9 | 10/2017 | Harris et al. |
| 2018/0046679 A1 | 2/2018 | Sharifi Sedeh et al. |
| 2018/0089370 A1 | 3/2018 | Yu |
| 2018/0211058 A1* | 7/2018 | Aunger ................. H04L 63/102 |
| 2018/0226143 A1 | 8/2018 | Khashman |
| 2019/0069155 A1 | 2/2019 | Katayama et al. |
| 2019/0206524 A1 | 7/2019 | Baldwin et al. |

FOREIGN PATENT DOCUMENTS

| | | | |
|---|---|---|---|
| CN | 107992511 A | 5/2018 | |
| EP | 1 126 681 A1 | 8/2001 | |
| EP | 1126681 A2 * | 8/2001 | ........... G06F 40/151 |
| WO | 2007/084502 A1 | 7/2007 | |
| WO | 2014/036362 A1 | 3/2014 | |
| WO | 2016/126868 A1 | 11/2016 | |

OTHER PUBLICATIONS

Peterson et al, A Blockchain-Based Approach to Health Information Exchange Networks (Year: 2017).*
International Search Report and Written Opinion dated Nov. 15, 2018 in International Application No. PCT/US2018/045917. 16 pages.
Lodderstedt, et al., "OAuth 2.0 Threat Model and Security Considerations," Internet Engineering Task Force (IETF), Request for Comments: 6819, Category Informational, ISSN: 2070-1721. Jan. 2013. 72 pages.
AdWords API and Google Ads API Forum, "Changing the OAuth2 Client Secret." May 15, 2014 first response in forum, downloaded Jan. 16, 2019. 2 pages.
Katehakis et al., "An Environment for the Creation of an Integrated Electronic Health Record in Hygeianet, The Regional Health Telematics Network of Crete." Proceedings of the 16th Annual Towards an Electronic Patient Record Conference and Exhibition (TEPR 2000), Your Connection to Electronic Healthcare, San Francisco, California, May 9-11, 2000. vol. 1. pp. 89-98.

(56) References Cited

OTHER PUBLICATIONS

Smarty, "How to Get Rid of Unwanted Redirects in Google Search Results." Oct. 11, 2010. 5 pages.
Thompson, Clive, "How to Baffle Web Trackers By Obfuscating Your Movements Online." Gear, Nov. 21, 2015. 7 pages.
"Final Office Action," dated Jul. 19, 2021 in U.S. Appl. No. 15/849,310. 14 pages.
"Notification of Second Office Action," dated Aug. 3, 2021 in Chinese Patent Application No. 201880056130.3. 7 pages (includes English translation).
U.S. Appl. No. 15/884,115 , Non-Final Office Action, dated Jan. 28, 2022, 47 pages.
U.S. Appl. No. 16/019,497 , Advisory Action, dated Mar. 15, 2022, 8 pages.
U.S. Appl. No. 17/001,128, Non Final Office Action, dated Sep. 9, 2022, 10 pages.
U.S. Appl. No. 15/884,115, Final Office Action, dated Aug. 5, 2022, 44 pages.
U.S. Appl. No. 15/849,310, Final Office Action, dated Jun. 8, 2022, 17 pages.
John Hopkins Medical Campus Map (Feb. 2012) (Year: 2012). 1 page.
U.S. Appl. No. 16/019,497, Non-Final Office Action, dated Jun. 28, 2022, 63 pages.

\* cited by examiner

FIG. 5

About Yourself

Personal Details

Full Name: Johnny Appleseed
WORK TITLE: IT Admin Mgr
Work Email: Jca@health.org
WORK PHONE: Required
PERSONAL LINKEDIN PROFILE: Optional Your Progress
- Introduction
- About Yourself
- Business Type
- Business Information
- Head Office Location
- Verify Map Location
- Web Links
- Primary Contacts Sign out | Next

FIG. 6

Your Business

Business Type

Which best describes your business?
- Small Business — Less than 50 employees or located in a single city
- Regional or National Brand/Chain — Less than 50 employees or located in multiple cities within a country
- Multinational Brand/Chain — More than 1000 employees or carrying on business in multiple countries
- Customer Service Platform — Providers of help desk software and related customer support services to 3rd party businesses
- Multinational Brand/Chain — More than 1000 employees or carrying on business in multiple countries
- Customer Service Platform — Providers of help desk software and related customer support services to 3rd party businesses
- ● Healthcare Provider — Hospitals, clinics, or medical professionals that provide patient care
- Other — Businesses that are not accurately described above Your Progress
- Introduction
- About Yourself
- Business Type
- Business Information
- Head Office Location
- Verify Map Location
- Web Links
- Primary Contacts Sign out | Next ns, which claim the benefit of and priority to U.S. Provisional Patent Application No. 62/565,847, filed Sep. 29, 2017, entitled "Normalization of Medical Terms" and is related to co-pending U.S. patent application Ser. No. 15/884,115, filed Jan. 30, 2018, entitled "Techniques for Building Medical Provider Databases," which claims the benefit of and priority to U.S. Provisional Patent Application No. 62/566,104, filed Sep. 29, 2017, entitled, "Techniques for Building Medical Provider Databases."

TECHNIQUES FOR MANAGING ACCESS OF USER DEVICES TO THIRD-PARTY RESOURCES

CROSS-REFERENCE TO RELATED APPLICATION(S)

This application claims the benefit of and priority to U.S. Provisional Application No. 62/566,014, filed Sep. 29, 2017, entitled "Techniques for Managing Access of User Devices to Third-Party Resources." The disclosure of this application is incorporated by reference herein in its entirety.

This application is related to co-pending U.S. patent application Ser. No. 15/849,310, filed Dec. 20, 2017, entitled "On-Device Searching Using Medical Term Expressions," which claims the benefit of and priority to U.S. Provisional Patent Application No. 62/565,956, filed Sep. 29, 2017, entitled "On-Device Searching Using Medical Term Expressions" and is related to co-pending U.S. patent application Ser. No. 15/947,478, filed Apr. 6, 2018, entitled "Techniques for Anonymized Searching of Medical Providers," which claims the benefit of and priority to U.S. Provisional Patent Application No. 62/566,051, filed Sep. 29, 2017, entitled"Techniques for Anonymized Searching of Medical Providers" and is related to co-pending U.S. patent application Ser. No. 16/019,497, filed Jun. 26, 2018, entitled "Normalization of Medical Terms," and U.S. patent application No.: filed entitled "Index-Based Deidentification," both which claim the benefit of and priority to U.S. Provisional Patent Application No. 62/565,847, filed Sep. 29, 2017, entitled "Normalization of Medical Terms" and is related to co-pending U.S. patent application Ser. No. 15/884,115, filed Jan. 30, 2018, entitled "Techniques for Building Medical Provider Databases," which claims the benefit of and priority to U.S. Provisional Patent Application No. 62/566,104, filed Sep. 29, 2017, entitled, "Techniques for Building Medical Provider Databases."

BACKGROUND

Users typically visit more than one health institution to obtain medical treatment. For example, a user may periodically visit a neighborhood clinic for annual physical evaluations and for minor medical procedures. An electronic health record (EHR) is a computer-stored and transferrable copy of a user's physical health record. The neighborhood clinic may maintain an instance of the user's electronic health record (e.g., using an EHR system, sometimes referred to as an electronic medical record (EMR) system). When the user visits, a medical professional may update the electronic health record. However, different instances of the user's electronic health record may be maintained by other health institutions that are unaffiliated with the neighborhood clinic. For example, the user may have visited a surgical center for a surgery, been transported to an emergency room in connection with an accident, or may have visited a different clinic while on vacation in a different city. Each of the surgical center, the emergency room, and the different clinic, may have created an instance of the user's electronic health record, which may be maintained using different EHR systems. The EHR systems may provide patient portals for accessing health records on their systems. Because these portals are built and maintained by different organizations, accessing each by the user may require a unique set of user credentials. And once the user logs in to a particular portal, she is still limited by what portion of her electronic health record will be available for viewing. Existing computer systems may be able to maintain a single connection to a single EHR system, but challenges may arise when these systems attempt to programmatically maintain multiple connections across multiple EHR systems. Moreover, because different medical professionals contribute to the instances of the electronic health record, data inconsistencies may exist between electronic health records sourced from different EHR systems. Conventional data rectification techniques may prove insufficient to resolve these types of data inconsistences.

BRIEF SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a user device, including: a memory configured to store computer-executable instructions, and a processor in communication with the memory and configured to execute the computer-executable instructions to at least send an information request to a server, the information request requesting information about accessing a gateway of an electronic health record system. The processor is also configured to receive, from the server, a communication including an update value and a data object associated with the gateway, the update value representing a time period and being generated based at least in part on characteristics of the electronic health record system, and the data object including configuration information useable by the user device for accessing the gateway. The processor is also configured to determine a random clock value that is between zero and the update value, the random clock value corresponding to a clock time within the time period. The processor is also configured to send an access request to the gateway at the clock time based at least in part on the configuration information, the access request to request downloading of medical record data maintained by the electronic health record system. Other examples of this aspect include corresponding computer systems, apparatus, and computer programs recorded on one or more computer storage devices, each configured to perform the actions of the methods.

Implementations may include one or more of the following features. The user device where the configuration information includes application programming interface (API) information that is particular to the gateway. The user device where the processor is further configured to send an additional information request to the server in preparation for sending an additional access request to the gateway. The processor is further configured to receive an additional communication from the server, the additional communication including a status indicator for the gateway. The processor is further configured to refrain from sending the additional access request when the status indicator indicates that the gateway is unavailable. The user device where the medical record data is downloaded according to fast healthcare interoperability resources (FHIR) standard. The user device where the data object further includes a universal user identifier for the gateway. Implementations of the described techniques may include hardware, a method or process, or computer software on a computer-accessible medium.

One general aspect includes a computer-implemented method, including: sending, by a user device, an information request to a server, the information request requesting information about accessing a gateway of an electronic health record system. The computer-implemented method also includes receiving, from the server, a communication including a data object associated with the gateway, the data object including configuration information useable by the user device for accessing the gateway. The computer-implemented method also includes sending, by the user device, a first access request to the gateway based at least in part on the configuration information, the first access request to request downloading of medical record data maintained by the electronic health record system. The computer-implemented method also includes when the first access request fails, determining a future time to send a second access request to the gateway; sending, by the user device and at the future time, the second access request to the gateway; and receiving a data package from the gateway based at least in part on the second access request, the data package including medical record data. Other examples of this aspect include corresponding computer systems, apparatus, and computer programs recorded on one or more computer storage devices, each configured to perform the actions of the methods.

Implementations may include one or more of the following features. The computer-implemented method where the configuration information includes application programming interface (API) information that is particular to the gateway. The computer-implemented method where determining the future time is based at least in part on characteristics of the user device. The computer-implemented method where the characteristics of the user device include at least one of locked state, battery life, network connectivity, available processing capabilities, or available storage. The computer-implemented method where determining the future time is based at least in part on a predefined routine defined in the user device, the predefined routine useable by the user device for contacting remote resources. The computer-implemented method where the medical record data includes an electronic health record associated with a user of the user device. The computer-implemented method where the information request includes information identifying a medical provider associated with the electronic health record system and a plurality of other providers associated with at least one of the electronic health record system or a different electronic health record system. The computer-implemented method further including: sending an additional information request to the server in preparation for sending an additional access request to the gateway. The computer-implemented method may also include receive an additional communication from the server, the additional communication including a status indicator for the gateway. The computer-implemented method may also include refrain from sending the additional access request when the status indicator indicates that the gateway is unavailable. The computer-implemented method where the gateway and the server are operated by distinct entities. The computer-implemented method further including determining that the first access request has failed based at least in part on receiving a connection timeout error. Implementations of the described techniques may include hardware, a method or process, or computer software on a computer-accessible medium.

One general aspect includes a system, including: a memory configured to store computer-executable instructions and a processor in communication with the memory and configured to execute the computer-executable instructions to at least simulate, during a first period, user connections to a plurality of gateways associated with a plurality of electronic health record systems configured to maintain electronic health records for a plurality of users. The processor is also configured to perform one of a plurality of actions based at least in part on a simulation condition of a first user connection to a first gateway of the plurality of gateways, the simulation condition identified while simulating the user connections to the plurality of gateways, the plurality of actions including: a first action including simulating a second user connection to the first gateway during a second period, determining that the first gateway is inactive based at least in part on the second user connection failing during the second period, and notifying a set of user devices that the first gateway is inactive. The plurality of actions also include a second action including notifying the set of user devices that the first gateway is inactive without simulating the second user connection. The plurality of actions also include a third action including enabling the set of user devices to connect to the first gateway. Other examples of this aspect include corresponding computer systems, apparatus, and computer programs recorded on one or more computer storage devices, each configured to perform the actions of the methods.

Implementations may include one or more of the following features. The system the third action includes enabling the set of user devices to connect to the first gateway in accordance with an update value, the update value defining a future time window in which the set of user devices randomly connect to the first gateway. The system where the simulation condition includes at least one of a partial failure condition, a complete failure condition, or a success condition. The system where the first action is performed when the simulation condition is the partial failure condition, the second action is performed when the simulation condition is the complete failure condition, and the third action is performed when the simulation condition is the success condition. The system where simulating the user connections to the plurality of gateways includes using test user credentials to connect to test user profiles maintained by the plurality of electronic health record systems. Implementations of the described techniques may include hardware, a method or process, or computer software on a computer-accessible medium.

BRIEF DESCRIPTION OF THE DRAWINGS

FIGS. 5-17 illustrate example views of a user interface for onboarding provider entities on to a system that enables sharing of electronic health records between user devices and gateways of electronic health record system, according to at least one example.

DETAILED DESCRIPTION

Figure 1:
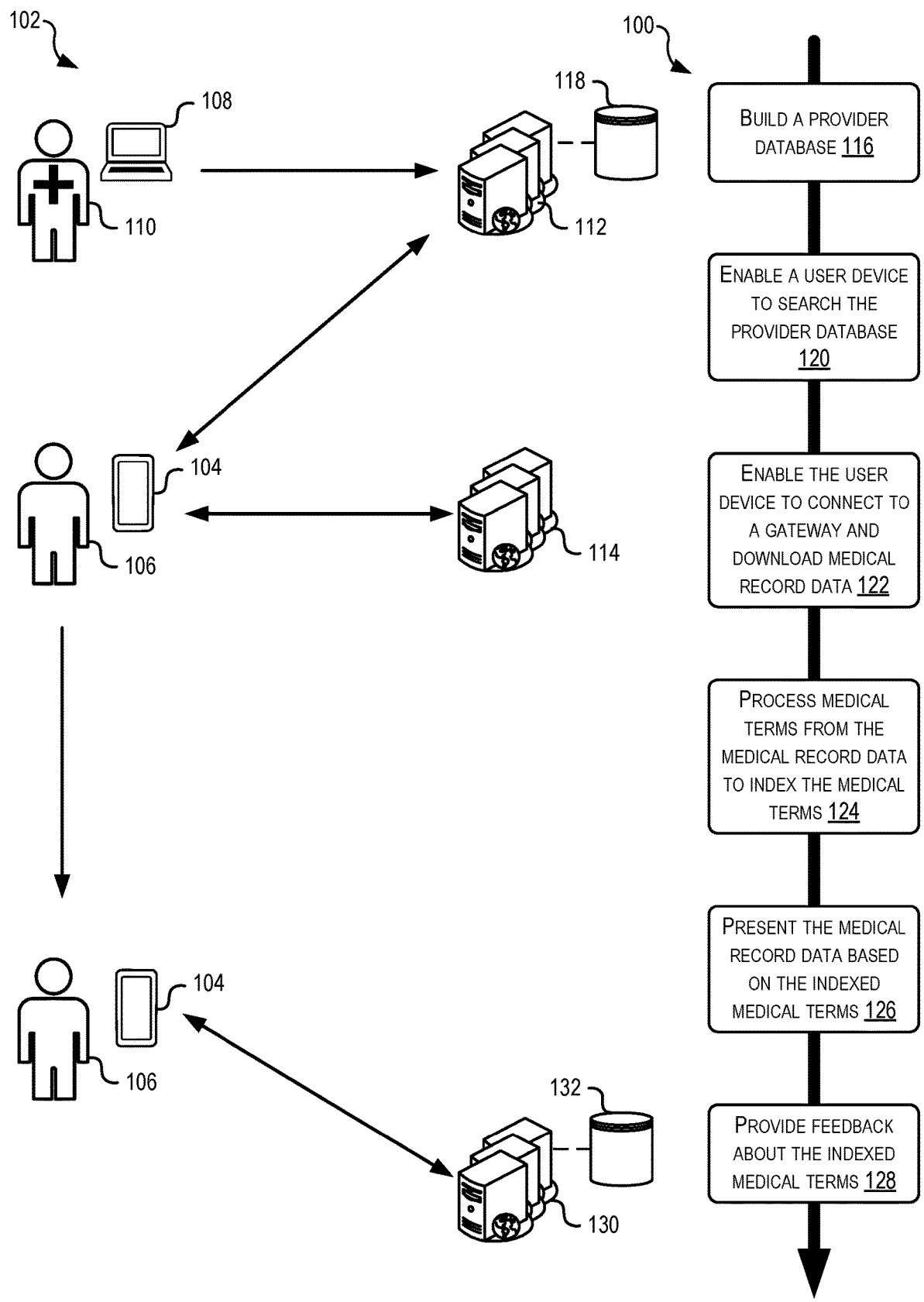
FIG. 1 illustrates a block diagram and a flowchart for enabling storage and retrieval of electronic health records on user devices, according to at least one example.

In the following description, various examples will be described. For purposes of explanation, specific configurations and details are set forth in order to provide a thorough understanding of the examples. However, it will also be apparent to one skilled in the art that the examples may be practiced without the specific details. Furthermore, well-known features may be omitted or simplified in order not to obscure the example being described.

Examples of the present disclosure are directed to, among other things, methods, systems, devices, and computer-readable media for obtaining electronic health records from various disparate sources, processing the electronic health records to enable efficient storage and retrieval, and presenting medical information from the electronic health records in a uniform manner using a health application of a user device. Users to whom the electronic health records belong typically visit different medical providers as part of obtaining treatment. These medical providers may be part of the same provider organization (e.g., a clinic and a hospital owned by the same entity) or may be part of different organizations (e.g., a dialysis clinic owned by a first entity and an imaging center owned by a second entity). Each of these medical providers may maintain a portion of a particular user's electronic health record using EHR systems.

Some medical providers may provide web portals (e.g., patient portals) that allow users to view and/or otherwise interact with their respective electronic health records. However, because the medical industry is made up of many different organizations and because users tend to obtain care from different organizations, it is very unlikely that a single web portal will have a complete electronic health record for every user. Instead, users may have to access multiple web portals; however, some medical providers may not even offer web portal capabilities. Because of this, users face challenges as they try to view a complete picture of their medical history.

The EHR systems that hosts the web portals may be configured differently from one another. For example, data storage formats, user and administrator functionality, and coding schemas may be unique to each. A system described herein enables individual, ongoing data pipelines to be established with each of these disparate sources. Once a pipeline is connected, the system described provides a platform for normalizing the data storage formats, user and administrator functionality, and coding schemas from these disparate sources. Thus, once each pipeline has been connected, the data may be stored on a user device in a uniform format, with a predefined set of user functionality, and according to a single coding schema. Doing so results in not only a technical improvement to a computing device, but does so in a way that stores data from the disparate sources in an optimized manner. The data is optimized as to storage capacity and storage access. Because of this, the computing device operates more efficiently than other devices that access electronic health records. This effectively frees up other computing resources for performing other processes.

The system described herein allows users to search for relevant medical providers and download, to their smartphones or other user devices, their respective electronic health records from the medical providers. In some examples, this connection may represent a data pipeline connection with the medical provider. A provider subscription system operates as an intermediary between user devices and gateways of the EHR systems. The gateways are effectively outlets or endpoints provided by the EHR systems. These endpoints are accessible for downloading data from the EHR systems.

Generally, the provider subscription system provides a process for onboarding new medical providers to the system. This includes storing provider information in a database that is searchable by the user devices. The provider information can include, for example, location information about the medical providers and configuration information for one or more gateways associated with the medical providers. The users can use their user devices to search the database to find their medical providers. To maintain user privacy, this searching is performed in a way that obfuscates, to the provider subscription systems, relationships between medical providers and searching users. Once medical providers have been identified by searching, the user devices receive provider information associated with the identified medical providers. The user devices use this provider information to establish connections with gateways associated with the identified medical providers. The gateways share electronic health records with the user devices using an industry standard format such as Fast Healthcare Interoperability Resource (FHIR) created by the Health Level Seven (HL7) International standards organization. Techniques described herein also manage the frequency at which the user devices connect to the gateways initially and in the future to check for updates to the electronic health records registered at the EHR systems.

Once the electronic health records have been downloaded to the user devices, they are stored using a first data model. The electronic health records are also processed using an indexing algorithm to index each medical term (e.g., a text string including one or more words) as a medical term expression (e.g., an index including one or more expression primitives). The medical term expressions which may be serialized, computational forms of the medical term are stored on the user device using a second data model. Information associating the medical terms and the medical term expressions is also saved on the user device. The medical term expression is useable to present, organize, search, and/or augment health record information from the electronic health records. This may be desirable to normalize medical entries in the electronic health records that have been entered by many different medical professionals. These medical professionals may use different formats, abbreviations, orders, words, synonyms, and other changes to describe the same thing. For example, a first doctor may write a prescription as "Tylenol 500 mg daily oral" and a second doctor may write the same prescription as "500 MG acetaminophen oral taken daily." Medically, these two prescriptions may be identical. However, conventional indexing systems may be unable to recognize this similarity. Using the medical term expressions described herein, these two prescriptions, which may be present in a user's electronic health record, can be represented in a uniform way (e.g., "Tylenol 500 MG oral daily"). In this manner, similar record entries in the electronic health record can be grouped together, identified during a search, and otherwise used for comparison.

With respect to using medical term expressions for grouping, all instances of "Tylenol" or "Tylenol 500 MG" across many different instances of the electronic health record may be grouped together and presented in a user interface. Using conventional techniques, it may only be possible to see those instances found in the relevant instance of the electronic health record. In this example, the user may be provided a richer and more complete picture of her medical history. This may prove useful for the user and/or medical professionals when making decisions about future care for the user.

With respect to using medical term expressions for searching, the user may search her medical history (e.g., a collection instances of her electronic health records) for information about her heart. To perform this search, the keyword heart may be converted to a medical term expression and used to search a database that includes the other medical term expressions from the electronic health record. Identified results may be presented in any suitable manner. The results may include instances in the electronic health record where the user's heart was mentioned (e.g., a timeline of medical events relating to the user's heart).

Contextual information in the form of metadata can be also associated with the medical term expressions. This contextual information can be used to enhance the underlying medical terms. For example, continuing with the prescriptions discussed above, ingredients, images of pills, usage instructions, and the like (e.g., types of metadata) can be associated with the medical term expressions and presented when "Tylenol 500 MG oral daily" is presented to the user.

Turning now to the figures, FIG. 1 illustrates a block diagram 102 and a flowchart showing a process 100 for enabling storage and retrieval of electronic health records on user devices, according to at least one example. The diagram 102 includes user device 104, which can be any suitable electronic user device capable of communicating with other electronic devices over a network such as the Internet. In some examples, the user device 104 can be a smartphone or other user device on which specialized applications can operate. The user device 104 is associated with or otherwise operated by a user 106. The user 106 is an example of a patient whose electronic health records are the subject of this specification.

The diagram 102 also includes provider user device 108. The provider user device 108 can be any suitable electronic user device capable of communicating with other electronic devices over a network such as the Internet. In some examples, the provider user device 108 can be a laptop, personal computer, or other user device on which a provider user 110 may interact. The provider user 110 is an example of a representative of a medical provider who uses the provider user device 108 to interact with a provider subscription system 112. Medical information associated with the medical provider (e.g., electronic health records of patients of the medical provider) is stored at an EHR system 114. The EHR system 114 may be associated with one or more medical providers (e.g., organization entities, brand entities, and/or location entities). In particular, the EHR system 114 may store, organize, and/or otherwise manage health record data generated by medical professionals of the medical providers. The EHR system 114 may include one or more gateways, each including one or more endpoints to enable multiple connections between the EHR system 114 and other electronic devices. In some examples, user devices such as the user device 104 may interact with the EHR system 114 using any suitable interfaces such as gateway application programming interfaces (API). The gateway APIs may define a set of function calls for communications between the EHR system 114 and the user device 104.

FIGS. 1, 3, 18, 19, 20, 35, 36, 38, 39, 40, 41, 43, 44, 45, 46, 47, 48, 50, and 51 illustrate example flow diagrams showing processes 100, 300, 1800, 1900, 2000, 3500, 3600, 3800, 3900, 4000, 4100, 4300 (shown on FIGS. 43 and 44), 4500, 4600, 4700, 4800, 5000, and 5100, according to at least a few examples. These processes, and any other processes described herein, are illustrated as logical flow diagrams, each operation of which represents a sequence of operations that can be implemented in hardware, computer instructions, or a combination thereof. In the context of computer instructions, the operations may represent computer-executable instructions stored on one or more non-transitory computer-readable storage media that, when executed by one or more processors, perform the recited operations. Generally, computer-executable instructions include routines, programs, objects, components, data structures and the like that perform particular functions or implement particular data types. The order in which the operations are described is not intended to be construed as a limitation, and any number of the described operations can be combined in any order and/or in parallel to implement the processes.

Additionally, some, any, or all of the processes described herein may be performed under the control of one or more computer systems configured with specific executable instructions and may be implemented as code (e.g., executable instructions, one or more computer programs, or one or more applications) executing collectively on one or more processors, by hardware, or combinations thereof. As noted above, the code may be stored on a non-transitory computer-readable storage medium, for example, in the form of a computer program including a plurality of instructions executable by one or more processors.

The process 100 may begin at 116 by building a provider database 118. This may be performed by the provider subscription system 112 based on information received from the provider user devices 108. For example, the provider users 110 may use the provider user devices 108 to share information about the about provider entities with the provider subscription system 112. As described herein, this information may be received and processed in a manner to create and maintain complex relationships between organization entities, brand entities, location entities, and gateway entities. Maintaining these relationships may prove useful for enabling efficient searching of medical providers and for identifying an appropriate gateway corresponding to an identified medical provider.

At 120, the process 100 may include enabling a user device (e.g., the user device 104) to search the provider database 118. This may be performed by the provider subscription system 112 based on search queries received from the user devices 104. For example, the users 106 may formulate search queries for medical providers using the user devices 104. These queries may be transmitted to the provider subscription system 112. As described herein, subsequent searching steps may be performed in a manner that obfuscates, from the provider subscription system 112, the medical providers the user 106 is interested in. Depending on the obfuscation technique used, the user device 104 may manage the obfuscation and/or the provider subscription system 112 may manage the obfuscation. Once the appropriate medical provider has been identified, information about the EHR system 114, which is associated with the medical provider, is provided to the user device 104.

At 122, the process 100 may include enabling the user device 104 to connect to a gateway (e.g., a gateway of the EHR system 114) and download health record data. The user device 104 may connect to the EHR system 114 using the information about the EHR system 114 received from the provider subscription system 112. Downloading health record data may include downloading electronic health records using the FHIR standard. In some examples, the user device 104 may connect to and download from more than one EHR system 114.

At 124, the process 100 may include processing medical terms from the health record data to index the medical terms. This may be performed by the user device 104. In some examples, as described herein, indexing the medical terms may include generating medical term expressions corresponding to the medical terms. The medical term expressions may be a serialized form of the medical terms, which may be suitable for storing in a term base located on the user device 104.

At 126, the process 100 may include presenting the health record data based on the indexed medical terms. This may be performed by the user device 104. As described herein, presenting the health record data may include using the indexed medical terms to present the health record data in a uniform manner. This may also include using the indexed medical terms to present contextual information together with the health record data.

At 128, the process 100 may include providing feedback about the indexed medical terms. This may be performed by the user device 104. As described herein, providing feedback about the indexed medical terms may be sent to a terminology management system 130. The terminology management system 130 may be associated with the provider subscription system 112. In some examples, the two systems 112, 130 may be implemented by the same set of computing devices. As described herein, the terminology management system 130 may include automated and manual workflows for updating a term base 132, a version of which was relied upon by the user device 104 when performing the processing at 124.

Figure 2:
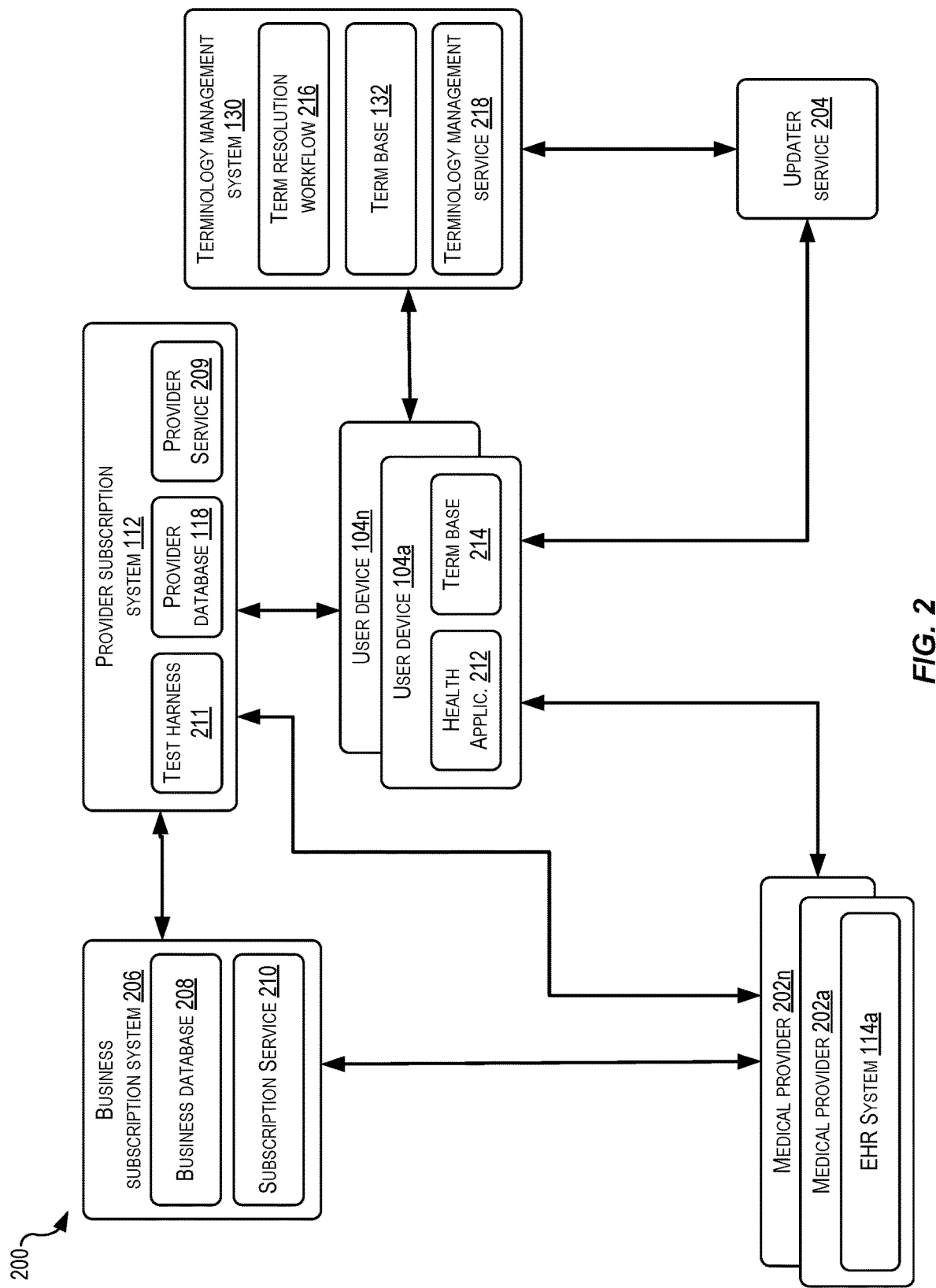
FIG. 2 illustrates a block diagram showing an example architecture or system for enabling storage and retrieval of electronic health records on user devices, according to at least one example.

FIG. 2 illustrates a block diagram showing an example architecture or system 200 for enabling storage and retrieval of electronic health records on user devices, according to at least one example. The system 200 includes a few elements introduced in FIG. 1. In particular, the system 200 includes the provider subscription system 112, one or more user devices 104a-104n, one or more EHR systems 114a-114n associated with one or more medical providers 202a-202n, the terminology management system 130, an updater service 204, and a business subscription system 206. As appropriate and as illustrated by the arrows, the elements of the system 200 may be communicatively coupled via one or more networks.

Beginning with the business subscription system 206, the business subscription system 206 may be any suitable collection of hardware and software components configured to collect, store, update, and otherwise manage business locations including those of the medical providers 202. For example, the business subscription system 206 may include a business database 208 and a subscription service 210 to enable subscription of the medical provider 202. When medical provider 202 is subscribed and active, the user devices 104 may be allowed to connect to and download health record data from the associated EHR system 114 (e.g., a gateway of the EHR system 114).

As part of subscribing and managing subscriptions, the subscription service 210 may include functionality to collect, store, update, and otherwise manage business locations. In some examples, the subscription service 210 provides one or more user interfaces by which authorized users may input information about their location. This information may include geographic information (e.g., a physical address and pin on a map), image information (e.g., logos), contact information (e.g., business, legal, technical, etc.), and any other information relating to a business. The subscription service 210 may also be configured to create and/or update record entries in the business database 208 based on information received. For example, an authorized user associated with the medical provider 202 may share business information with the business subscription system 206. Once this information has been shared and validated, the business information may published for public consumption (e.g., indexed for searching, made available on a map platform, shared directly with users, etc.).

The business database 208 may maintain the collected business information and any relationships between entities represented by the business information. In some examples, the business database 208 includes some or all of the information stored in the provider database 118. For example, because the business subscription system 206 may be used to register all business (not just medical providers 202), records for the medical providers 202 may be maintained in both the business database 208 and the provider database 118. In some examples, the business subscription system 206 shares business information with the provider subscription system 112 in any suitable manner.

Turning now to the provider subscription system 112, the provider subscription system 112 may include the provider database 118 introduced herein, a provider service 209, and a test harness 211. Generally, the provider subscription system 112 may validate the EHR systems 114, maintain information about the medical providers 202 and associated EHR systems 114, enable searching of the medical providers 202 associated with the EHR systems 114, and manage access of the user devices 104 to the EHR systems 114.

After a medical provider 202 associated with an EHR system 114 has been subscribed, the test harness 211 of the provider subscription system 112 may be used to test and/or otherwise validate that a test user using a test user device 104 can connect to and download data from the EHR system 114. In this manner, the test harness 211 may simulate actions that one of the user devices 104 may perform to connect to the EHR system 114. In some examples, the test harness 211 may test this connection when a medical provider 202 is first subscribed and at other times after the initial subscription. For example, the connection may be tested periodically, when certain conditions are fulfilled, and under any other circumstance. If the test is positive, a status indicator(s) in the provider database 118 associated with the medical provider 202, the EHR system 114, and/or a gateway associated with the EHR system 114 may be updated to reflect that the EHR system 114 or the gateway is/are active. If the test is negative, the status indicator(s) may be updated to reflect that the EHR system 114 is inactive. When active, the user devices 104 may be capable of connecting to the gateways of the EHR systems 114. When inactive, the user devices 104 may be unable to connect to the gateways of the EHR systems 114.

The provider service 209 may maintain information about the medical providers 202 and associated EHR systems 114 in the provider database 118, enable searching of the medical providers 202 associated with the EHR systems 114, and manage access of the user devices 104 to the EHR systems 114. In some examples, the user devices 104 send requests to search for the medical providers 202 to the provider service 209. The provider service 209 processes these requests and returns results. In some examples, as part of establishing a connection with one of the EHR systems 114, the user device 104 will check in with the provider service 209 to determine whether any configuration information associated with the EHR system 114 has changed. The configuration information, which may be stored in the provider database 118 may include API information, provider identifiers, status indicator information, and any other suitable information relating to the configuration of the EHR system 114 and/or other entities associated with the EHR system 114.

The user devices 104 may include a health application 212 and a term base 214. Generally, the user devices 104 may be associated with and operated by different users (e.g., patients of the medical providers 202). Functionally, the health application 212 may enable the user devices 104 to communicate with the provider subscription system 112 (e.g., to search for the medical providers 202, obtain configuration information about the medical providers 202, and perform other techniques), communicate with the EHR systems 114 of the medical providers 202 (e.g., to download data packages including electronic health records and/or updates to electronic health records and to perform other such techniques), communicate with the terminology management system 130 (e.g., to upload certain medical terms for refinement), and communicate with the updater service 204 (e.g., to receive updates to the term base 214, indexing rules, and other such information relating to indexing medical terms).

In some examples, the term base 214 may include one or more relational databases or other suitable storage schema for storing expression primitives and/or medical term expressions. For example, the term base 214 may be seeded with expression primitives from the term base 132. As new medical term expressions are generated from medical terms (e.g., as medical terms from the electronic health records are indexed), these new medical term expressions may be stored in the term base 214. Over time, the term base 214 may begin to represent relationships between expression primitives and medical term expressions that are specific to an electronic health record of a user of the user device 104. In this manner, the term base 214 may maintain a personalized relational graph representing the electronic health record of the user.

Example of Personalized Relational Graph

The term base 214 may include a replicated portion of the term base 132. As described herein, the updater service 204 may send updates to the user device 104 including, for example, updates to the term base 214 based on content of the term base 132. The updater service 204 may be configured to send rule sets to the user device 104. For example, these rules may be in the form of Property Lists (plists), other XML files, and in any other suitable form. These rules may be used as part of indexing medical terms.

Given storage considerations, it may be impractical for the term base 214 to include all of the information found in the term base 132. Thus, in some examples, the terminology management system 130, which may be Cloud-based system, may host one or more APIs that can be used to access the term base 132 to page in additional information (e.g., metadata) from the term base 132. In this manner, the user device 104 can selectively download information from the term base 132 to the term base 214 in order to enhance the health record data already stored on the user device 104. In some examples, in addition to metadata, new medical term expressions representing medical concepts, medical categories, medical items, may be downloaded from the term base 132 using the APIs.

To maintain patient privacy, API calls to the terminology management system 130 may include randomized term base identifiers and an obfuscated term index to retrieve the information from the terminology management system 130.

The terminology management system 130 may be configured to manage aspects of the medical terminology described herein. In particular, the terminology management system 130 may receive medical terms from the user devices 104 and resolve their indexing, which may include manual and/or automated processes. For example, if the user device 104 (e.g., the health application 212 and the term base 214) is unable to index a medical term or unable to index the term based on a comparison of indexing scores with one or more thresholds, the user device 104 may upload the medical term and any other associated information to the terminology management system 130. In some examples, a term resolution workflow 216 is implemented to resolve the problematic medical terms. For example, the term resolution workflow 216 may include a set of manual processes for trained users to review the input medical term, the proposed medical term expression, etc. in order to improve the health application 212 and/or other components that index medical terms. When the term resolution workflow 216 resolves a medical term, updates may be made to the term base 132, which may then be pushed or otherwise downloaded by the user device 104. A terminology management service 218 may be configured to manage updates to the term base 132 and interact with other services described herein.

Figure 3:
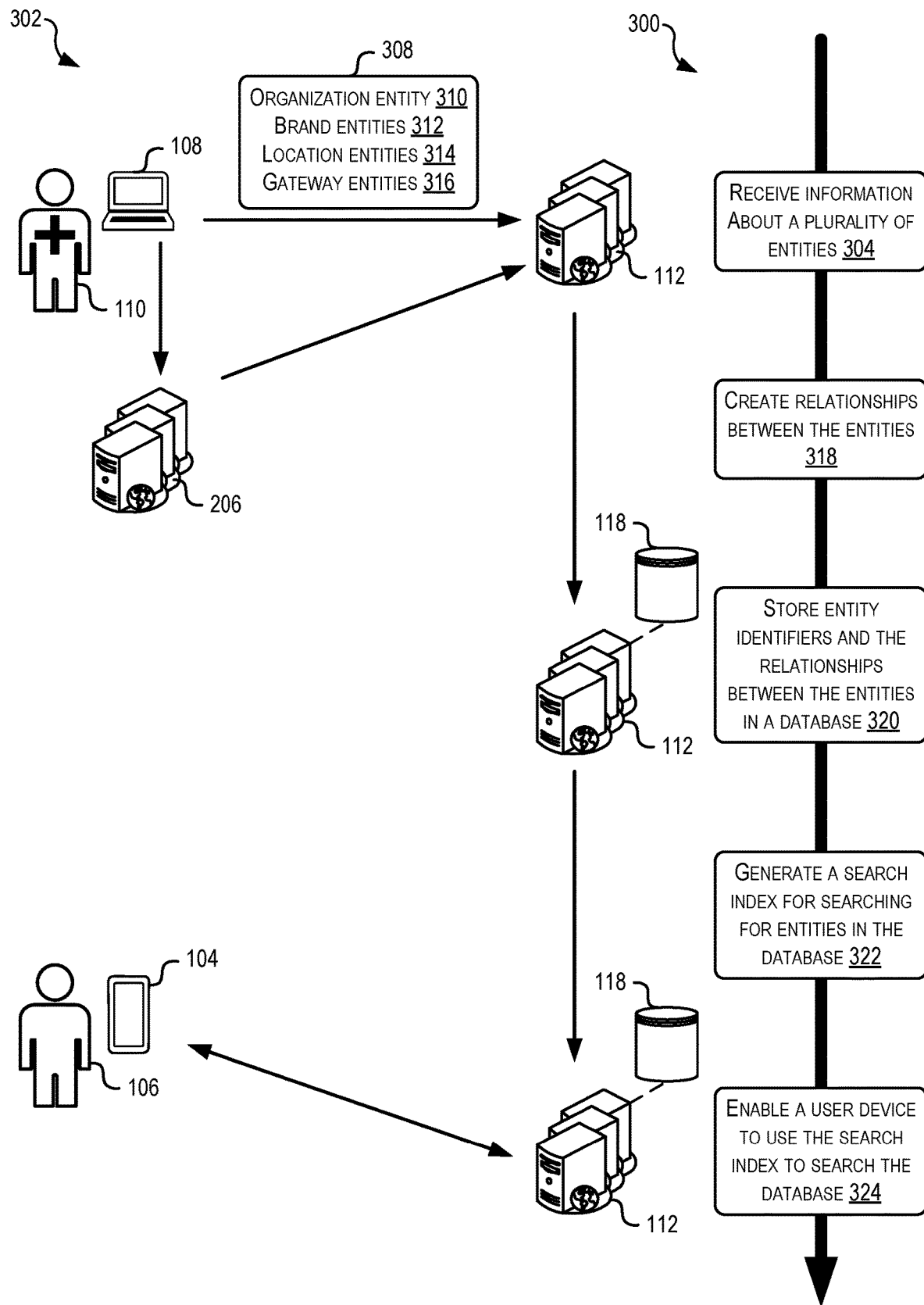
FIG. 3 illustrates a block diagram and a flow chart for onboarding medical provider entities on to a system that enables sharing of electronic health records between user devices and electronic health record systems, according to at least one example.

FIG. 3 illustrates a block diagram 302 and a flow chart showing the process 300 for onboarding medical provider entities on to a system that enables sharing of electronic health records between user devices and the gateways of the EHR systems 114, according to at least one example.

The process 300 may begin at 304 receiving information 308 about a plurality of entities. In some examples, the information 308 may be received by the provider subscription system 112 and from the provider user device 108 and/or the business subscription system 206. For example, the provider user 110 may use the provider user device 108 to provide the information 308 directly to the provider subscription system 112. As an additional example, the provider user 110 may use the provider user device 108 to provide the information 308 to the business subscription system 206. In any event, the information 308 may be transferred to the provider subscription system 112. The information 308 about the plurality of entities may include information defining an organization entity 310, one or more brand entities 312, one or more location entities 314, and/or one or more gateway entities 316. FIGS. 5-17 illustrate in more detail a process by which the provider subscription system 112 may receive the information 308.

Figure 4:
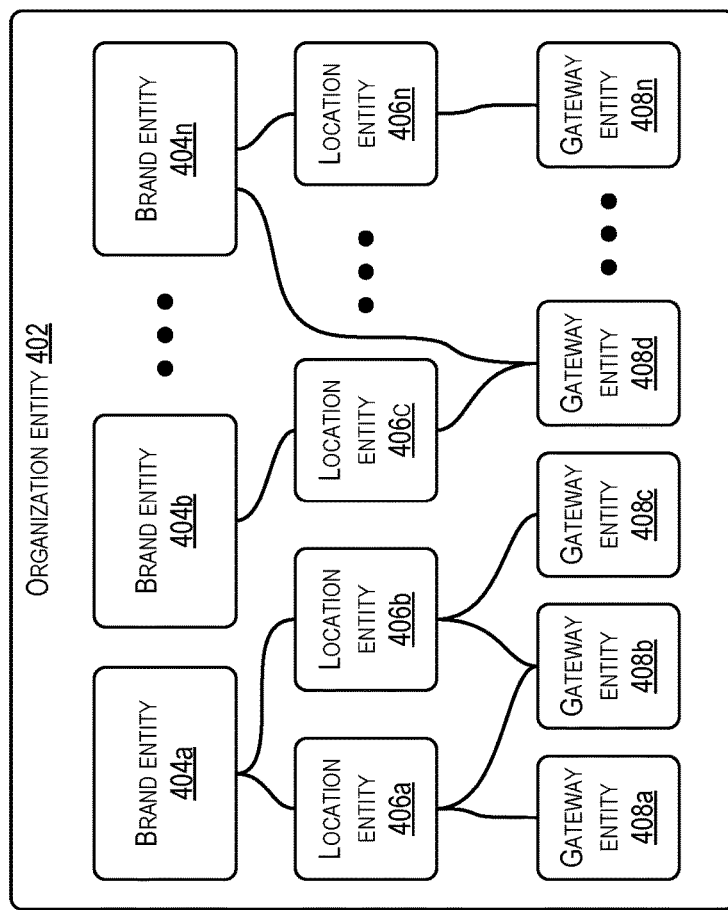
FIG. 4 illustrates a block diagram showing a data structure for storing relationships between entities of an organization entity, according to at least one example.

At 318, the process 300 may include creating relationships between the plurality of entities identified by the information 308. In some examples, this may be performed by the provider subscription system 112. Creating the relationships may be based on the information 308 and/or rule sets that define relationships. FIG. 4 illustrates example relationships between entities.

At 320, the process 300 may include storing entity identifiers and the relationships between the entities in a database. In some examples, this may be performed by the provider subscription system 112, which may store information in the provider database 118. In some examples, the entities may be organized by organization as a primary class, with sub-classes relating to other entities related to the organization (e.g., brands, locations, and/or gateways). In some examples, the storing performed at 320 may include creating a record entry in the provider database 118 for a data object that includes the entity identifiers and associated relationships.

At 322, the process 300 may include generating a search index for searching entities in the database (e.g., the provider database 118). In some examples, this may be performed by the provider subscription system 112. The search index may be any suitable index useable for searching the database.

At 324, the process 300 may include enabling a user device (e.g., the user device 104 operated by the user 106) to use the search index to search the database (e.g., the provider database 118). In some examples, this may be performed by the provider subscription system 112. Enabling the user device 104 may include providing a user interface by which the user 106 can enter search queries for searching for entities. The user 106 may desire to search for the entities in order to find the entities (e.g., brands and/or locations) where the user 106 obtains medical care. The information in the provider database 118 associates these entities with their respective gateway entities where the electronic health record is actually stored. In this way, the user 106 is able to search for provider entities and connect her user device 104 to the gateways associated with the provider entities. This may be desirable because searching for the provider entities (e.g., the locations where the user 106 receives care) may be more natural than searching for a gateway and/or EHR system 114 that hosts the data for those locations where the user 106 receives care.

FIG. 4 illustrates a block diagram showing a data structure 400 for storing relationships between entities of an organization entity 402, according to at least one example. The data structure 400 may include a data object that represents and associates brand entities 404a and 404b-404n, location entities 406a, 406b, and 406c-406n, and gateway entities 408a-408c and 408d-408n, all of which are associated with the same organization entity 402. As illustrated, the organization entity 402 may be associated with any suitable number of brand entities 404, location entities 406, and/or gateway entities 408. Relationships between the entities 404, 406, and 408 are shown using the connecting lines.

The organization entity 402 is an example of an organization (e.g., non-profit, university, corporation, or other business entity) that owns and operates medical care facilities. For example, the organization entity 402 may be a healthcare company such as Mayo Clinic. The organization entity 402 may be the highest level of granularity by which any other entity may be described. In some examples, the organization entity 402 itself is the umbrella under which divisions and/or affiliates operate. The data structure 400 is organized in a way that allows a user to easily search for and find the "place" where she obtains care. Because the organization entity 402 may not actually be the place where care is administered, the brand entities 404 and/or the location entities 406 are used to better represent these places.

The brand entities 404 are examples of the divisions and/or affiliates described above. For example, the organization entity Mayo Clinic may include a plurality of divisions such as Mayo School of Health Sciences, Mayo Medical Laboratory, and Mayo Clinic Health System. These divisions may be represented by the brand entities 404. When a user searches for any of these "places" she will find the data structure 400. The brand entities 404a and 404b-404n are all examples of brands that fall within the organization entity 402.

The location entities 406 are examples of physical locations where the brand entities 404 are located. In some examples, the location entities 406 may be known by different names and/or include multiple physical locations. Thus, the distinction in the data structure 400 between brand entities 404 and the location entities 406. For example, the brand entity 404a may be associated with two location entities 406a, 406b. The two location entities 406a, 406b may be examples of buildings located on a medical campus branded under the brand entity 404a. The location entity 406c is associated with a single brand entity, 404b.

The gateway entities 408 are examples of EHR systems that are used to store health records of patients that visit the brand entities 404 and/or the location entities 406. In addition, the EHR systems may provide patient portals, scheduling, contact management, billing, accounting, imaging management, and other services pertaining to the health care field. Examples of EHR systems include sold by: Epic®, Meditech®, CPSI TM, Cerner®, McKesson®, Healthland®, Siemens®, Allscripts®, and others.

Gateway entities 408 may be associated with more than one location entity 406, with more than one brand entity 404, with a single brand entity 404, and/or a single location entity 406. For example, the gateway entities 408a, 408b are both associated with the location entity 406a. Gateway entities 408 may also be shared across more than one brand entity 404 and/or more than one location entity 406. For example, the gateway entities 408b, 408c are shared between the location entities 406a, 406b. The gateway entities 408a-40bc are all associated with the brand entity 404a (e.g., via the location entities 406a-406c). Gateway entities 408 may also be associated directly with brand entities 404 (e.g., the gateway entity 408d and the brand entity 404n). Gateway entities 408 may also be dedicated to location entities 406 and/or brand entities 404. For example, the gateway entity 408n is dedicated to the location entity 406n. In some examples, a single gateway entity 408 is associated with many location entities 406, which may be associated with a single brand entity 404 and a single organization entity 402. For example, Walgreens Pharmacy may utilize a single gateway entity 408 to service hundreds or even thousands of different location entities 406, all of which may be located at distinct locations, but share in the same Walgreens name (e.g., have the same brand entity 404).

The data structure 400 may maintain these complex relationships between the organization entities 402, the brand entities 404, the location entities 406, and the gateway entities 408. Maintaining these relationships may prove useful for enabling efficient searching of medical providers and for identifying an appropriate gateway corresponding to an identified medical provider.

FIGS. 5-16 illustrate example views 502a-502m of a user interface 500 for onboarding provider entities on to a system that enables sharing of electronic health records between user devices and gateways of electronic health record system, according to at least one example. In particular, FIGS. 5-16 illustrates views 502a-502m of the user interface 500.

The views 502a-502m may be presented as a webpage on a user device or in any other suitable manner. In some examples, the provider subscription system 112 and/or the business subscription system 206 may provide the provider user device 108 operated by the provider user 110.

The view 502a, illustrated in FIG. 5, may include a progress area 504a for tracking progress of a series of actions (e.g., introduction, about yourself, business type, etc.). Each action may be completed as the system receives and processes information. The information may be received by users inputting text in one or more fields within a current action area 506a or by uploading the data in some other manner. In the view 502a, the current action area 506a includes fields for a user to input contact information and/or other information about the person who is providing the information. In some examples, this may be a user authorized by an organization entity to establish the relationship with the subscription system(s) 112, 206.

The view 502b, illustrated in FIG. 6, may include a progress area 504b for tracking progress of a series of actions (e.g., introduction, about yourself, business type, etc.). Each action may be completed as the system receives and processes information. The information may be received by users inputting text in one or more fields within a current action area 506b or by uploading the data in some other manner. In FIG. 6, the current action under consideration is the "Business Type" action. As part of this action, the user may select a business type from the current action area 506b that represents the organization. This is because the user interface 500 and associated system may be used to subscribe many different types of entities. Depending on the entity selected in the current action area 506b, the later data collection steps may be adjusted. For example, in the view 502b, the user has selected healthcare provider 508. Because of this, later data collection steps may be tailored to entities that are healthcare providers 508. In particular, data about gateways of electronic health record systems may be collected.

The remaining actions displayed in the progress area 504b are used to gather business information about the business, information about a head office or headquarters, address and other geographic location information, web links, email addresses, technical contacts, legal contacts, and other similar contacts.

Figure 7:
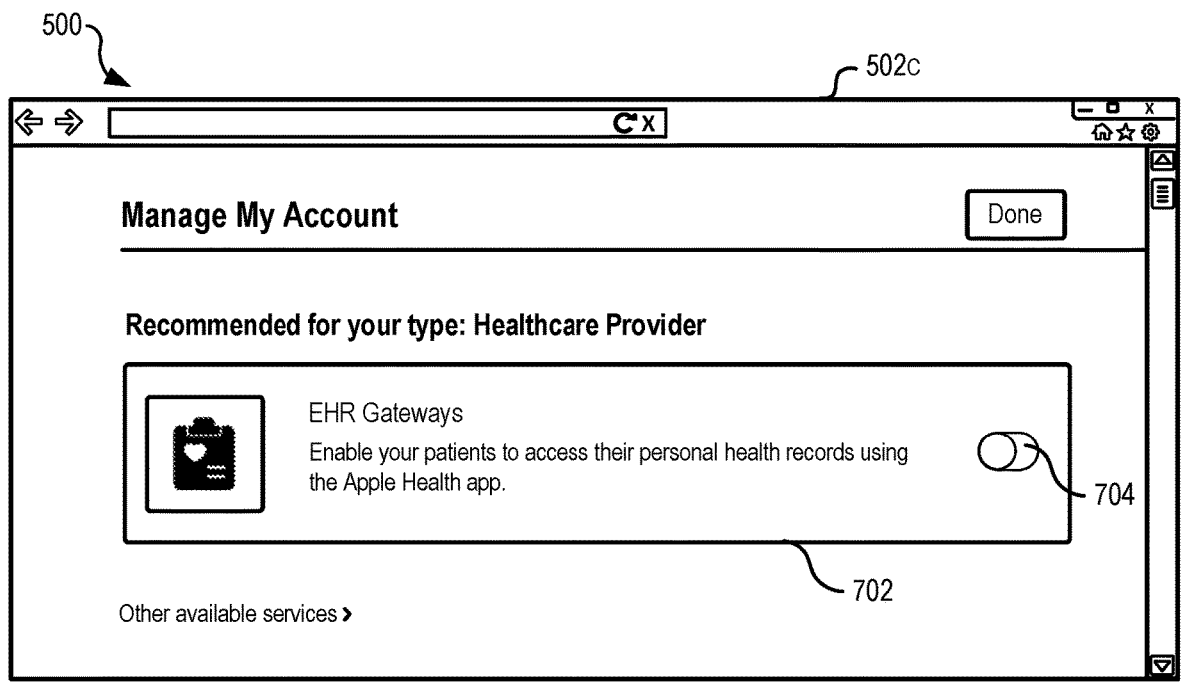

The view 502c, illustrated in FIG. 7, may include a recommendation 702 based on an earlier identification of the healthcare provider 508 as the entity type. The recommendation 702 includes a message that recommends to the user that they enable EHR gateway access. Enabling EHR gateway access may allow patients of the healthcare provider 508 to download health records to their user devices (e.g., mobile, smart phones). To go through the steps of providing information for enabling an EHR gateway, the user may select toggle 704.

Figure 8:
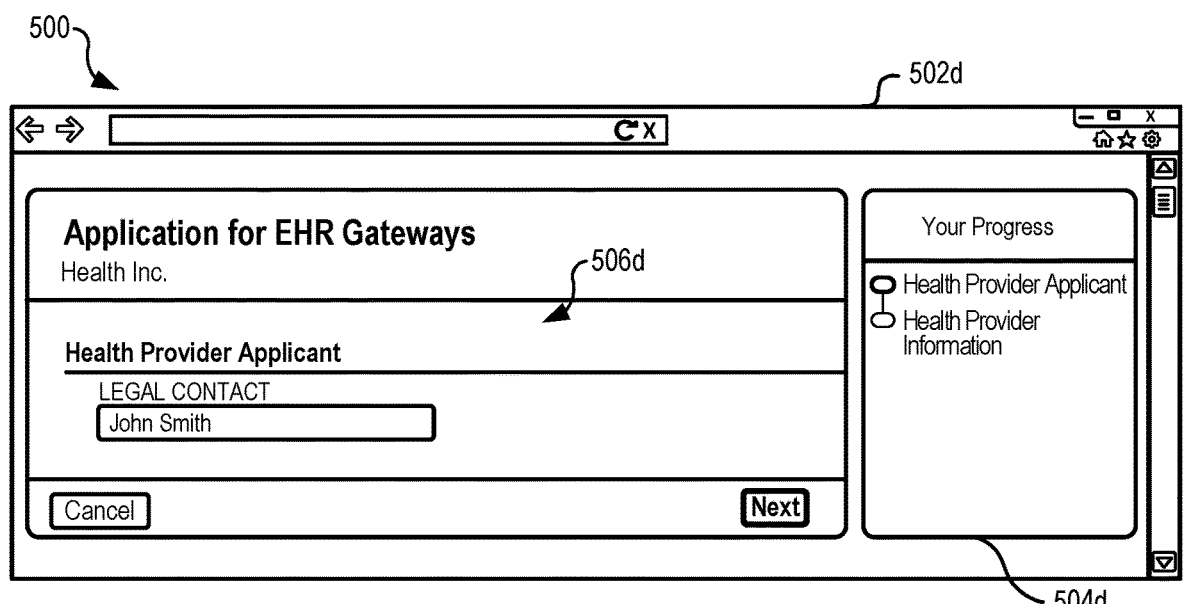

The view 502d, illustrated in FIG. 8, may include a progress area 504d for tracking progress of a series of actions (e.g., health provider application, health provider information). Each action may be completed as the system receives and processes information input by the user. The information may be received by the user inputting text in one or more fields within a current action area 506d or by uploading the information in some other manner. In FIG. 8, as illustrated in the progress area 504d, the user is currently inputting information relating to the "Health Provider Applicant" action. Thus, the current action area 506d includes fields to input contact information for "Health Inc." In this example, information for a legal contact has been requested.

Figure 9:
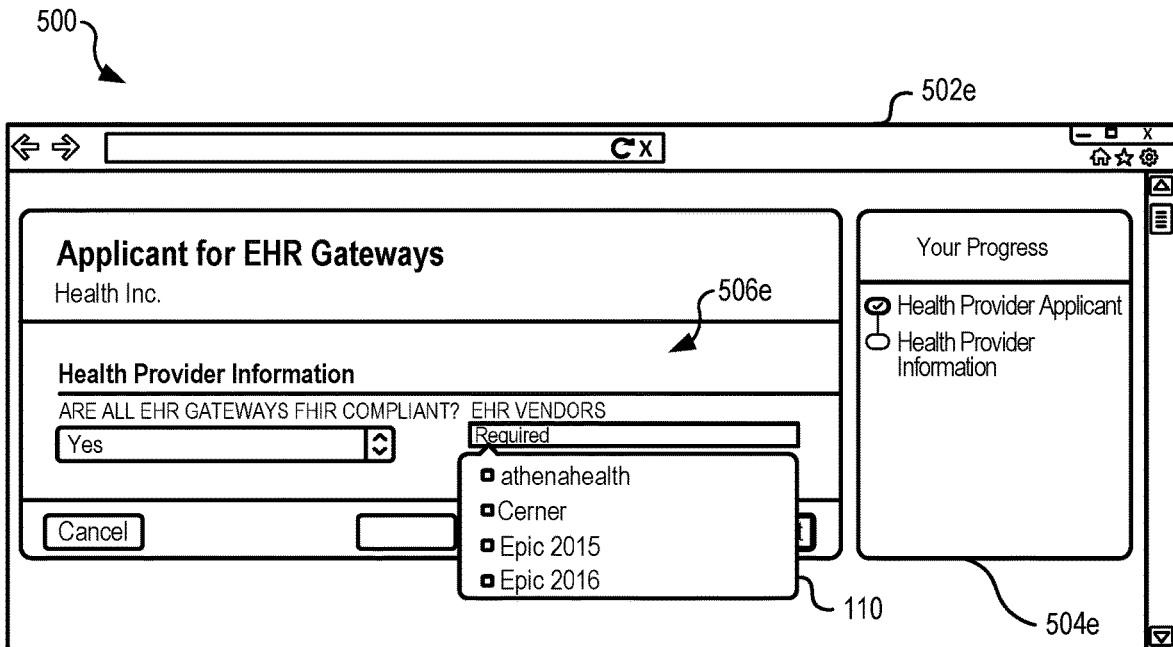

The view 502e, illustrated in FIG. 9, may include a progress area 504e for tracking progress of a series of actions (e.g., health provider application, health provider information). Each action may be completed as the system receives and processes information input by the user. The information may be received by the user inputting text in one or more fields within a current action area 506e or by uploading the information in some other manner. In FIG. 9, as illustrated in the progress area 504e, the user is currently inputting information relating to the "Health Provider Information" action. Thus, the current action area 506e includes fields to input information about EHR gateways operated by the health provider. These fields relate to whether the EHR gateways are FHIR compliant and, if so, the EHR vendor. The EHR gateways are FHIR compliant when they are capable of outputting information using the FHIR standard. The type of information requested at a later time in this workflow may depend on the selected EHR vendor. EHR vendors that are not supported may be grayed out, not included in the list, or may be provided. When provided, a message may be displayed that indicates why the EHR vendor is not supported. Once an EHR vendor has been selected, the view 502f is presented.

Figure 10:
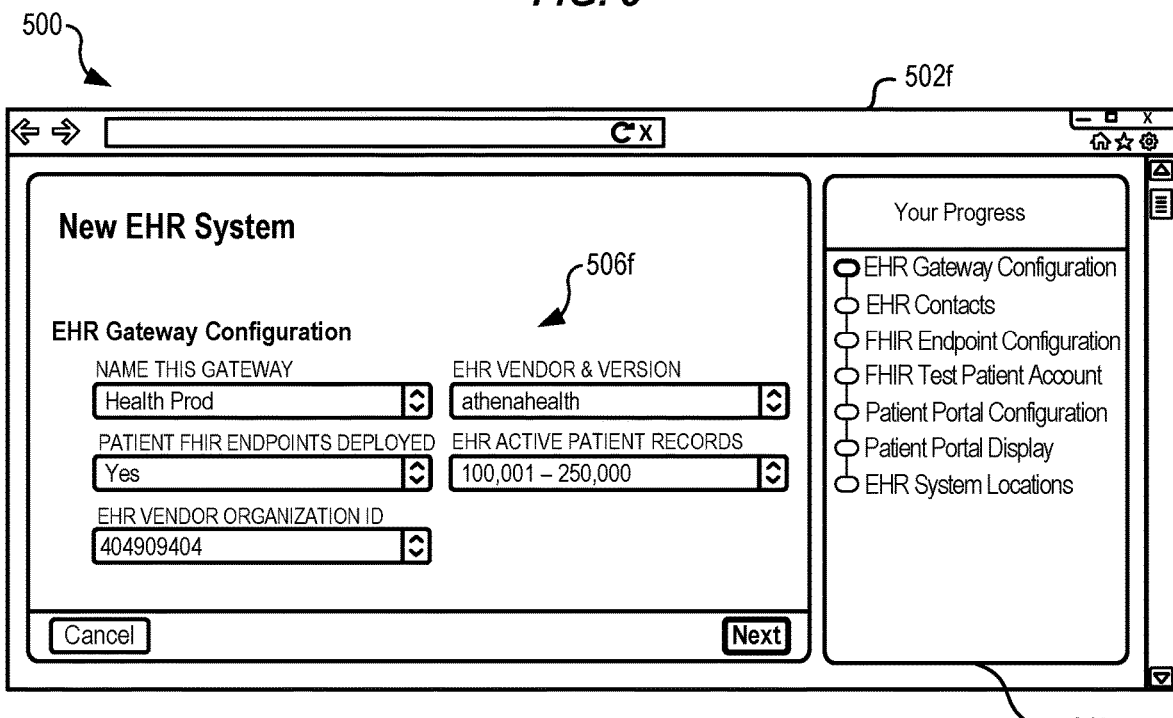

The view 502f, illustrated in FIG. 10, may include a progress area 504f for tracking progress of a series of actions (e.g., EHR gateway configuration, EHR contacts, FHIR endpoint configuration, FHIR test patient account, patient portal configuration, patient portal display, and EHR system locations). Each action may be completed as the system receives and processes information input by the user. The information may be received by the user inputting text in one or more fields within a current action area 506f or by uploading the information in some other manner. In FIG. 10, as illustrated in the progress area 504f, the user is currently inputting information relating to the "EHR gateway configuration" action. Thus, the current action area 506f includes fields to input information particularly about the EHR gateway selected in the view 502e. The action illustrated in the current action area 506f may include assigning the gateway a name (e.g., "Health prod"), identifying the EHR vendor and version (which may be prepopulated), identifying whether patient FHIR endpoints have been deployed, identifying a range of active patient records stored by the EHR gateway, and identifying an EHR vendor organization identifier. Once information has been received using the view 502f, the view 502g is presented.

Figure 11:
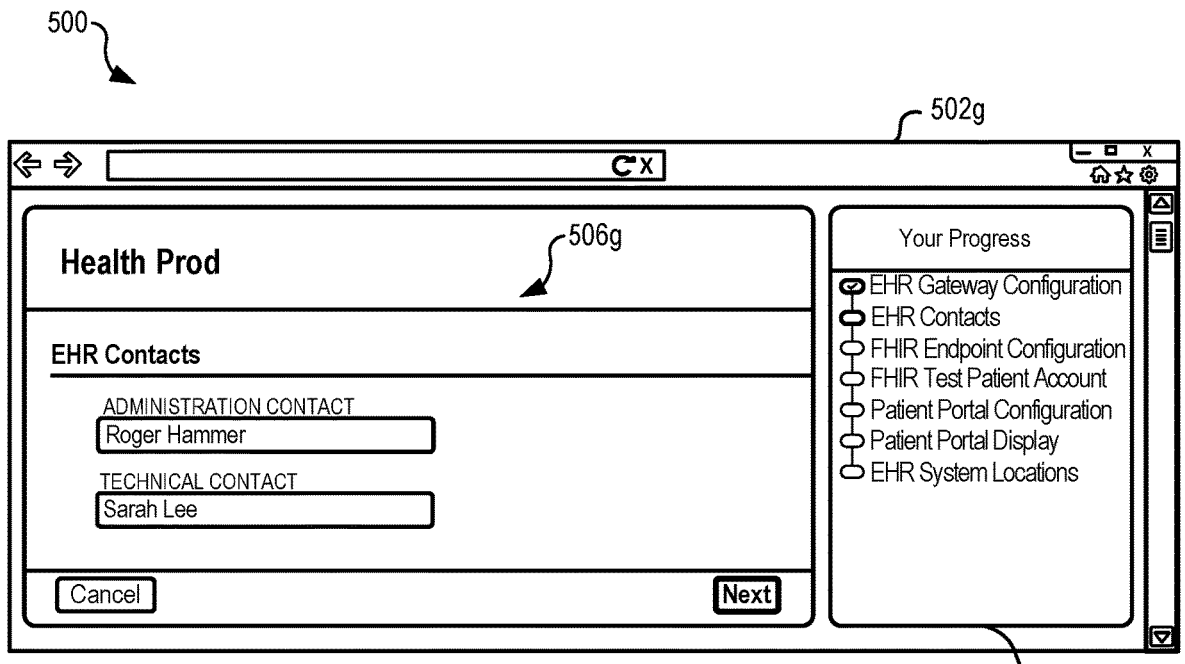

The view 502g, illustrated in FIG. 11, may include a progress area 504g for tracking progress of a series of actions (e.g., EHR gateway configuration, EHR contacts, FHIR endpoint configuration, FHIR test patient account, patient portal configuration, patient portal display, and EHR system locations). Each action may be completed as the system receives and processes information input by the user. The information may be received by the user inputting text in one or more fields within a current action area 506g or by uploading the information in some other manner. In FIG. 11, as illustrated in the progress area 504g, the user is currently inputting information relating to the "EHR contacts" action. Thus, the current action area 506g includes fields to input contact information for the EHR gateway. This may include an administrative contact, technical contact, and other such contacts. Once information has been received using the view 502g, the view 502h is presented.

Figure 12:
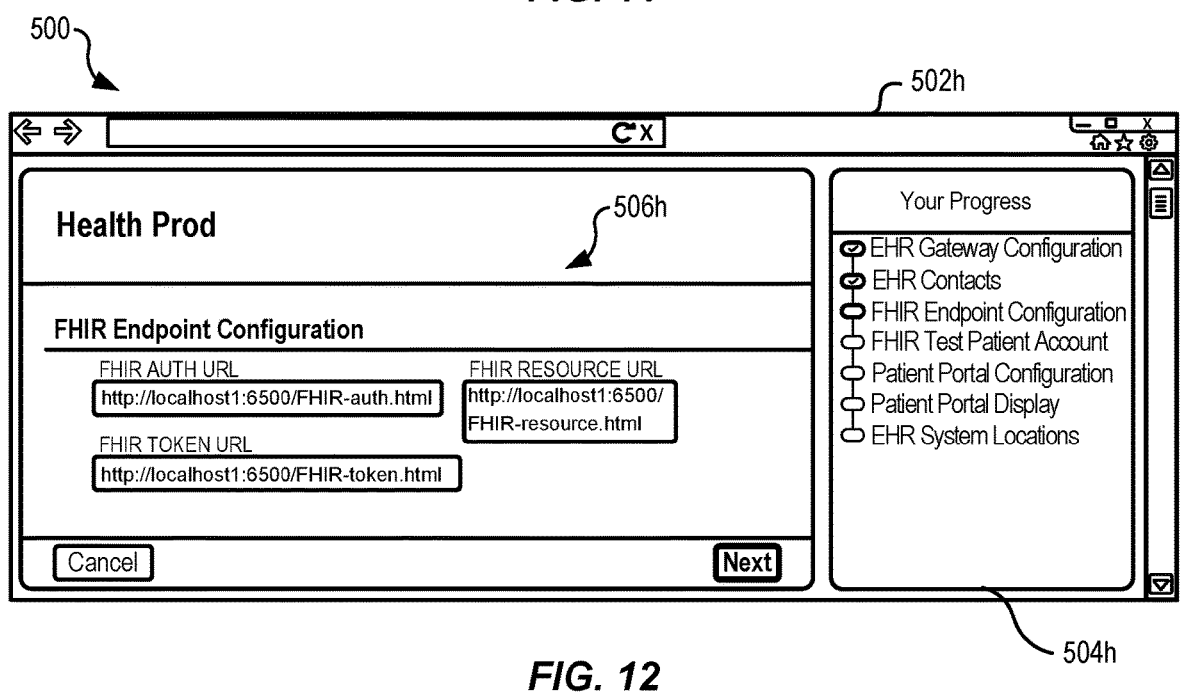

The view 502h, illustrated in FIG. 12, may include a progress area 504h for tracking progress of a series of actions (e.g., EHR gateway configuration, EHR contacts, FHIR endpoint configuration, FHIR test patient account, patient portal configuration, patient portal display, and EHR system locations). Each action may be completed as the system receives and processes information input by the user. The information may be received by the user inputting text in one or more fields within a current action area 506h or by uploading the information in some other manner. In FIG. 12, as illustrated in the progress area 504h, the user is currently inputting information relating to the "FHIR endpoint configuration" action. Thus, the current action area 506h includes fields to input information particular to the FHIR endpoint. Using these fields the user inputs URLs that are specific to the EHR gateway. In some examples, the URLs may be prepopulated based on other information input earlier. In any event, the URLs will be used by other systems for testing user connections and for connecting to the EHR gateway to download health data. Once information has been received using the view 502h, the view 502i is presented.

Figure 13:
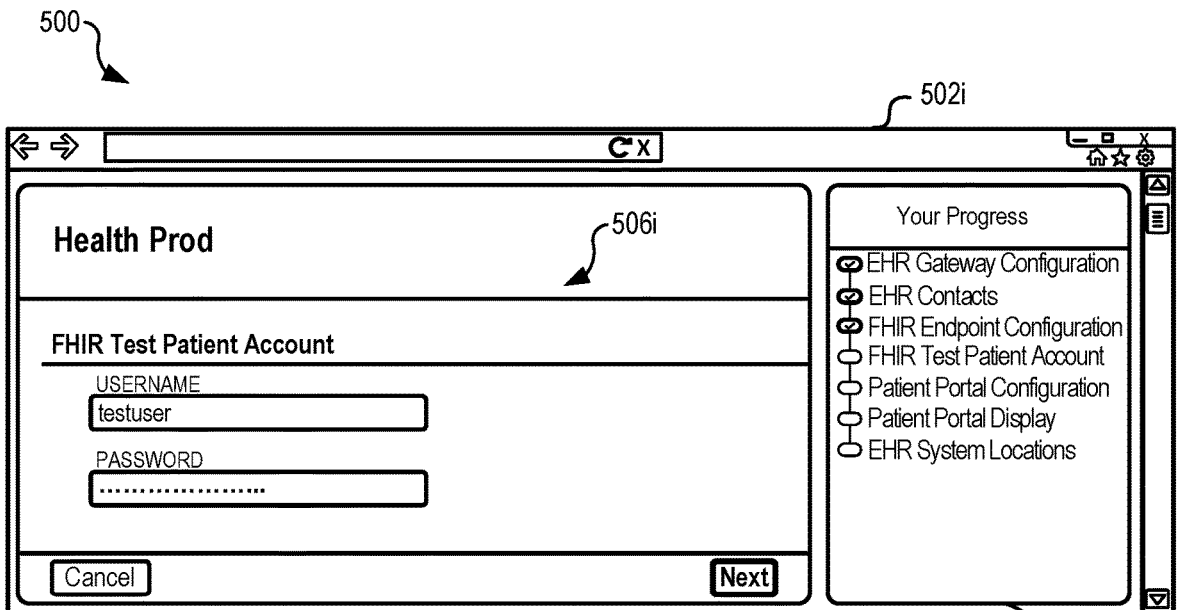

The view 502i, illustrated in FIG. 13, may include a progress area 504i for tracking progress of a series of actions (e.g., EHR gateway configuration, EHR contacts, FHIR endpoint configuration, FHIR test patient account, patient portal configuration, patient portal display, and EHR system locations). Each action may be completed as the system receives and processes information input by the user. The information may be received by the user inputting text in one or more fields within a current action area 506i or by uploading the information in some other manner. In FIG. 13, as illustrated in the progress area 504i, the user is currently inputting information relating to the "FHIR test patient account" action. Thus, the current action area 506i includes fields for a username and password. The username and password may belong to a test profile that the EHR gateway maintains. The username and password may be used periodically to test connections with the EHR gateway (e.g., by the test harness 211). Once information has been received using the view 502i, the view 502j is presented.

Figure 14:
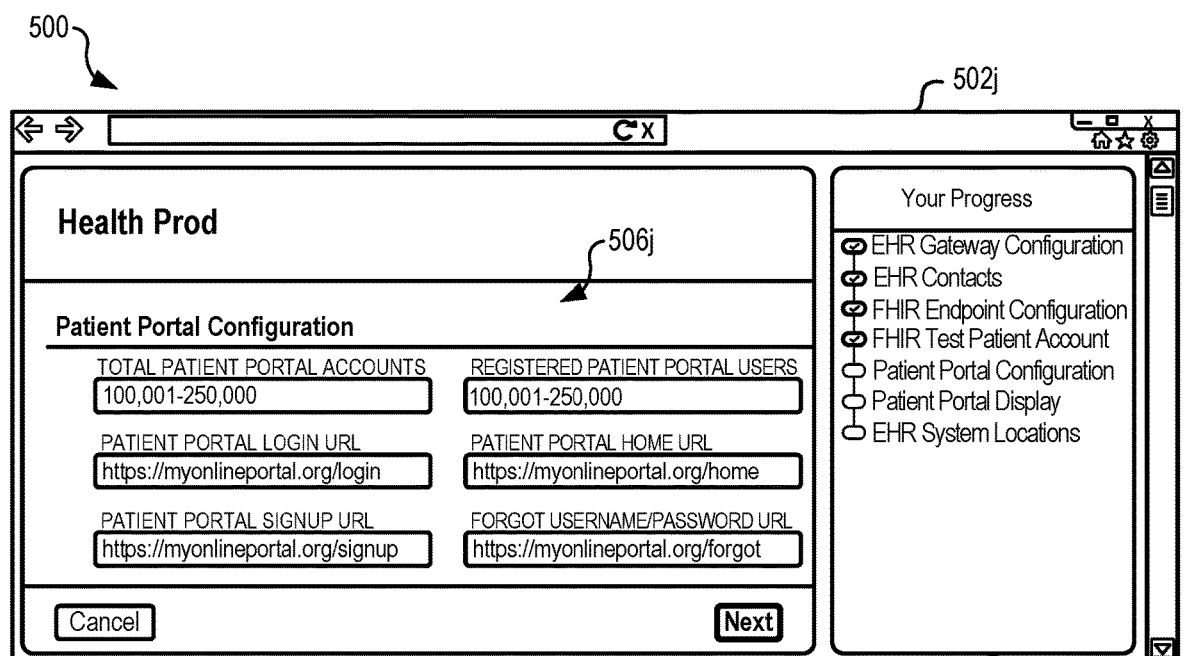

The view 502j, illustrated in FIG. 14, may include a progress area 504j for tracking progress of a series of actions (e.g., EHR gateway configuration, EHR contacts, FHIR endpoint configuration, FHIR test patient account, patient portal configuration, patient portal display, and EHR system locations). Each action may be completed as the system receives and processes information input by the user. The information may be received by the user inputting text in one or more fields within a current action area 506j or by uploading the information in some other manner. In FIG. 14, as illustrated in the progress area 504j, the user is currently inputting information relating to the "patient portal configuration" action. Thus, the current action area 506j includes fields for receiving information for configuring a patient portal. The patient portal may enable a user to connect to the EHR using a web browser to view and/or interact with the EHR gateway. For example, MyChart® provided by EPIC® systems is an example of a patient portal. The systems described herein may use established patient portals to authenticate users who wish to connect to EHR gateways. Thus, the fields in the current action area 506j relate to the patient portal. These fields are used to gather configuration information for the patient portal, which includes size range, registered user range, login URL, home URL, signup URL, and forgot username/password URL. These URLs may be used within the health application 212 when the user device is used to connect to the EHR gateway. For example, even if the user has not previously signed up with the patient portal, a patient portal signup screen can still be presented to the user. Once information has been received using the view 502*j*, the view 502*k* is presented.

Figure 15:
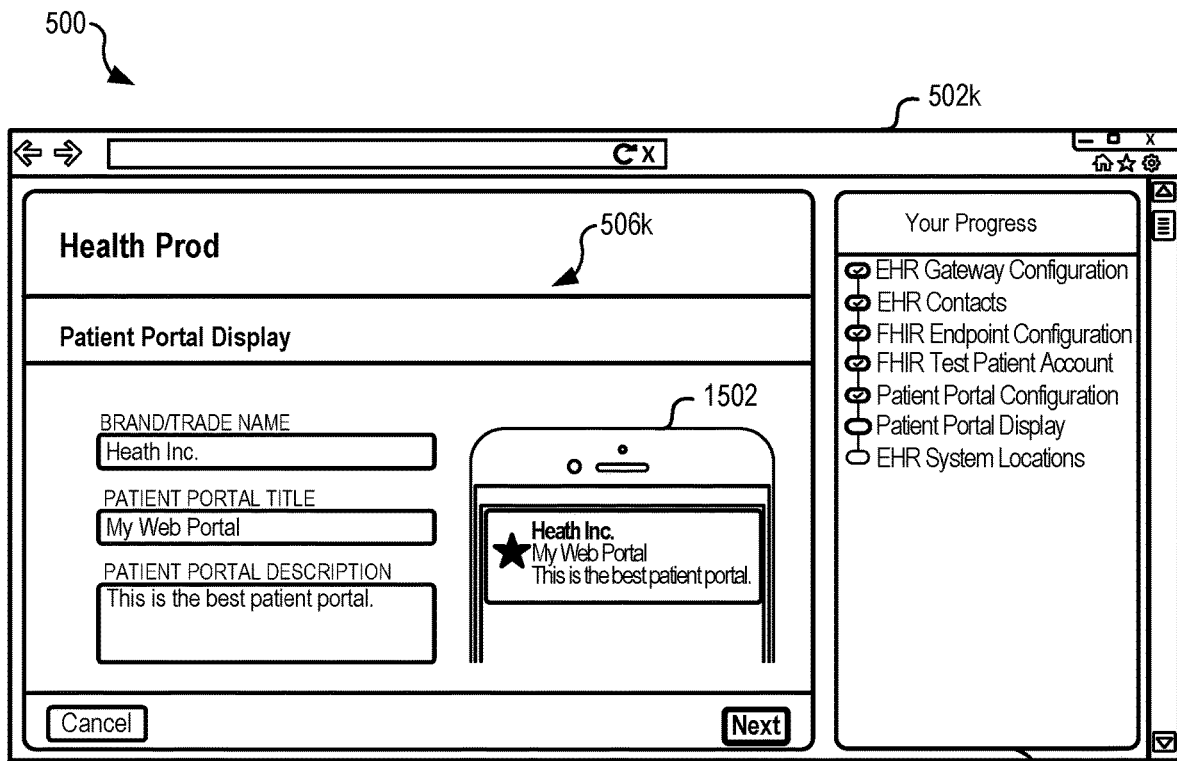

The view 502*k*, illustrated in FIG. 15, may include a progress area 504*k* for tracking progress of a series of actions (e.g., EHR gateway configuration, EHR contacts, FHIR endpoint configuration, FHIR test patient account, patient portal configuration, patient portal display, and EHR system locations). Each action may be completed as the system receives and processes information input by the user. The information may be received by the user inputting text in one or more fields within a current action area 506*k* or by uploading the information in some other manner. In FIG. 15, as illustrated in the progress area 504*k*, the user is currently inputting information relating to the "patient portal display" action. Thus, the current action area 506*k* includes fields for receiving particular branding information for the EHR gateway. This may include information relating to a brand/ tradename, a patient portal title, a patient portal description, images, and an example representation 1502 of how the EHR gateway will look in the health application 212. Once information has been received using the view 502*k*, the view 502*l* is presented.

Figure 16:
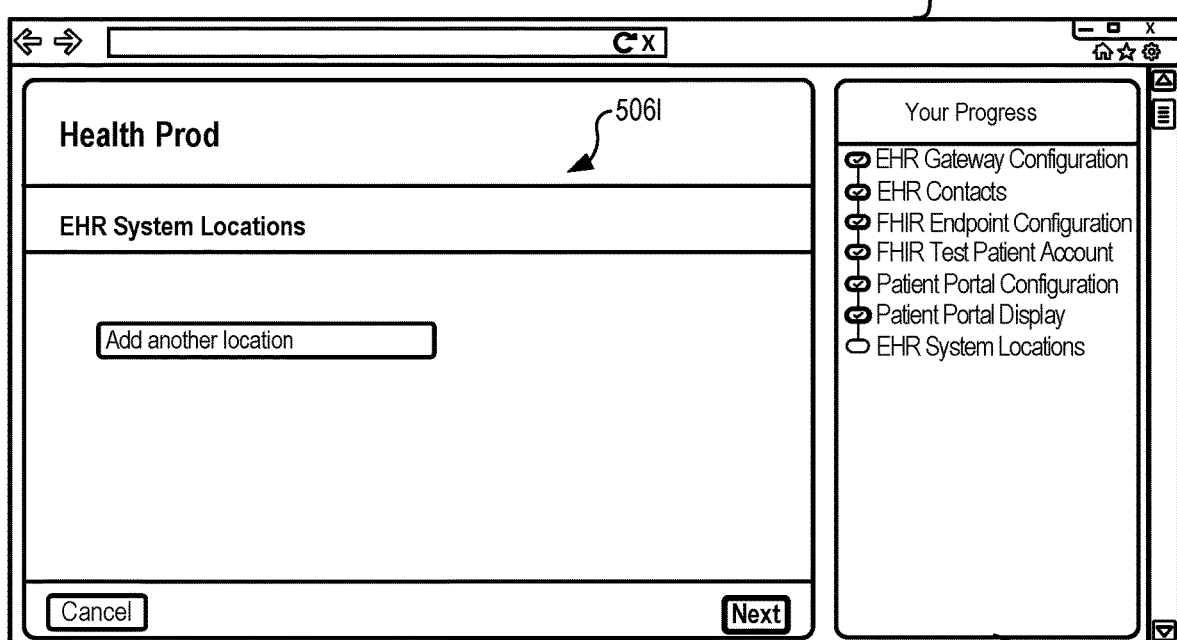

The view 502*l*, illustrated in FIG. 16, may include a progress area 504*l* for tracking progress of a series of actions (e.g., EHR gateway configuration, EHR contacts, FHIR endpoint configuration, FHIR test patient account, patient portal configuration, patient portal display, and EHR system locations). Each action may be completed as the system receives and processes information input by the user. The information may be received by the user inputting text in one or more fields within a current action area 506*l* or by uploading the information in some other manner. In FIG. 16, as illustrated in the progress area 504*l*, the user is currently inputting information relating to the "EHR system locations" action. Thus, the current action area 506*l* includes a toggle button for adding another location. For example, if the provider "Health Inc." includes more than one EHR system, the user may add the information about this EHR system using the toggle button. In some examples, this may cause a repeat of the progress actions illustrated in the progress area 504*l*. Once information has been received using the view 502*l*, the view 502*m* is presented.

Figure 17:
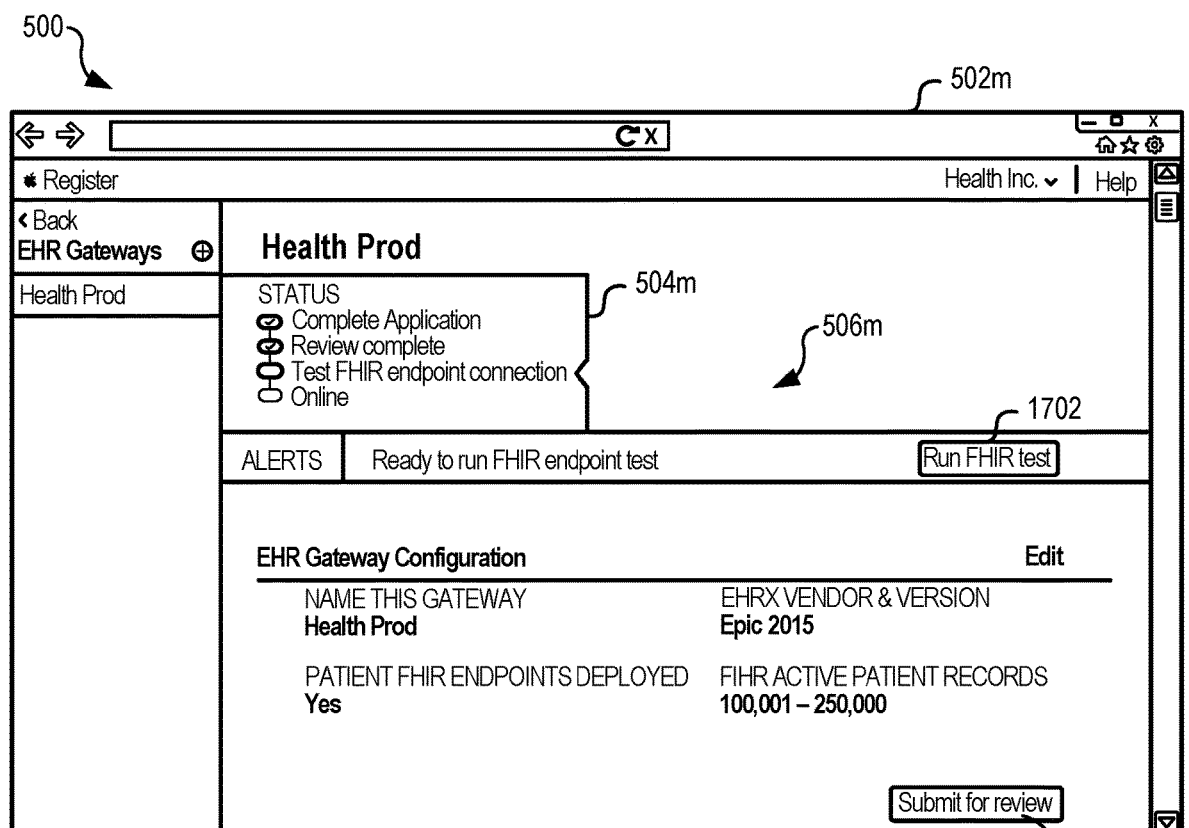

The view 502*m*, illustrated in FIG. 17, may include a progress area 504*m* for tracking progress of a series of actions (e.g., complete application, review complete, test FHIR configuration, etc.). Each action may be completed as the system receives and processes information input by the user. In FIG. 17, as illustrated in the progress area 504*m*, the user is currently on the "test FHIR endpoint connection" action. The "complete application" action was previously performed with respect to FIGS. 7-16. The "review complete" action may have been performed by the entity that operates the provider subscription system 112 and/or the business subscription system 206. In some examples, the "review" action is a manual process and/or an automated process. In a current action area 506*m*, is illustrated information about a FHIR endpoint of the EHR gateway. The current action area 506*m* may also include a test button 1702 and a review button 1704. Selecting the test button 1702, the enable the system to go through a predefined test (e.g., a simulation) routine to test the FHIR endpoint. This test routine may include attempting to connect to the EHR gateway at the FHIR endpoint using the test patient username and the test patient password input in the view 502*i*. If the connection is successful, the system also attempt to download health record data from the FHIR endpoint as a FHIR data package. Once the test has been successfully run, the review button 1704 may be selected to submit the FHIR endpoint for final review prior to be published and made available for user searching. In some examples, the information input using the views 502*a*-504*m* may be used to generate the data structure 400.

Figure 18:
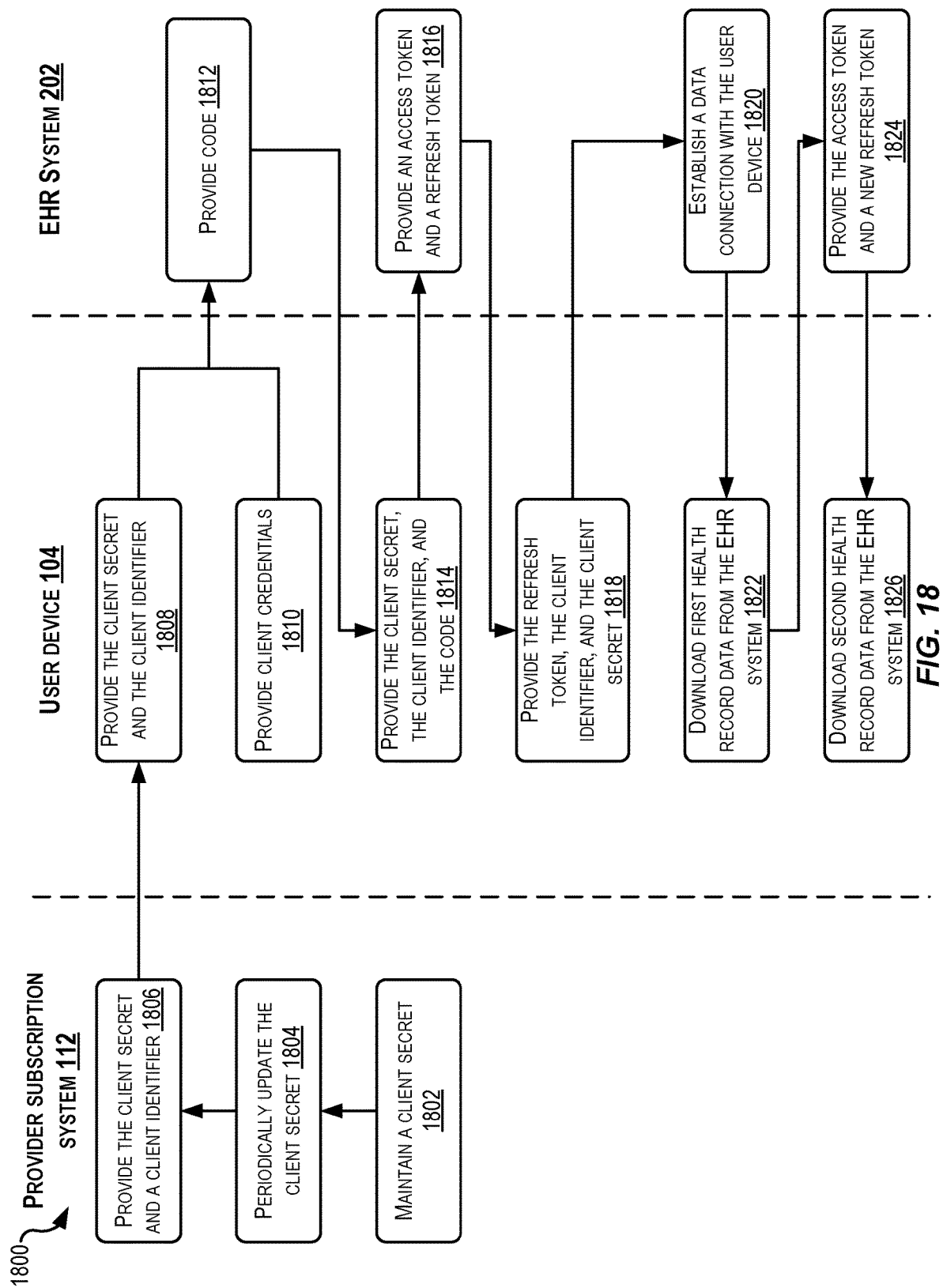
FIG. 18 illustrates an example flow chart showing a process for managing user authentication as part of establishing connections to medical provider entities to download electronic health records of the electronic health record systems, according to at least one example.

FIG. 18 illustrates an example flow chart showing the process 1800 for managing user authentication as part of establishing connections to gateways of EHR systems 114 to download electronic health records from the medical provider entities, according to at least one example. The process 1800 may be performed by the provider subscription system 112, the user device 104, and/or the EHR system 114, including a gateway entity.

The process 1800 may begin at 1802 maintaining a client secret. This may be performed by the provider subscription system 112. The client secret may be specific to a particular EHR system and/or to particular brand of EHR systems.

At 1804, the process 1800 may include periodically updating the client secret. This may be performed by the provider subscription system 112. In some examples, updating the client secret may include generating a new client secret. Updating the client secret periodically may include updating the client secret at a set interval (e.g., every month), in response to fulfillment of certain conditions, and at any other time. In some examples, updating the client secret may be performed when there is concern that the client secret may have been compromised.

At 1806, the process 1800 may include providing the client secret and a client identifier. This may be performed by the provider subscription system 112. The client identifier may be specific to the user device 104 and/or a user account associated with a user of the user device 104. In some examples, the client secret and the client identifier may be provided to the user device 104.

At 1808, the process 1800 may include providing the client secret and the client identifier. This may be performed by the user device 104. In some examples, the user device provides the client secret and the client identifier to the EHR system 114.

At 1810, the process 1800 may include providing client credentials. This may be performed by the user device 104. The client credentials may be specific to a user associated with the user device 104. The client credentials may be associated with a patient portal of the EHR system 114. The user device 104 may provide the client credentials to the EHR system 114. In this manner the user may log in to the user portal at the EHR system 114.

At 1812, the process 1800 may include providing a code. This may be performed by the EHR system 114. The code may be generated by the EHR system 114 for purposes of connecting with the user device 104. The EHR system may provide the code to the user device 104.

At 1814, the process 1800 may include providing the client secret, the client identifier, and the code. This may be performed by the user device 104. These items may be provided to the EHR system 114 in response to receiving the code.

At 1816, the process 1800 may include providing an access token and a refresh token. This may be performed by the EHR system 114. These items may be provided to the user device 104. These item(s) may be used by the user device 104 at a later time to access the EHR system 114. When later communications from the user device 104 include these item(s), and in some examples other information, the EHR system 114 may process the communications (e.g., download data to the user device 104).

At 1818, the process 1800 may include provide the refresh token, the client identifier, and the client secret. This may be performed by the user device 104. These items may be provided to the EHR system 114. In some examples, providing this information may enable a connection to be established between the user device 104 and the EHR system 114.

At 1820, the process 1800 may include establishing a data connection with the user device. This may be performed by the EHR system 114. In some examples, establishing the data connection may depend in part on receiving the refresh token, the client identifier, and the client secret.

At 1822, the process 1800 may include downloading first health record data from the EHR system 114. This may be performed by the user device 104. Such downloading, like the other communications described herein, may take place over any suitable network or combination of networks. The first health record data may be associated with an electronic health record of a user of the user device 104.

At 1824, the process 1800 may include providing the access token and a new refresh token. This may be performed by the EHR system 114. These items may be provided to the user device 104.

At 1826, the process 1800 may include downloading second health record data from the EHR system 114. This may be achievable based on the access token and the new refresh token.

Figure 19:
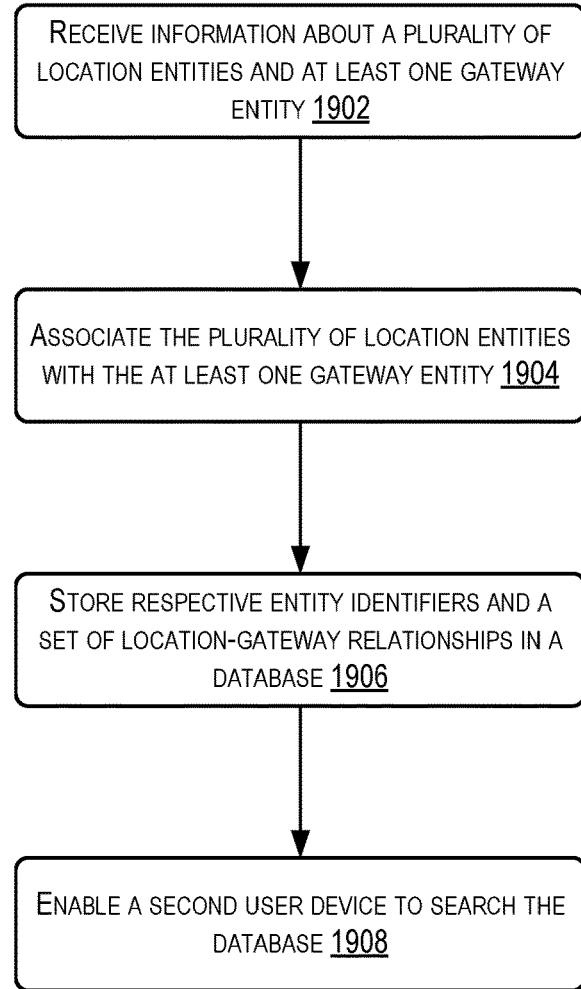
FIG. 19 illustrates an example flow chart showing a process for managing entity relationships, according to at least one example.

FIG. 19 illustrates an example flow chart showing the process 1900 for managing entity relationships, according to at least one example. The process 1900 may be performed by the provider subscription system 112 and/or the business subscription service 206.

The process 1900 may begin at 1902 by receiving information about a plurality of location entities and at least one gateway entity. The information may be received from a first user device such as a provider user device operated by a provider user (e.g., an authorized user). The plurality of location entities and the at least one gateway entity may be associated with respective entity identifiers. The entity identifiers may be assigned to the entities in any suitable manner and may uniquely identify the entities.

In some examples, receiving the information may include receiving at least a first portion of the information from a configuration file uploaded to the server from the first user device. In this example, the configuration file may include configuration information useable by the second user device for connecting to the at least one gateway.

In some examples, the information comprises configuration information useable by the second user device for connecting to the at least one gateway. The configuration information may include a plurality of links resolving to the at least one gateway.

At 1904, the process 1900 may include associating the plurality of location entities with the at least one gateway entity. This may be based at least in part on the information received at 1902. In some examples, associating the plurality of location entities with the at least one gateway entity creates a set of location-gateway relationships. The at least one gateway may be shared between at least two of the plurality of location entities. In some examples, the gateway may be devoted to a single location entity.

At 1906, the process 1900 may include storing the respective entity identifiers and the set of location-gateway relationships in a database. The database, which may be referred to as a provider database, may include a plurality of data objects representing a plurality of organizations each including locations, brands, and gateways.

At 1908, the process 1900 may include enabling a second user device to search the database. The second user device may be a device of a patient or other user who is interested in downloading health record data. Such searching may be for at least one entity of the plurality of location entities or the at least one gateway entity.

In some examples, the process 1900 may further include, prior to receiving the information, providing a user interface at the user device, the user interface comprising a plurality of text fields. In this example, receiving the information at 1902 may include receiving at least a first portion of the information via text input into the plurality of text fields. An example user interface is illustrated in FIGS. 5-17.

In some examples, the process 1900 may further include, prior to storing the respective entity identifiers and the set of location-gateway relationships in a database, simulating a user connection to the at least one gateway using test user credentials identified from the information.

In some examples, the information may include information about a plurality of brand entities. In this example, the process 1900 may further include associating, based at least in part on the information, the plurality of brand entities with the plurality of location entities to create a set of brand-location relationships. At least two location entities of the plurality of location entities may be shared between at least one location entity of the plurality of location entities. In this example, the process 1900 may further include storing the respective entity identifiers and the set of brand-location relationship in the database. The respective entity identifiers, the set of location-gateway relationships, and the set of brand-location relationships may be stored in a data object associated with an organization entity.

Figure 20:
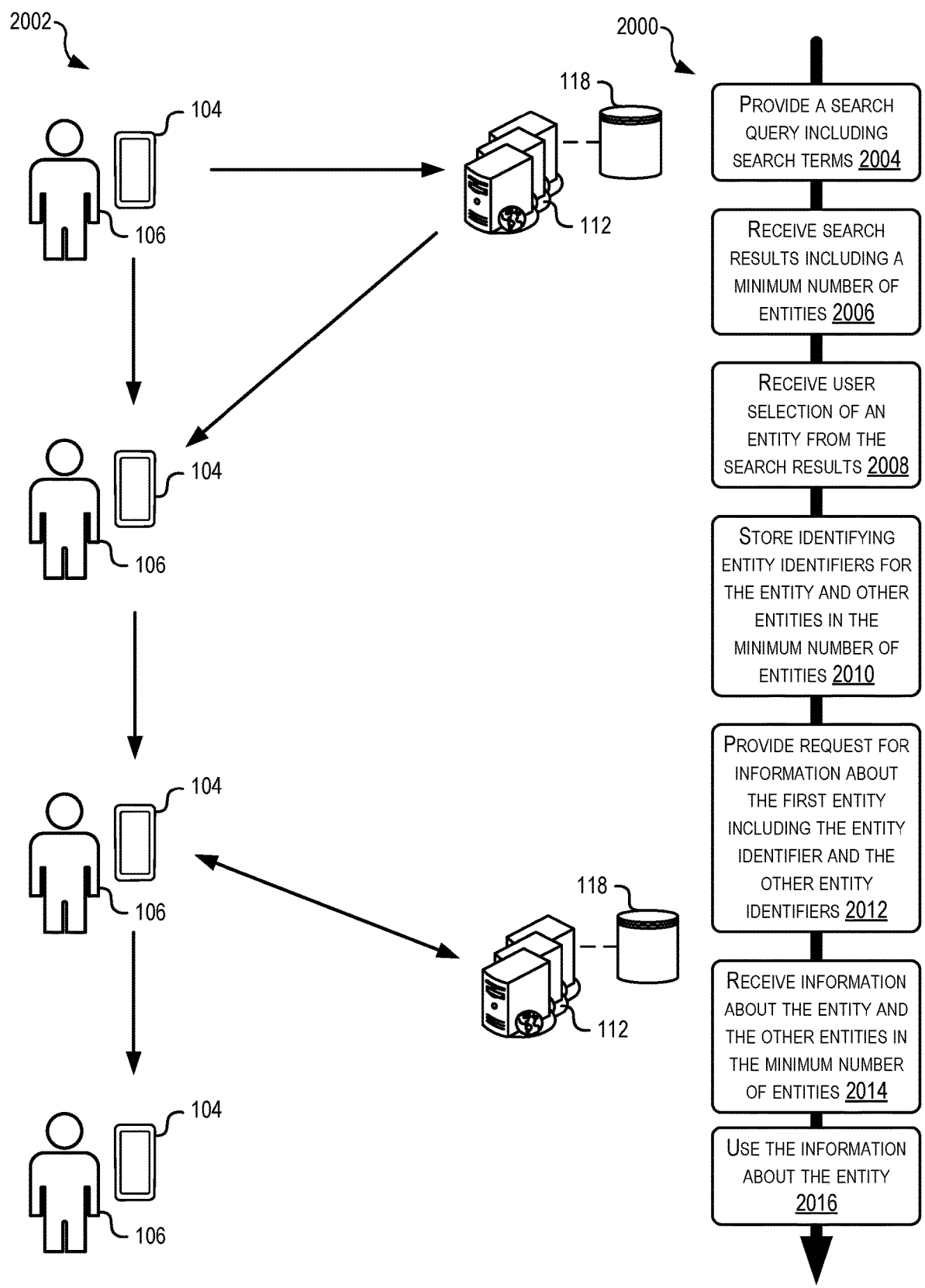
FIG. 20 illustrates an example flow chart showing a process for enabling anonymized user searching of medical provider entities, according to at least one example.

FIG. 20 illustrates a block diagram 2002 and a flowchart showing the process 2000 for anonymized user searching of medical provider entities, according to at least one example. The diagram 2002 includes the user device 104, which may be operated by the user 106, and the provider subscription system 112 including the provider database 118.

The process 2000 may begin at 2004 by providing a search query including search terms. This may be performed by the user device 104. In some examples, the user 106 may operate the user device 104 to input the search terms, which may then be provided to the provider subscription system 112. The search terms may relate to a medical provider that the user 106 desires to find. Once found, the user 106 may operate the user device 104 to connect to a gateway of an EHR system of the medical provider and download her electronic health record.

At 2006, the process 2000 may include receiving search results including a minimum number of entities. This may be performed by the user device 104. The provider subscription system 112 may process the search query to identify the minimum number of entities from the provider database 118. The entities in the minimum number may be location entities, brand entities, and/or gateway entities, all of which may be considered medical provider entities. The minimum number may correspond to some fixed value such as, for example, five, ten, twenty, fifty, etc. If processing the search query alone does not result in the minimum number (e.g., if the search terms were too narrow), the provider subscription system 112 may automatically add additional entities to the set to reach the minimum number.

At 2008, the process 2000 may include receiving user selection of an entity from the minimum number of entities. This may be performed by the user device 104. For example, the user 106 may use the user device 104 to select the entity from a list including the minimum number of entities. This may be the entity that the user 106 is interested in connecting to (e.g., a location where the user 106 obtains medical care).

At 2010, the process 2000 may include storing identifying entity identifiers for the entity and other entities in the minimum number of entities. This may be performed by the user device 104. For example, upon selection of the entity from the list, e.g., at 2008, the user device 104 may automatically store identifiers for the entities from the minimum number of entities. The identifiers may be universal unique identifiers, which may be generated by the provider subscription system 112 or assigned in some other manner.

At 2012, the process 2000 may include providing a request for information about the first entity. The request may include the entity identifier and the other entity identifiers. This may be performed by the user device 104. For example, the user device 104 may provide the request to the provider subscription system 112. Thus, even though the user 106 is only interested in the first entity, the user device 104 may nevertheless send identifiers for the first entity together with the other entity identifiers. In this manner, the entity that the user 106 is actually interested in is obfuscated from the provider subscription system 112. When later calls are made by the user device 104 to the provider subscription system 112 for information about the first entity, the same set of identifiers may be used.

At 2014, the process 2000 may include receiving information about the entity and the other entities in the minimum number of entities. This may be performed by the user device 104. For example, the provider subscription system 112 may gather up the information, e.g., from the provider database 118 or other location, and send the information to the user device 104. Again, even though the user 106 is only interested in the first entity, the user device 104 receives information about all entities from the minimum number of entities. However, because the user device 104 is aware that the first entity is what the user 106 is actually interested in, the user device 104 may sort through the information received to identify the relevant information about the first entity and disregard the other information about the other entities.

At 2016, the process 2000 may include using the information about the entity. This may be performed by the user device 104. Using the information may include using the information to connect to a gateway entity associated with the entity to download health record data to the user device 104.

FIGS. 21-33 illustrate a series of processes, decision points, and user interface (UI) views relating to a user operating a health application of a user device to connect to a gateway entity for downloading health record data, according to various examples. In particular, FIGS. 21-24 include processes (a), (b), (c), (d), decision points (A), (B), (C), (D), (E), (F), (G), and (H), and user interface (UI) views labeled (1) through (25) that result from the processes (a)-(d) and the decisions points (A)-(H). A selection made at a UI view that carries over between a first FIG. and a second FIG. is illustrated, for example, using a graphic of the following form: 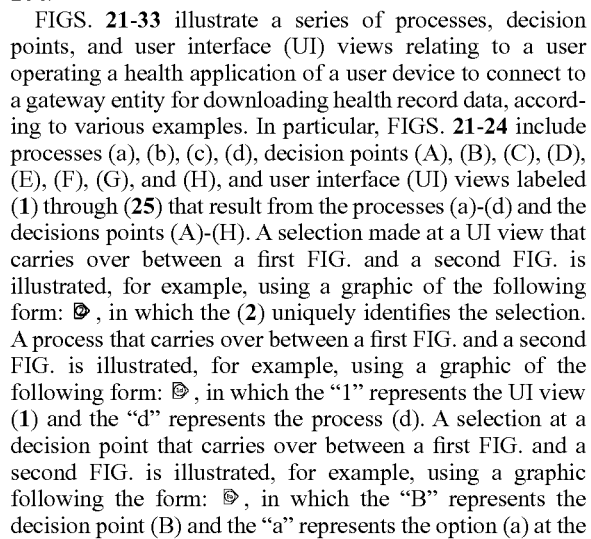, in which the (2) uniquely identifies the selection. A process that carries over between a first FIG. and a second FIG. is illustrated, for example, using a graphic of the following form: 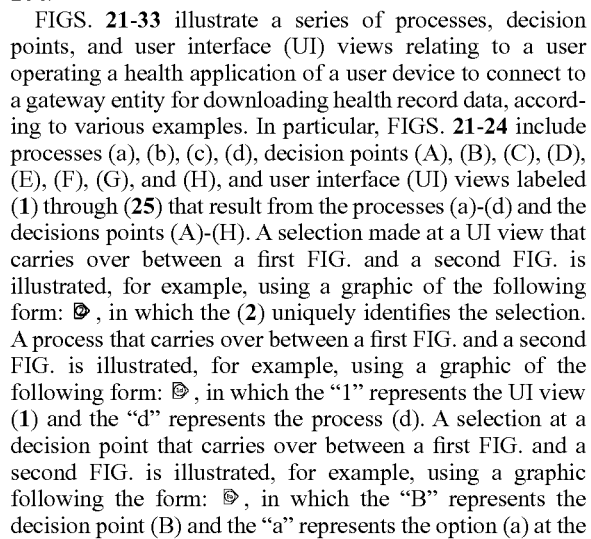, in which the "1" represents the UI view (1) and the "d" represents the process (d). A selection at a decision point that carries over between a first FIG. and a second FIG. is illustrated, for example, using a graphic following the form: 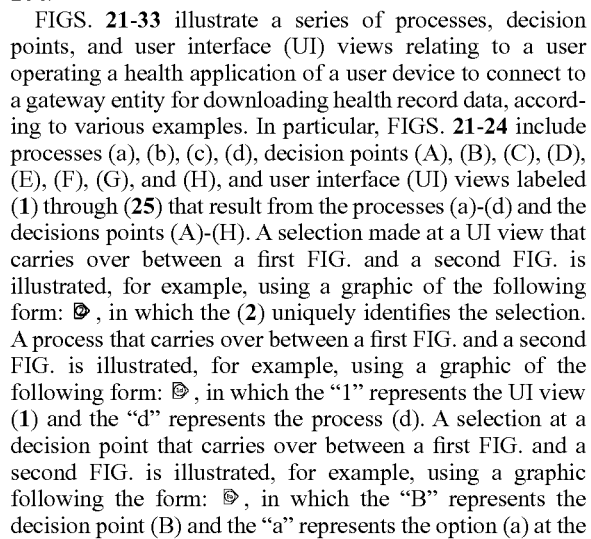, in which the "B" represents the decision point (B) and the "a" represents the option (a) at the decision point (B). A selection that is directed to a decision point and carries over between a first FIG. and a second FIG. is illustrated, for example, using a graphic following the form: 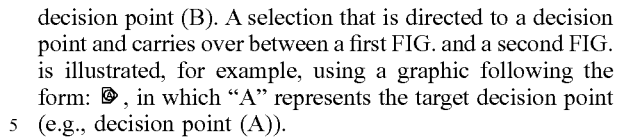, in which "A" represents the target decision point (e.g., decision point (A)).

Figure 21:
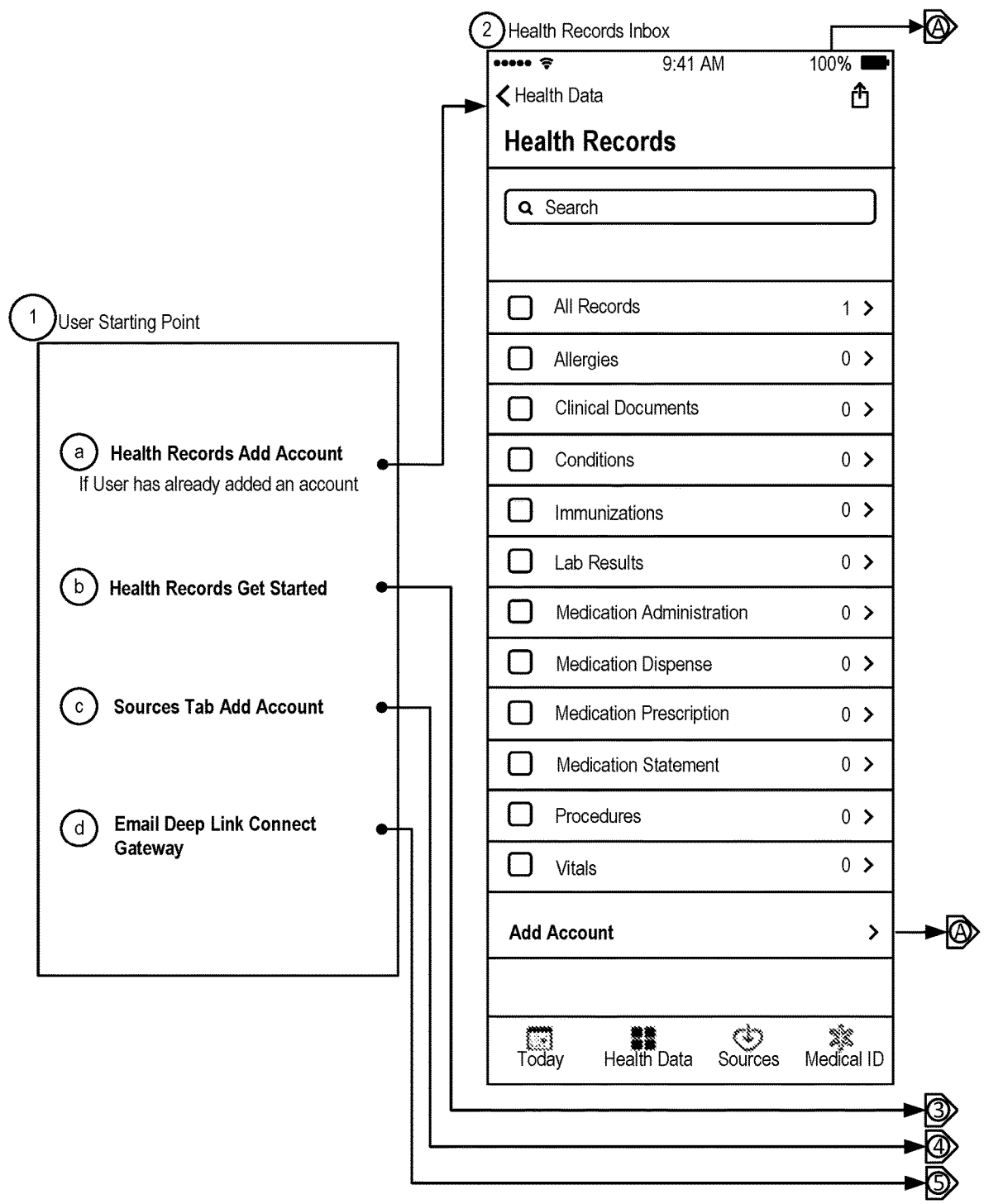
FIGS. 21-33 illustrate a series of processes, decision points, and user interface (UI) views relating to a user operating a health application of a user device to connect to a gateway of an electronic health record system for downloading health record data, according to various examples

FIG. 21 illustrates a user starting point (1), which identifies the processes (a)-(d), and UI view (2). The UI view (2) may be presented when the user first accesses the health application and has already added a health record (e.g., "(a) health records add account"). Currently, a single record has been added, which appears incomplete because all categories, except all records, include a zero value. As more health records are added, the number of record entries in the categories will begin to increase. The user may add more accounts by selecting the "add account" UI element. This selection results in decision point (A), illustrated in FIG. 23.

Figure 22:
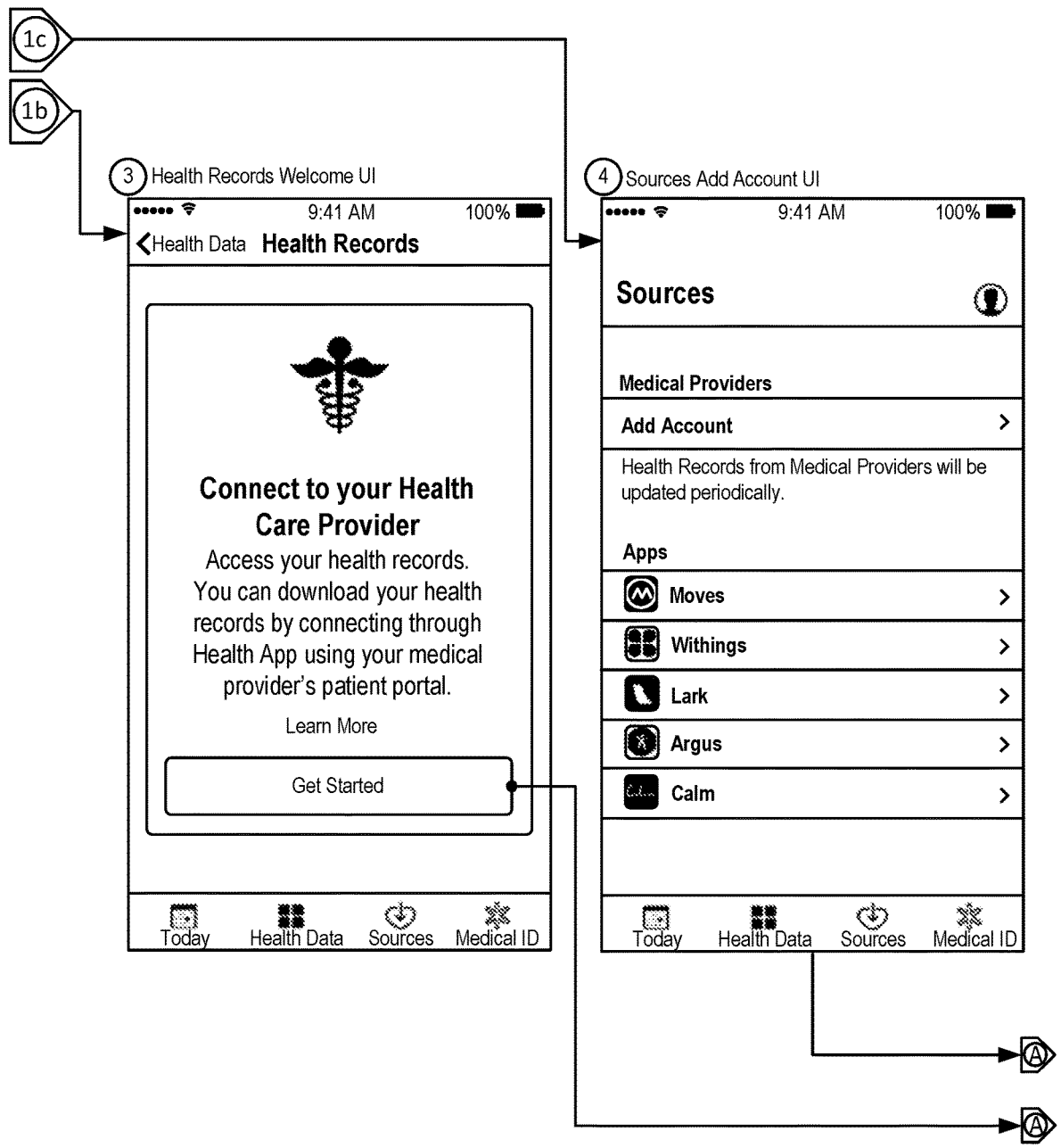

FIG. 22 illustrates user starting point (1) for processes (c) ("sources tab add account") and (b) ("health records get started") respectively as UI views (3) ("health records welcome UI") and (4) ("sources add account UI"). The UI view (3) may be presented when the user accesses the health application and selects an option for getting started with health records, which corresponds to the process (b). Thus, the UI view (3) may include a welcome message that includes information about accessing the user's health records, including downloading the health records to the user's user device using the user's patient portal. The user may begin the process for adding health records by selecting the "get started" UI element. This selection results in decision point (A), illustrated in FIG. 23.

The UI view (4) may be presented when the user accesses the health application and selections an option for adding an account, which corresponds to the process (c). Thus, the UI view (4) may include a UI element selectable to "add account" associated with a medical provider. The UI view (4) may also present a set of other applications relating to the health application. The user may begin the process for adding health records by selecting the "add account" UI element. This selection results in decision point (A), illustrated in FIG. 23.

Figure 23:
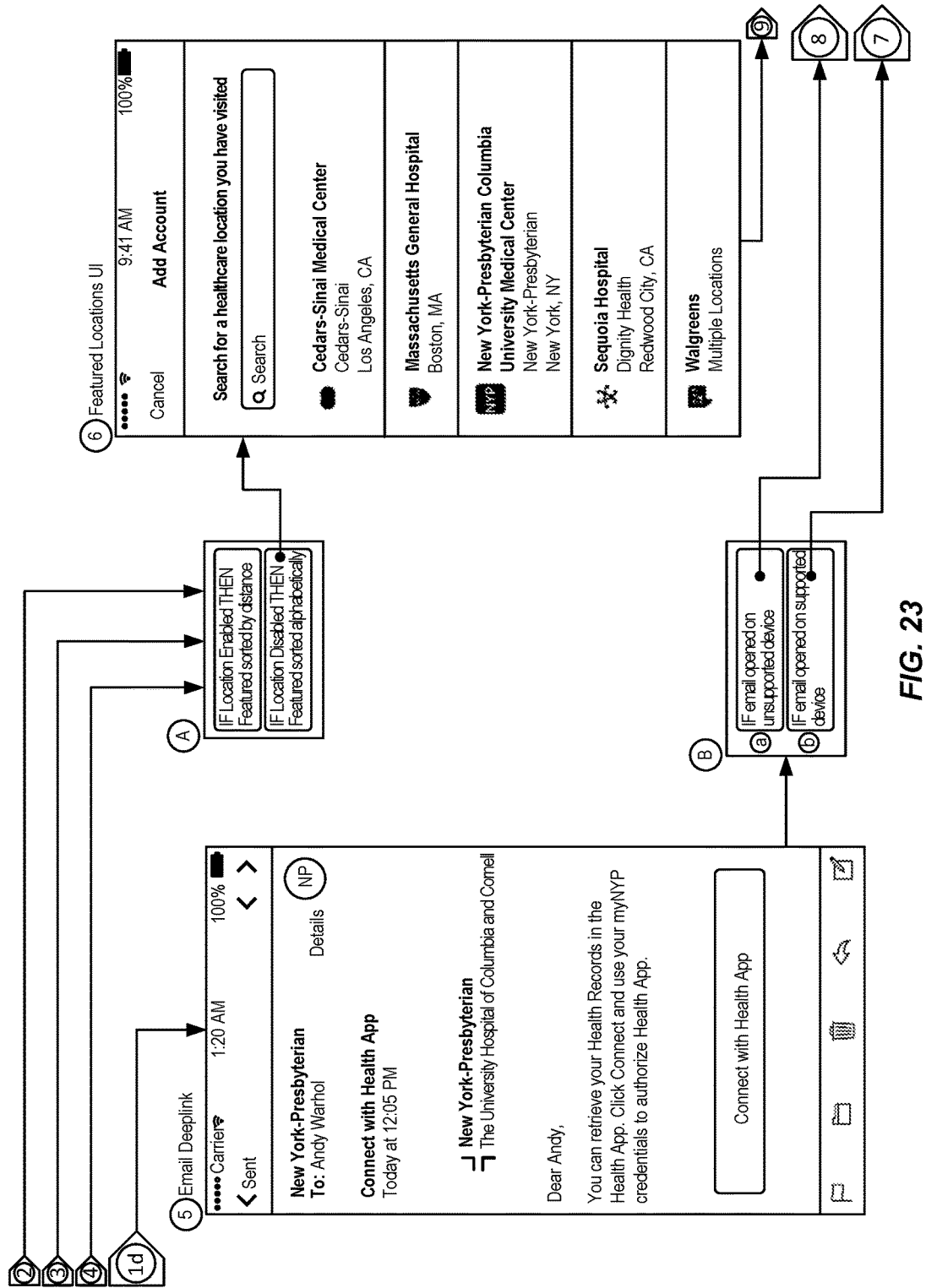
Figure 25:
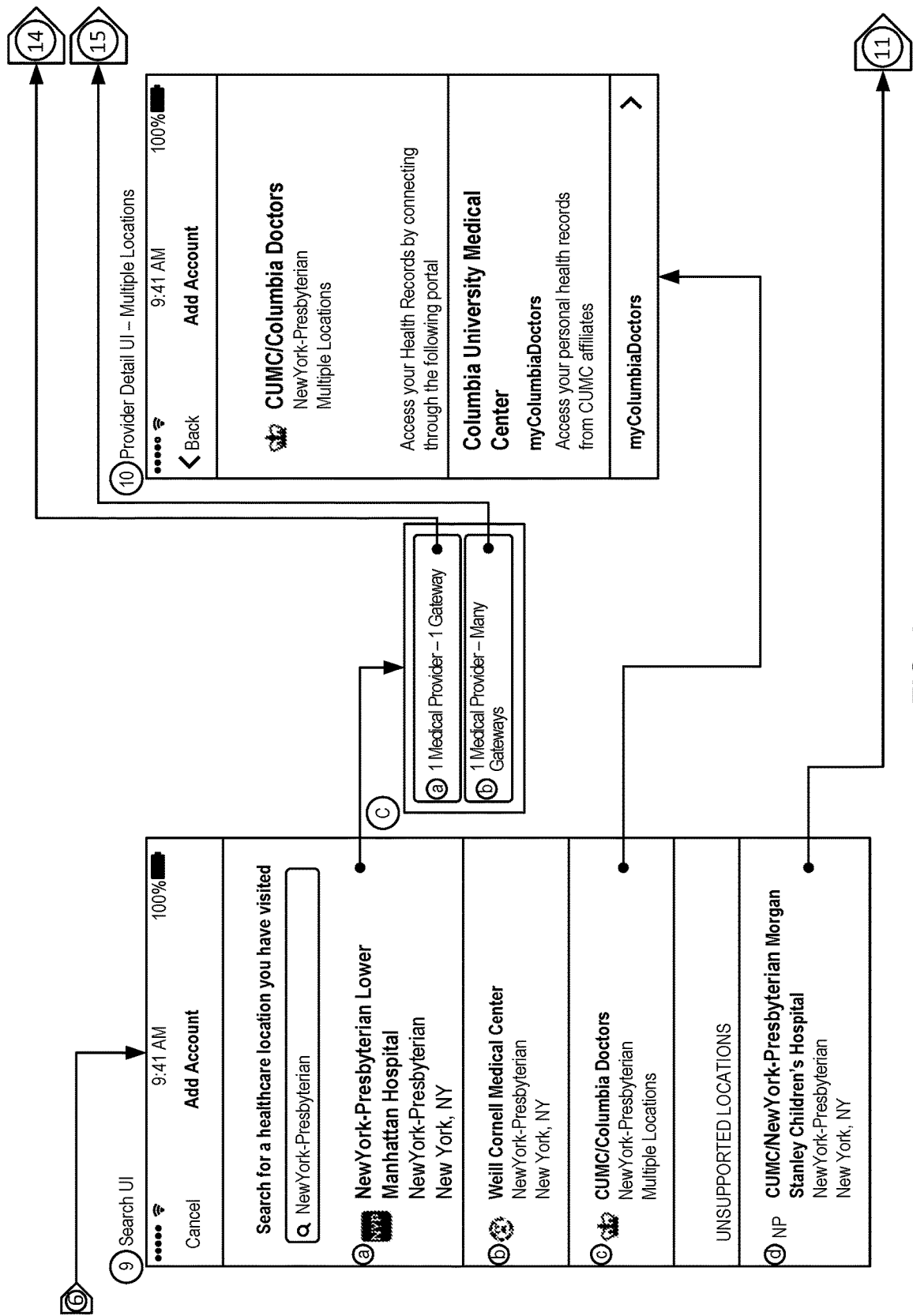

FIG. 23 illustrates the UI view (5) ("email deeplink"), the UI view (6) ("featured locations UI"), the decision point (A), and the decision point (B). At the decision point (A) it is determined whether location is enabled, e.g., has the user authorized the health application to access location data about the user device. If location is enabled, then in the UI view (6), the list of providers is served up based on location. If location is not enabled, then in the UI view (6), the list of providers is served up alphabetically (e.g., as illustrated in FIG. 23). The list of providers may be provided to the user device by the provider subscription system 112 in response to the user entering search terms into the search box in the UI view (6). The UI view (6) may include a prompt that reminds the user to search for healthcare locations that they have visited in the past. The list of providers included in the UI view (6) may include a variety of different healthcare providers. Selection of one of the providers included in the UI view (6) may result in presentation of the UI view (9), as illustrated in FIG. 25.

The UI view (5) may be presented when the user accesses the health application and selects an option for emailing a deep link to connect to the gateway, which corresponds to the process (d) from FIG. 21. Thus, the UI view (5) is an example, email application including an example email from a medical provider, "New York-Presbyterian." In some examples, the deep link may be generated by the provider subscription system and shared with the medical provider. In some examples, the medical provider generates the deep link. In any event, the deep link may be shared by the medical provider (e.g., via email or in some other way) with its patients as part of inviting the patients to connect to the medical provider. The body of the email may explain to the user how to connect and which credentials to use (e.g., "user your myNYP credentials"). These credentials may correspond to the NYP's patient portal. The UI view (5) includes a UI element selectable to begin the process of connection with the health application. This selection results in decision point (B), as illustrated in FIG. 23.

Figure 24:
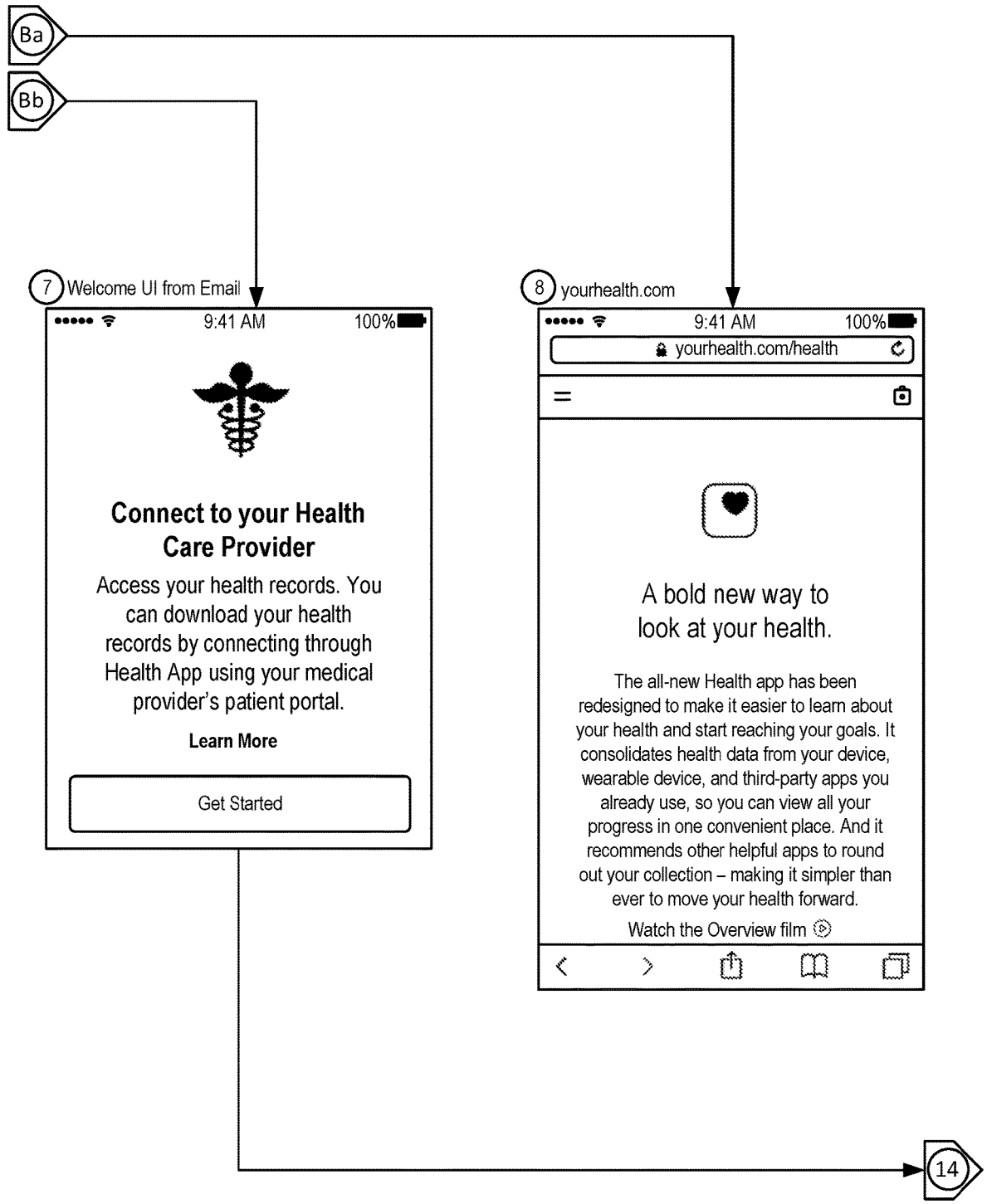

At the decision point (B) it is determined whether the email (e.g., illustrated in the UI view (5) is opened on a supported device. If the email is opened on a supported device (b) (e.g., a mobile user device that can be used to download the health record, as opposed to a desktop computer), then following (Bb), the UI view (7) is presented, as illustrated in FIG. 24. If the email is opened on an unsupported device (a), then following (Ba), the UI view (8) is presented, as illustrated in FIG. 24.

Figure 26:
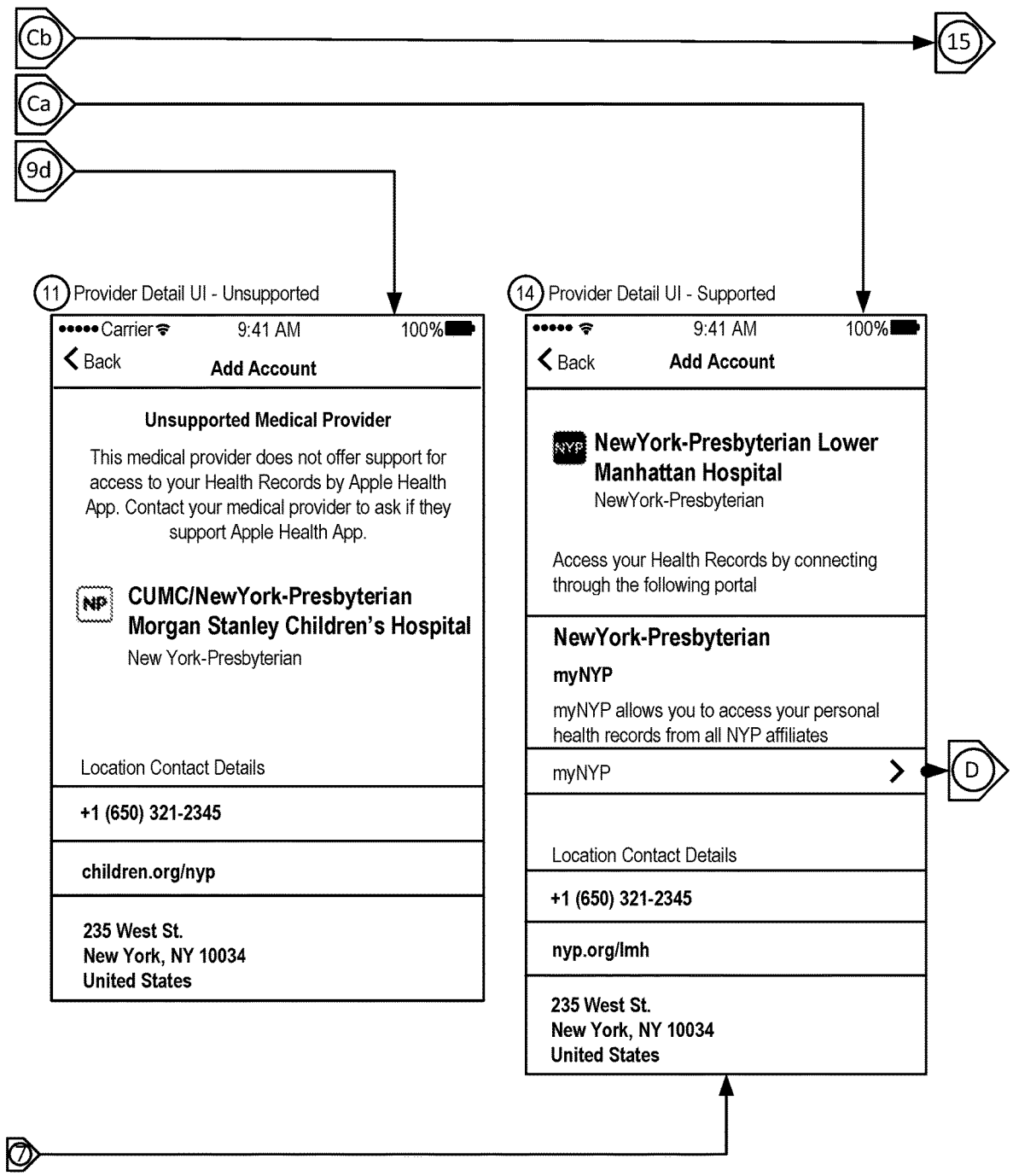

FIG. 24 illustrates the UI view (7) ("welcome UI from email") and the UI view (8) ("yourhealth.com"). The UI view (7) may be presented within the health application. The UI view (7) may include a welcome message that includes information about accessing the user's health records, including downloading the health records to the user's user device using the user's patient portal. The UI view (7) may also include a UI element selectable to get started accessing one's health records. This selection results in presentation of the UI view (14), as illustrated in FIG. 26.

The UI view (8) may be presented within a web browser on the user device. The UI view (8) may recommend that the user download the health application on her user device. For example, if the user opened the email from the UI view (5) on her laptop computer, the UI view (8) may be presented that explains the health application and prompts the user to open her user device and download or otherwise access the health application.

FIG. 25 illustrates the UI view (9) ("search UI"), the UI view (10) ("provider detail UI—multiple locations"), and the decision point (C). The UI view (9) may be presented within the health application. The UI view (9) may include a list of medical providers based on the search query "NewYork-Presbyterian." The results are identified by (a), (b), (c), and (d). Each medical provider in the list may include details about the medical provider sufficient to enable the user to make an informed decision about each (e.g., decide which of the medical provider is the one at which she obtains care). Selection of the medical provider (a) ("NewYork-Presbyterian Lower Manhattan Hospital") results in the decision point (C).

Figure 27:
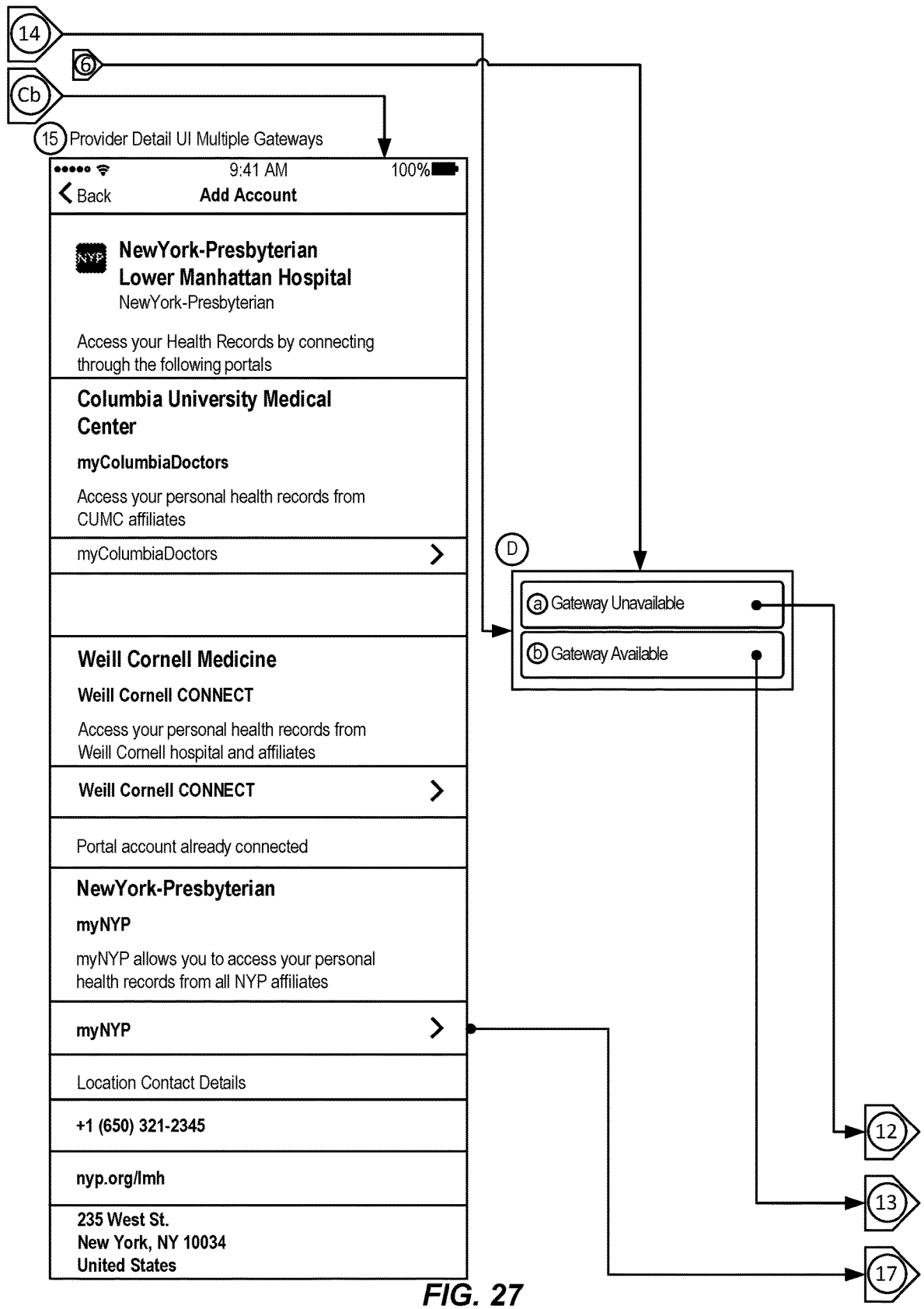

At the decision point (C) it may be determined whether the selected medical provider has one or many gateways. For example, some medical providers may have a single gateway (e.g., Walgreens) that supports many locations. Other medical providers may have multiple gateway that support a single location. The data structure 400 may be accessed at the decision point (C). If the medical provider has one gateway (a), then the UI view (14) is presented, as illustrated in FIG. 26 by following (Ca). If the medical provider has more than one gateway (b), then the UI view (15) is presented, as illustrated in FIG. 27 by following (Cb).

Selection of the medical provider (c) ("CUMC/Columbia Doctors") in the UI view (9) results in presentation of the UI view (10). The UI view (10) may be presented because the selected medical provider (c) is associated with more than one location. Thus, in the UI view (10), the user may be prompted to select the particular location affiliated with CUMC/Columbia Doctors where the user obtains care.

Selection of the medical provider (d) ("CUMC/New-York Presbyterian Morgan Stanley Children's Hospital") in the UI view (9) results in presentation of the UI view (11), as illustrated in FIG. 26 by following (9d). The UI view (11) may be presented when the selected location is unsupported by the health application.

FIG. 26 illustrates the UI view (11) ("provider detail UI—unsupported") and the UI view (14) ("provider detail UI—supported"). The UI view (11) may be presented within the health application after selection of an unsupported medical provider in the UI view (9), shown as (9d). The UI view (11) includes contact information for the unsupported medical provider and a message prompting the user to contact the unsupported medical provider and request support.

The UI view (14) may be presented within the health application after selection of a supported medical provider in the UI view (9) and which has a single gateway, shown as (Ca) from the decision point (C). The UI view (14) includes information about the medical provider and about a gateway of the medical provider that can be connected to. A UI element that identifies the "myNYP" patient portal is selectable to continue the process of connecting to the gateway. Selection of the UI element identifying the "myNYP" patient portal results in the decision point (D), as illustrated in FIG. 27.

Figure 29:
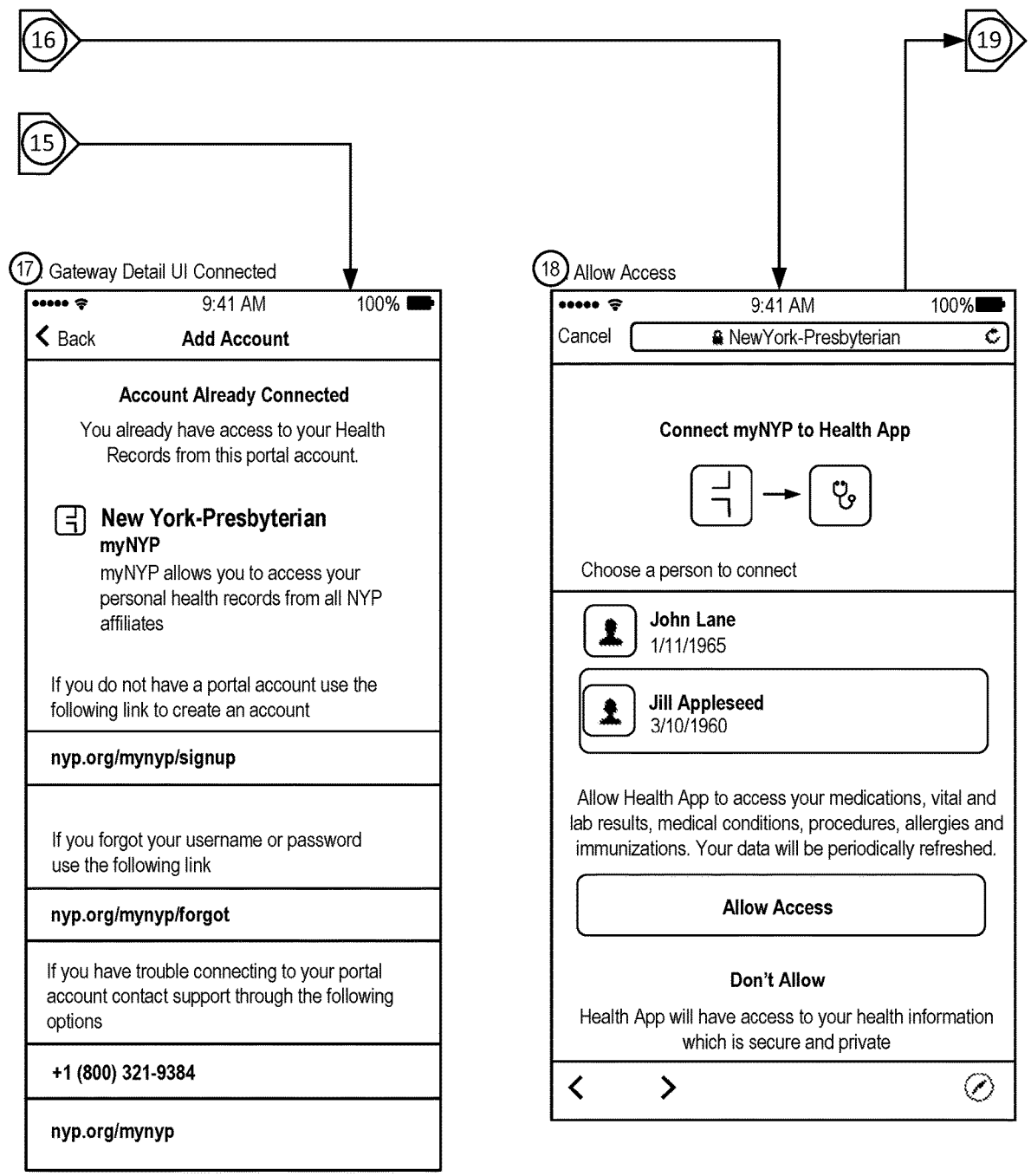

FIG. 27 illustrates the UI view (15) ("provider detail UI multiple gateways") and the decision point (D). The UI view (15) may be presented within the health application after selection of a supported medical provider in the UI view (9), which has a more than one gateway, shown as (Cb) from the decision point (C). Thus, the UI view (15) includes information about the three possible gateways (e.g., "myColumbiDoctors," "Weill Cornell CONNECT," and "myNYP") associated with the medical provider that can be connected to. In some examples, the user may be required to connect to all three gateways in order to obtain all of her health records from the medical provider. A UI element that identifies the "myNYP" patient portal is selectable to continue the process of connecting to the gateway. Selection of the UI element identifying the "myNYP" patient portal results in presentation of the UI view (17), as illustrated in FIG. 29.

Figure 28:
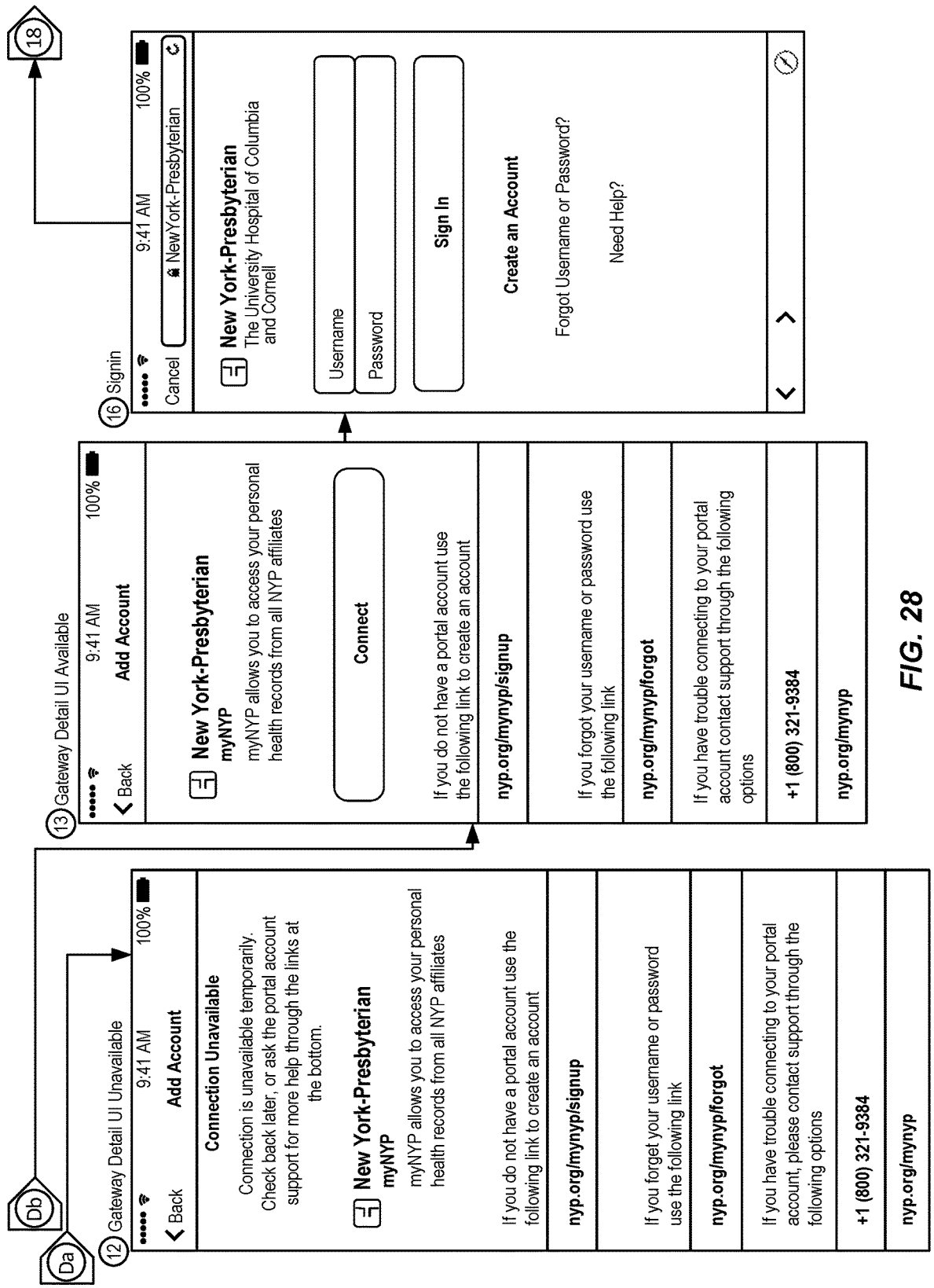

At the decision point (D) it may be determined whether the selected gateway is available. For example, some gateways, while registered in the provider database, may be unavailable during certain periods of time. A record associated with the gateway in the provider database may indicate availability of the gateway. In some examples, periodic testing of the gateway may be used to update the record (e.g., from available to unavailable). If the gateway is unavailable (a), then the UI view (12) is presented, as illustrated in FIG. 28 by following (Da). If the gateway is available (b), then the UI view (13) is presented, as illustrated in FIG. 28 by following (Db).

FIG. 28 illustrates the UI view (12) ("gateway detail UI unavailable"), the UI view (13) ("gateway detail UI available"), and the UI view (16) ("sign in"). The UI view (12) may be presented within the health application after it is determined at the decision point (D) that the gateway is unavailable. Thus, the UI view (12) includes a message informing the user that a connection is unavailable because the gateway is unavailable. The UI view (12) may also include links and/or contact information for the gateway and/or medical provider associated with the gateway. In this manner, the user may contact the medical provider directly to resolve the issue.

The UI view (13) may be presented within the health application after it is determined at the decision point (D) that the gateway is available. Thus, the UI view (13) includes a UI element (e.g., connect button) selectable by the user to connect to the available gateway. If the user has made it this far in the process, but has forgotten her password or would like to sign up for the patient portal, the user may click on links provided in the UI view (13). In some examples, this information presented (e.g., messages and links) may be gathered as described with reference to FIGS. 5-17. If the user selects the connect button, the UI view (16) may be presented within the health application. The UI view (16) may include fields for the user to input credentials including a username and password. These credentials may be specific to the gateway to which the user is connecting (e.g., myNYP associated with New-York Presbyterian—The University Hospital of Columbia and Cornell). A UI element that allows the user to sign in (e.g., the sign in button) is selectable to continue the process of connecting to the gateway. Selection of the sign in button results in presentation of the UI view (18), as illustrated in FIG. 29.

FIG. 29 illustrates the UI view (17) ("gateway detail UI connected") and the UI view (18) ("allow access"). The UI view (17) may be presented within the health application after selection of the "myNYP" item in the UI view (15). The UI view (17) may include a message informing the user that a connection has already been made between this gateway and the user device. The UI view (18) may be presented within the health application after selecting the sign in button in the UI view (16). The UI view (18) may include a prompt about connecting the user device to the gateway. When more than one users are associated with the user device and/or the gateway, the UI view (18) may be used to select the appropriate user (e.g., John Lane or Jill Appleseed). A UI element that allows the user to grant access (e.g., the allow access button) is selectable to continue the process of connecting to the gateway. Selection of the allow access button results in presentation of the UI view (19), as illustrated in FIG. 30.

Figure 30:
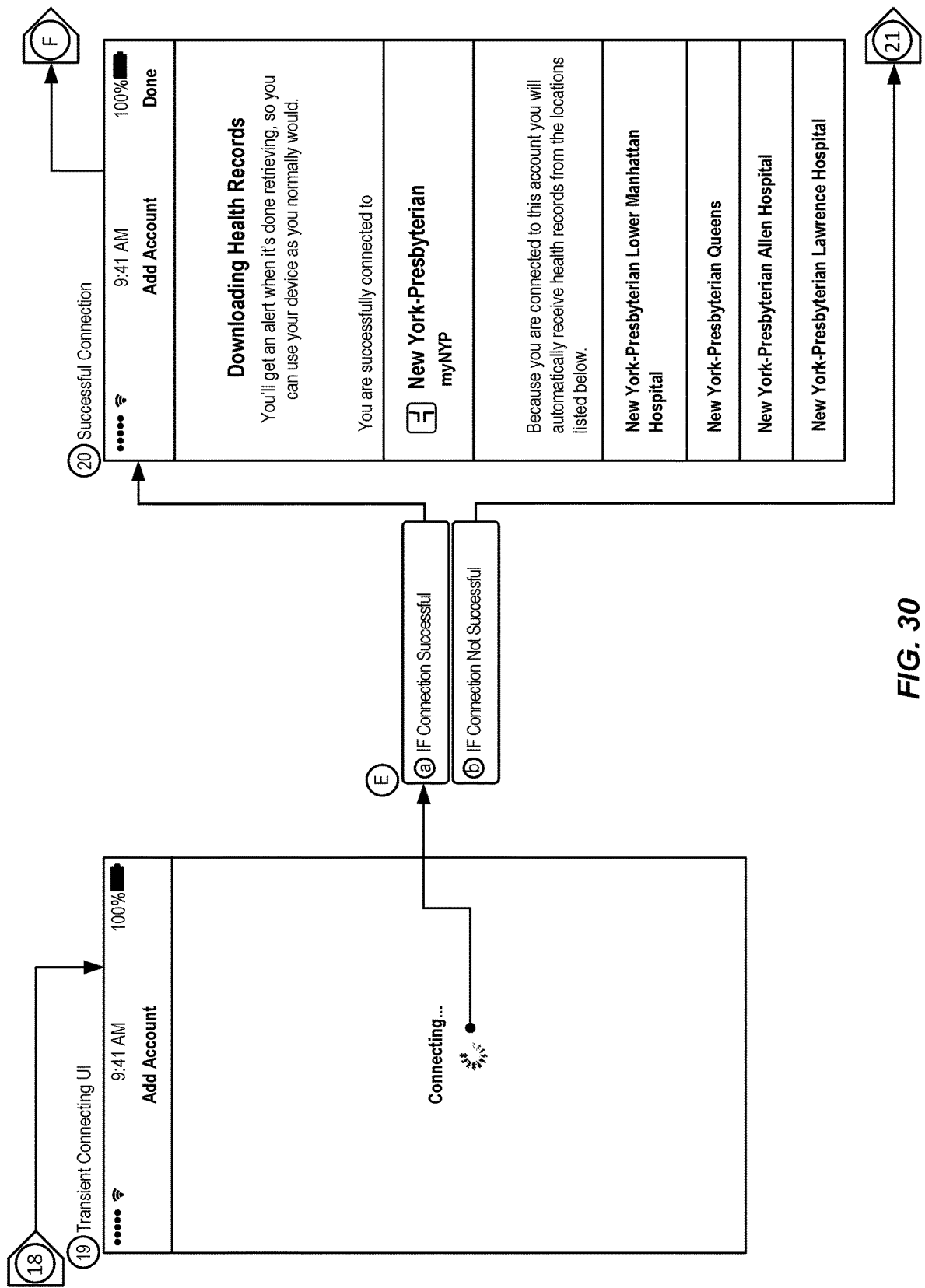
Figure 31:
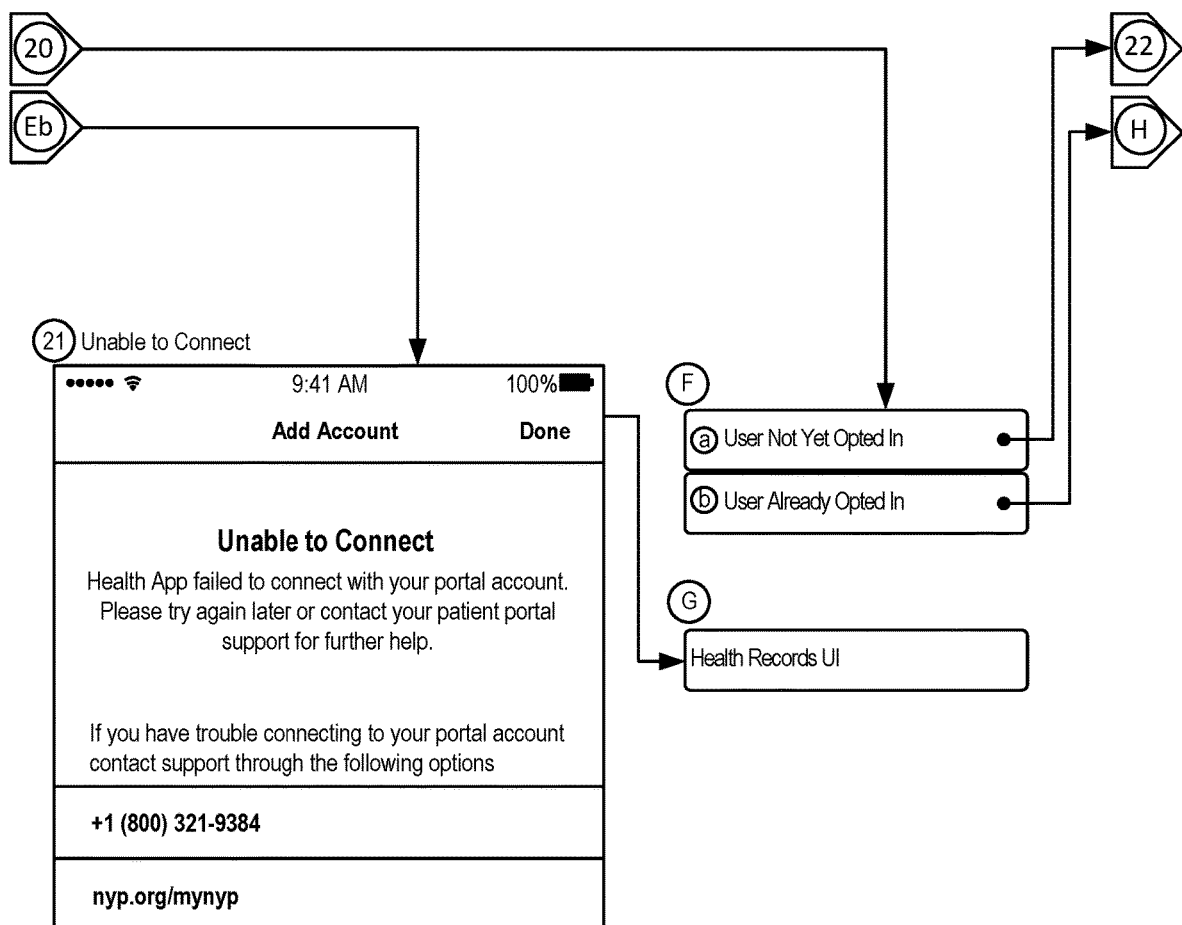

FIG. 30 illustrates the UI view (19) ("transient connecting UI"), the UI view (20) ("successful connection"), and the decision point (E). The UI view (19) may be presented within the health application after granting access by selecting the allowing access button in the UI view (18). At the decision point (E) it may be determined whether the connection to the gateway was successful. If the connection was successful (a), then the UI view (20) is presented, as illustrated in FIG. 30. If the connection was unsuccessful (b), then the UI view (21) is presented, as illustrated in FIG. 31 by following (Eb). The UI view (20) may be presented within the health application when it is determined at the decision point (E) that the connection was successful. The UI view (20) may include a message informing the user that she will get an alert once her records have been downloaded. From this point on, the downloading of records may be more or less automatic. In some examples, the user device may contact the gateway periodically to determine whether there are updates. In some examples, the gateway may send the updates periodically.

Figure 32:
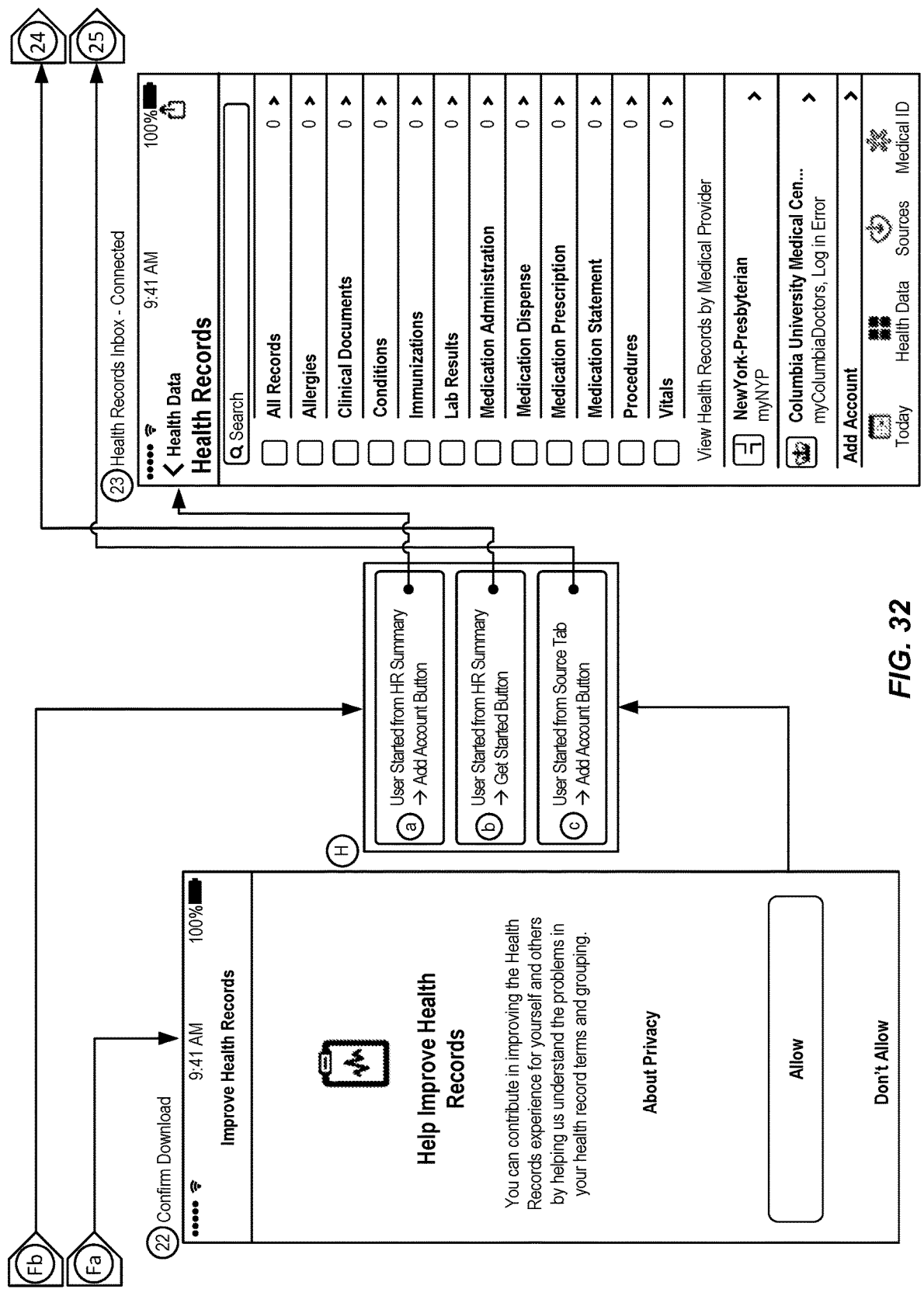

FIG. 31 illustrates the UI view (21) ("unable to connect") and the decision point (F). The UI view (21) may be presented within the health application when it is determined at decision point € that the user device was unable to connect to the gateway. Thus, the UI view (21) may include a message informing the user about the inability to connect to the gateway. At the decision point (F) it may be determined whether the user has opted in to sharing data with the subscription provider system. If the user has not yet opted in to sharing (a), then the UI view (22) is presented, as illustrated in FIG. 32 by following (Fa). If the user has opted in to sharing (b), then the decision point (H) is traversed, as illustrated in FIG. 32, by following (Fb).

FIG. 32 illustrates the UI view (22) ("confirm download"), the UI view (23) ("health record inbox—connected"), and the decision point (H). The UI view (22) may be presented within the health application when it is determined at the decision point (F) that the user has not yet opted in to sharing. In some examples, opting in to sharing may mean that the user agrees to share certain data with the operator of the provider subscription system. The system may use this data to improve the functionality of the health application. If the user agrees to share data, no identifying data will be shared with the system. Instead, the data will be anonymized and/or otherwise disconnected from the user. The UI view (22) may also include link to learn more about privacy.

As described above, one aspect of the present technology is the gathering and use of data available from various sources to improve the functioning of devices that index medical terms. The present disclosure contemplates that in some instances, this gathered data may include personal information data that uniquely identifies or can be used to contact or locate a specific person. Such personal information data can include demographic data, location-based data, telephone numbers, email addresses, health record data, home addresses, or any other identifying information.

The present disclosure recognizes that the use of such personal information data, in the present technology, can be used to the benefit of users. The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates examples in which users selectively block the use of, or access to, personal information data. That is, the present disclosure contemplates that hardware and/or software elements can be provided to prevent or block access to such personal information data. For example, in the case of medical data term sharing, the present technology can be configured to allow users to select to "opt in" or "opt out" of participation in the collection of personal information data during registration for services.

Therefore, although the present disclosure broadly covers use of personal information data to implement one or more various disclosed examples, the present disclosure also contemplates that the various examples can also be implemented without the need for accessing such personal information data. That is, the various examples of the present technology are not rendered inoperable due to the lack of all or a portion of such personal information data.

Figure 33:
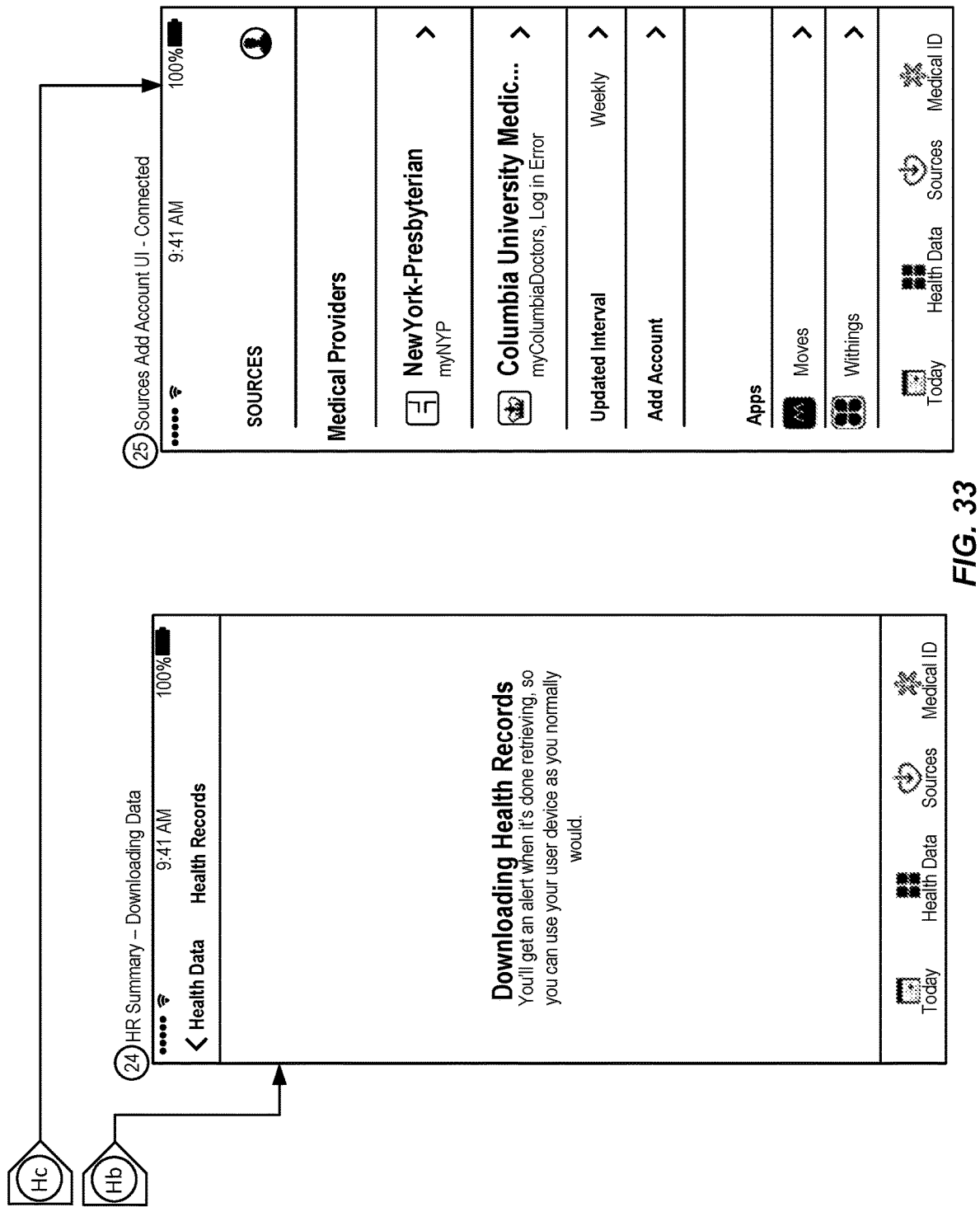

Regardless of the user's selection at the UI view (22), the decision point (H) may be considered. At the decision point (H) it may be determined, based on where the user first started the connection process, where to go next, e.g., (a), (b), or (c). If (a), the UI view (23) will be presented. If (b), the UI view (24) will be presented, as illustrated in FIG. 33. If (c), the UI view (25) will be presented, as illustrated in FIG. 33.

The UI view (23) may be presented within the health application when it is determined at the decision point (E) that the user started from HR summary—add account button. The UI view (23) may include a summary of all health records included on the user device and a list of those gateways that are connected (e.g., "New York Presbyterian" and "Columbia University Medical").

FIG. 33 illustrates the UI view (24) ("HR summary—downloading data") and the UI view (25) ("source add account UI—connected"). The UI view (24) may be presented within the health application when it is determined at the decision point (F) that the user started from HR summary—get started button. The UI view (25) may be presented within the health application when it is determined at the decision point (F) that the user started from the source tab—add account button. In the UI view (25), the user may select an update interval at which new records will be updated.

Figure 34:
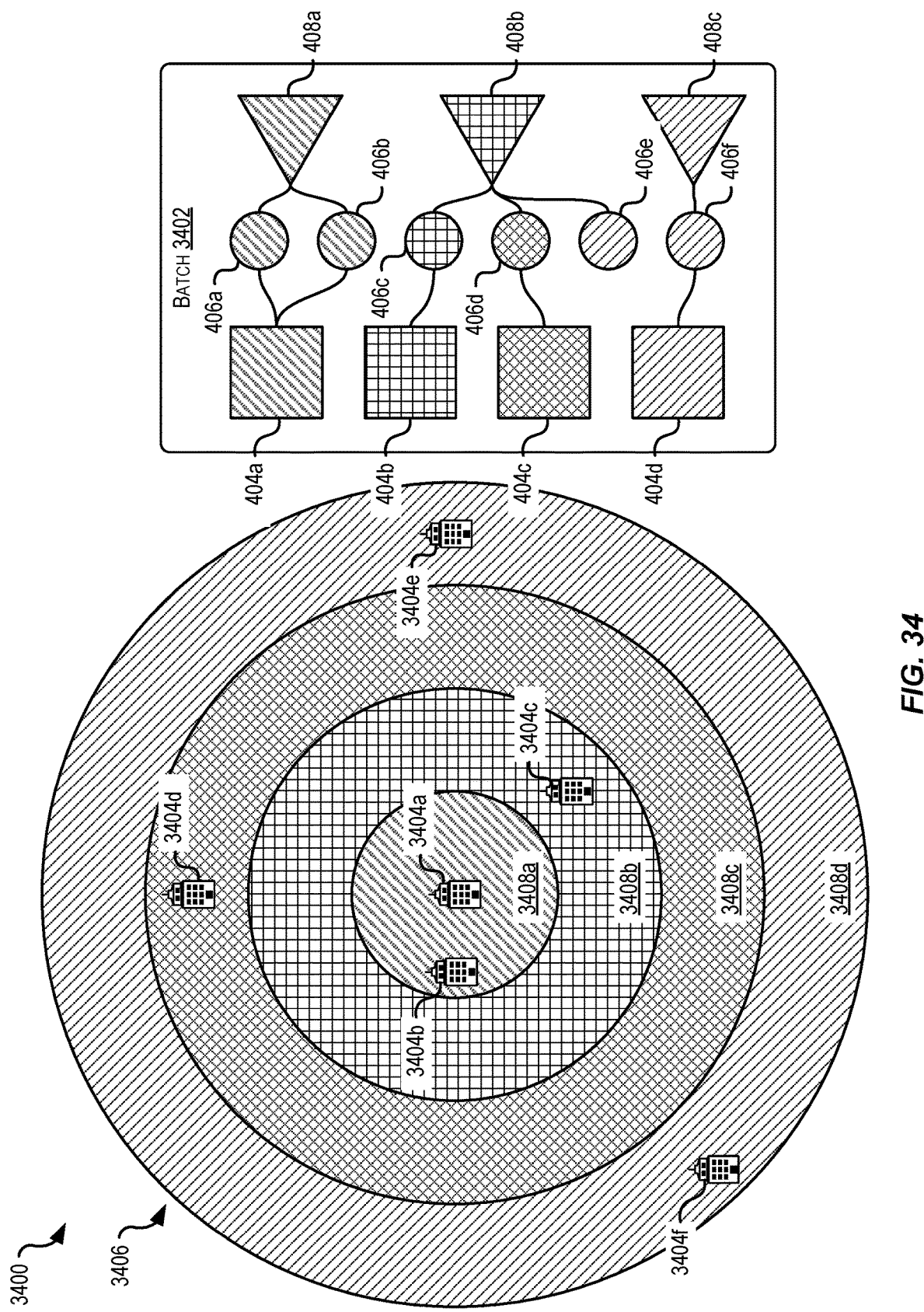
FIG. 34 illustrates a diagram depicting a geographic approach for constructing a batch of medical provider entities for enabling anonymized user searching of medical provider entities, according to at least one example.

FIG. 34 illustrates a diagram 3400 depicting a geographic approach for constructing a batch 3402 of medical provider entities for enabling anonymized user searching of medical provider entities, according to at least one example. The batch 3402 is similar to the data structure 400 in that it includes relationships between brand entities 404, location entities 406, and gateway entities 408. The batch 3402, however, may not be associated with an organization entity. This is because, instead of being organized by organization entity, the batch 3402 is organized geographically based on a starting medical provider, which in this example is medical provider 3404*a*, and unique to the medical provider 3404*a*. The batch 3402 may be identified by a unique batch identifier.

The medical provider 3404*a* is a physical location where patients can obtain care (e.g., an address). The medical provider 3404*a* may also be associated with a brand by which patients identify the medical provider 3404*a* (e.g., a name of the practice, name of an operating entity, etc.).

The diagram 3400 also includes a graphical depiction of an outward expanding geographic search 3406. The outward expanding geographic search 3406 may include a plurality of bands 3408*a*-3408*d*. Each of the plurality of bands 3408 is centered at the medical provider 3404*a*, expands outwardly, and thereby increases in diameter from 3408*a*-3408*d*. The area of the bands 3408 corresponds to actual land area (e.g., on a map). For example, the medical provider 3404*a* may be located at a city center and the bands 3408 may extend towards the suburbs (e.g., periphery of the city).

The outward expanding geographic search 3406 depiction corresponds to a process of building the batch 3402. For example, the process may begin by selecting the medical provider 3404*a*. In this example, the batch 3402 may be uniquely created for the medical provider 3404*a*. Later when users request information about the medical provider 3404*a* (e.g., as part of searching the provider database 118), the users will receive information about all or a portion of the entities in the batch 3402, including the medical provider 3404*a*. In this manner, the true identity of the medical provider 3404*a* may be obfuscated from the server that is enabling the searching.

Beginning with the medical provider 3404*a*, a first outward expanding search may be performed as represented by the band 3408*a*. During this first outward expanding search, the medical provider 3404*a* and a medical provider 3404*b* are identified. Once any medical provider 3404 has been identified, brand information, location information, and gateway information for the identified medical provider 3404 is added to the batch 3402 (e.g., a data object that includes the information represented by the batch 3402). Thus, as illustrated using similar object fill, the first outward expanding search represented by the band 3408*a* revealed brand entity 404*a*, location entities 406*a*, 406*b*, and gateway entity 408*a*. In this example, the two medical providers 3404*a*, 3404*b* correspond to the same brand entity (e.g., the brand entity 404*a*), each correspond to one of the location entities 406*a*, 406*b*, and correspond to the same gateway entity (e.g., the gateway entity 408*a*). Relationships between the brand entities 404, the location entities 406, and the gateway entities 408 are represented by connecting lines. These relationships may have been previously defined and/or may be defined using the techniques described herein.

The outward expanding search may be incrementally increased (e.g., increasing search radius by 1 mile) until threshold numbers of brand entities, location entities, and/or gateway entities have been achieved. The threshold numbers may be different values or the same values. Thus, in this example, three more searches are performed following the first search. These three other searches, discussed below, correspond to the bands 3408*b*, 3408*c*, and 3408*d*. Additional or fewer searches may also be performed depending on the implementation.

A second outward expanding search may be performed as represented by the band 3408*b*. During this second outward expanding search, a medical provider 3404*c* is identified. Once identified, brand information, location information, and gateway information are added to the batch 3402. Thus, as illustrated using a similar object fill, brand entity 404*b*, location entity 406*c*, and gateway entity 408*b* have been added to the batch 3402. In this example, the medical provider 3404*c* is represented by the brand entity 404*b*, the location entity 406*c*, and the gateway entity 408*b*.

A third outward expanding search may be performed as represented by the band 3408*c*. During this third outward expanding search, a medical provider 3404*d* is identified. Once identified, brand information, location information, and gateway information are added to the batch 3402. Thus, as illustrated using a similar object fill, brand entity 404*c* and location entity 406*d* have been added to the batch 3402. Because the gateway entity 408*b* used by the medical provider 3404*d* had already been identified, a new gateway is not added to the batch 3402. Instead, a relationship between the location entity 406*d* and the gateway entity 408*b* is created. In this example, the medical provider 3404*d* is represented by the brand entity 404*c*, the location entity 406*d*, and the gateway entity 408*b*.

A fourth outward expanding search may be performed as represented by the band 3408*d*. During this fourth outward expanding search, medical providers 3404*e*, 3404*f* are identified. Once identified, brand information, location information, and gateway information are added to the batch 3402. Thus, as illustrated using a similar object fill, brand entity 404d, location entities 406e, 406f, and gateway entity 408c have been added to the batch 3402. In this example, the medical provider 3404e is represented by the location entity 406e and the gateway entity 408b. The medical provider 3404f is represented by the brand entity 404d, the location entity 406f, and the gateway entity 408c.

Figure 35:
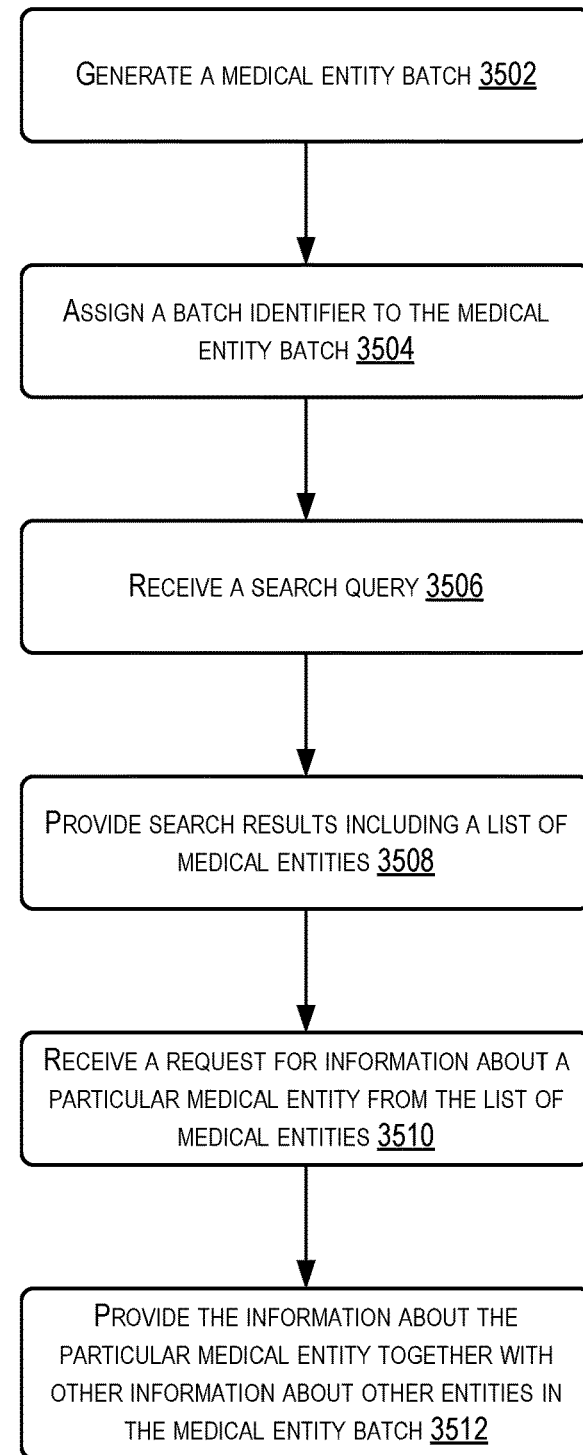
FIG. 35 illustrates an example flow chart showing a process for enabling anonymized user searching of medical provider entities, according to at least one example.

FIG. 35 illustrates an example flow chart showing the process 3500 for enabling anonymized user searching of medical provider entities, according to at least one example. The process 3500 may be performed by the provider subscription system 112

The process 3500 may begin at 3502 by generating a medical entity batch (e.g., the batch 3402). In some examples, the batch may include a brand entity set, a location entity set, and a gateway entity set. Generating the medical entity batch may include, e.g., as discussed with respect to FIG. 34, selecting a first location entity associated with a first geographic location, beginning, based at least in part on the first geographic location, an outward expanding geographic search for other entities, ceasing the outward expanding geographic search when a threshold number of entities has been identified for each of the brand entity set, the location entity set, and the gateway entity set.

In some examples, generating the entity batch is based at least in part on generating a plurality of other entity batches. In some examples, generating the plurality of other entity batches and the entity batch may include converting each entity identifier of each medical entity to an integer value in a range between one and a predefined number corresponding to a number of slots in each entity batch and assigning each medical entity to a respective entity batch based at least in part on the respective integer value, the respective integer value being equal to a respective batch identifier.

At 3504, the process 3500 may include assigning a batch identifier to the medical entity batch. In some examples, individual entities in the medical entity batch may be associated with respective entity identifiers.

At 3506, the process 3500 may include receiving a search query (e.g., from a user device). The search query may include one or more search terms.

At 3508, the process 3500 may include providing search results including a list of medical entities. The list may be provided to the user device based at least in part on the one or more search terms.

At 3510, the process 3500 may include receiving a request about a particular medical entity from the list of medical entities. This request may be received from the user device. The particular medical entity may belong to the medical entity batch. The request may include the batch identifier and a particular entity identifier identifying the particular medical entity.

At 3512, the process 3500 may include providing the information about the particular medical entity together with other information about other entities in the medical entity batch to the user device. In some examples, providing the information about the particular medical entity together with other information about other medical entities in the entity batch obfuscates an identity of the particular medical entity.

In some examples, the process 3500 may further include receiving a second request from the user device for other information about the particular medical entity. The second request may include the batch identifier and the particular entity identifier.

In some examples, the threshold number of entities is a different value for each one of the brand entity set, the location entity set, and the gateway entity set.

In some examples, at least one gateway entity of the gateway entity set is associated with more than one location entity of the location entity set.

In some examples, a provider database is provided and configured to store information about the medical entities. In this example, the process 3500 may further include, after assigning the batch identifier, storing information about the medical entity batch in association with the batch identifier in the provider database.

In some examples, the process 3500 may further include enabling the user device to establish a connection with a gateway entity associated with the particular medical entity. In some examples, the information about the particular medical entity comprises configuration information associated with the gateway entity. The configuration information may be useable by the user device to make one or more predefined method calls to the gateway entity.

Figure 36:
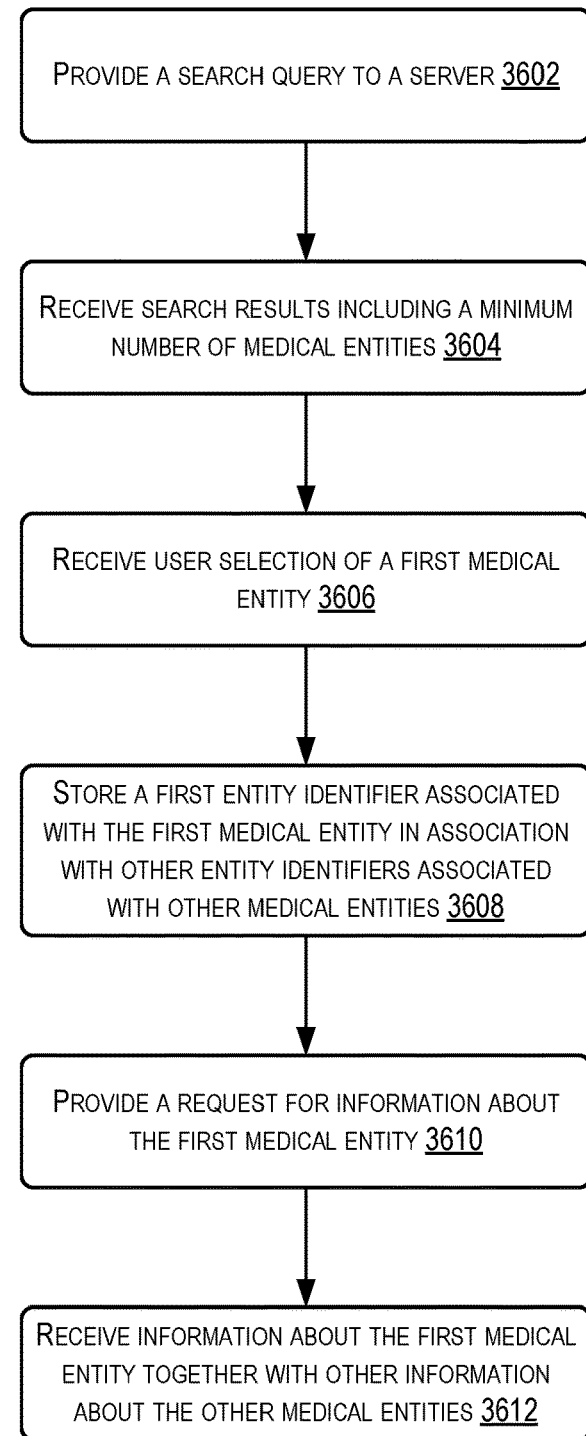
FIG. 36 illustrates an example flow chart showing a process for enabling anonymized user searching of medical provider entities, according to at least one example.

FIG. 36 illustrates an example flow chart showing the process 3600 for enabling anonymized user searching of medical provider entities, according to at least one example. The process 3600 may be performed by the user device 1400.

The process 3600 may begin at 3602 by providing a search query to a server. The search query may include one or more search terms. A user may input the search terms using any suitable input means.

At 3604, the process 3600 may include receiving search results including a minimum number of medical entities. In some examples, the search results may be received from a server (e.g., the provider subscription system 112). The search results may be selected based at least in part on the one or more search terms. In some examples, each medical entity of the medical entities is associated with an entity identifier.

At 3606, the process 3600 may include receiving user selection of a first medical entity from the minimum number of medical entities.

At 3608, the process 3600 may include storing a first entity identifier associated the first medical entity in association with other entity identifiers associated with other medical entities from the minimum number of medical entities.

At 3608, the process 3600 may include providing a request for information about the first medical entity. The request may be sent to the server and may include the first entity identifier and the other entity identifiers.

At 3610, the process 3600 may include receiving the information about the first medical entity together with other information about the other medical entities. In some examples, this information may be received from the server and in response to providing the request. In some examples, receiving the information about the first medical entity together with the other information about other medical entities obfuscates, from the server, an identity of the first medical entity as the medical entity that was subject to the user selection.

In some examples, the process 3600 may further include establishing a connection with a gateway entity associated with the first medical entity.

In some examples, the information about the first medical entity includes configuration information associated with the gateway entity. The configuration information may be useable by the user device to make one or more predefined method calls to the gateway entity to establish the connection with the gateway.

In some examples, storing the first entity identifier associated the first medical entity in association with the other entity identifiers associated with other medical entities is performed at least during a period of time when the connection with the gateway exists.

Figure 37:
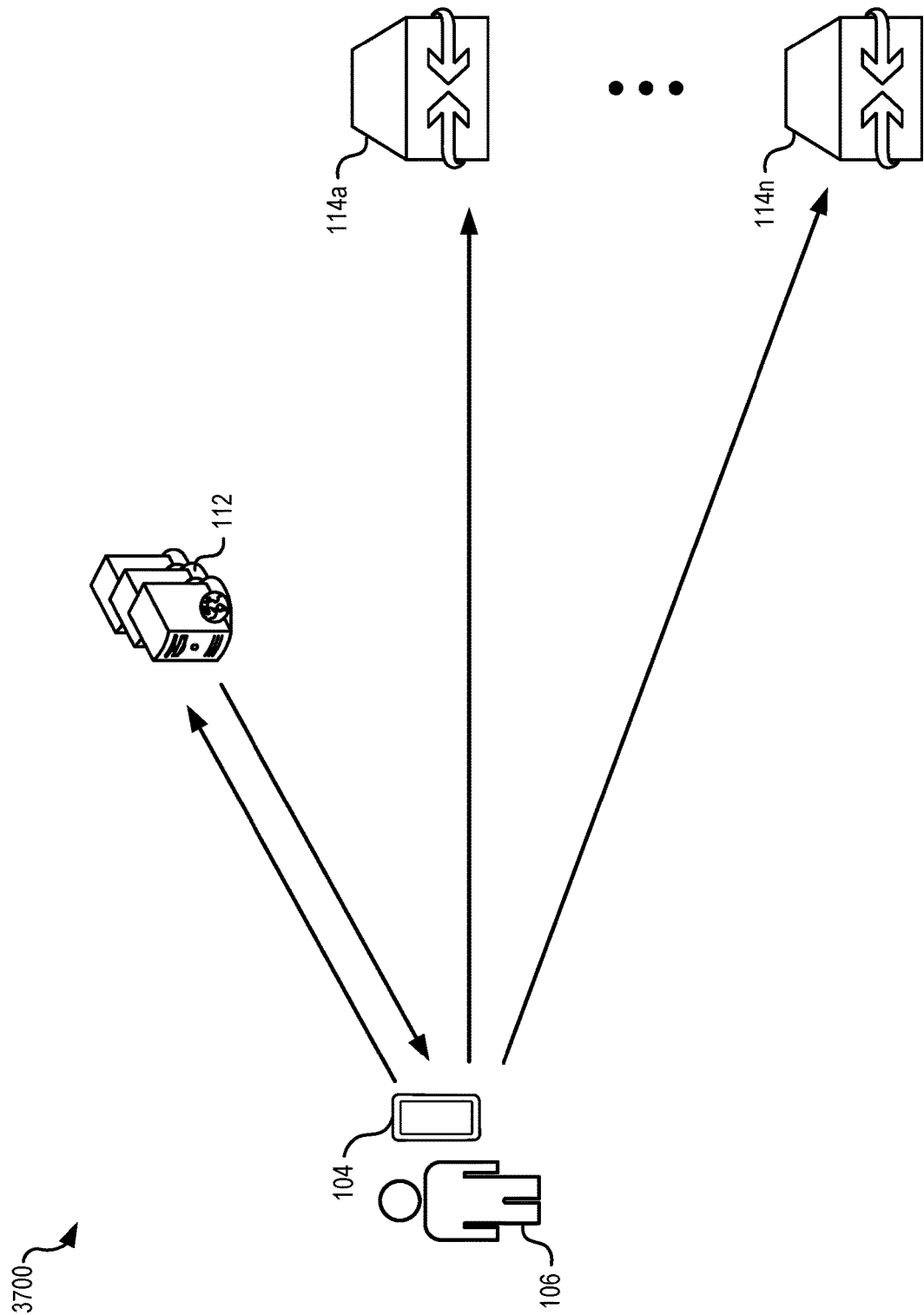
FIG. 37 illustrates a block diagram depicting a server-based approach for managing user device access to a plurality of electronic health record systems, according to at least one example.

FIG. 37 illustrates a block diagram 3700 depicting a server-based approach for managing user device access to a plurality of gateways of the EHR systems, according to at least one example. The diagram 3700 includes a server (e.g., the provider subscription system 112), a user device operated by a user (e.g., the user device 104 and the user 106), and a plurality of EHR systems 114a-114n (e.g., gateways entities 408a-408n). Using techniques described herein, a plurality of independent connections may be established between the user device 104 and the EHR systems 114a-114n. Using these connections, the user device 104 may download electronic health record data for the user 106. The EHR systems 114, the provider subscription system 112, and the user device 104 may all be operated by separate entities. In some examples, networking equipment at the EHR systems 114 may only be capable of handling a certain number of network request at any given time. Too many requests at any given time may cause the EHR systems 114 to malfunction or otherwise become unavailable. To address this concern, the provider subscription system 112 may manage when and how frequently the user 106 attempts to connect to the EHR systems 114. Such management may be based on specific characteristics of the EHR systems 114 and/or may be based on generic characteristics shared by more than one EHR system 114. For example, as part of adding the EHR systems 114 to the system operated by the provider subscription system 112, network capability configuration information may be gathered from the EHR systems 114. This information may later be used by the provider subscription system 112 to determine when and how frequently the user device 104 can contact the EHR systems 114. In some examples, the provider subscription system 112 may estimate characteristics of the EHR systems 114 to make this determination, which may be based on an update value.

Figure 38:
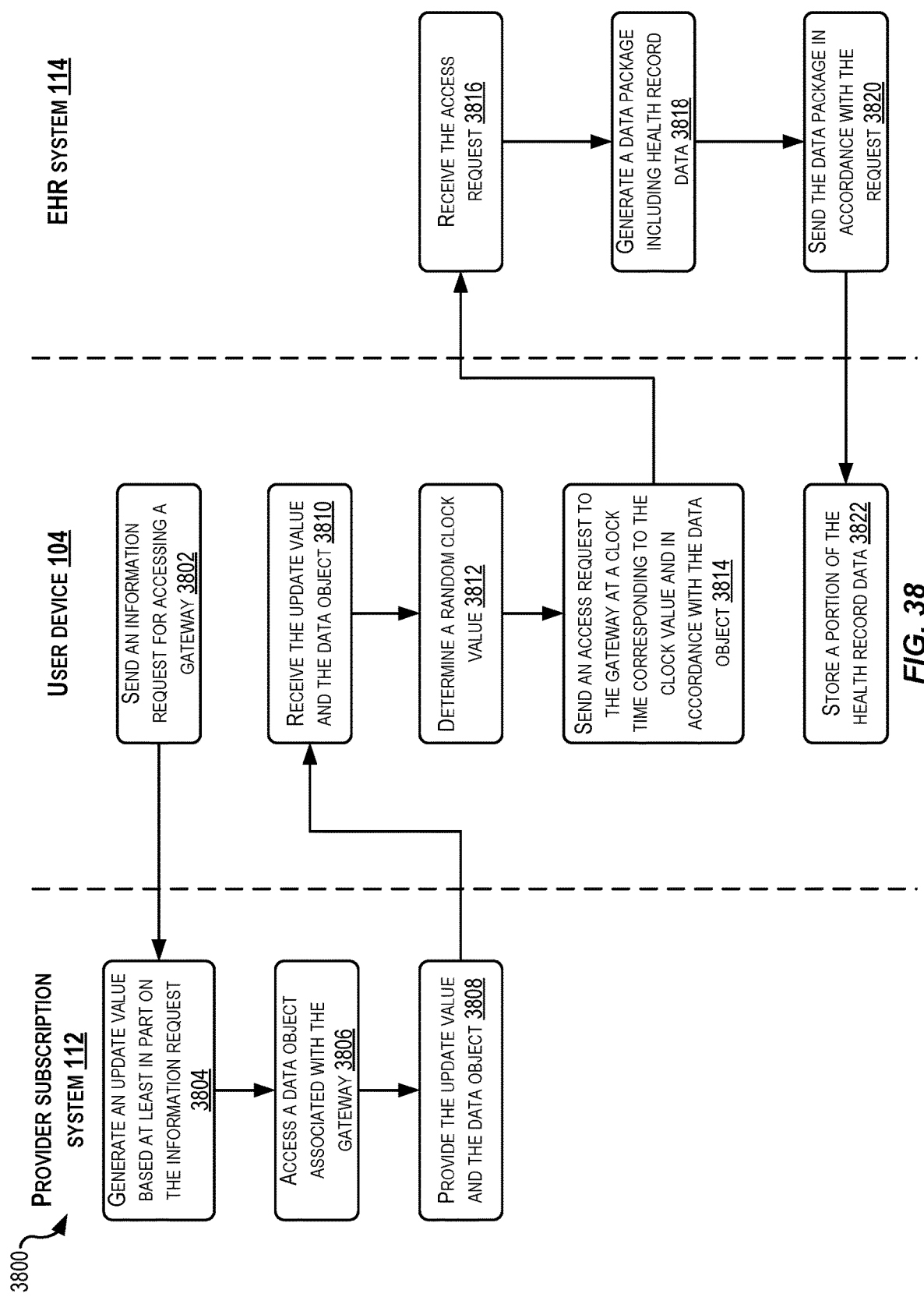
FIG. 38 illustrates an example flow chart showing a process for a server-based approach for managing access of a user device to a gateway of an electronic health record system, according to at least one example.

FIG. 38 illustrates an example flow chart showing the process 3800 for a server-based approach for managing access of a user device to a gateway entity, according to at least one example. The process 3800 may be performed by the provider subscription system 112, the user device 104, and/or the EHR system 114 (e.g., a gateway entity of the EHR system 114).

The process 3800 may begin at 3802 by sending an information request for accessing a gateway. This may be performed by the user device 104. The information request may be sent to a server (e.g., the provider subscription system 112). The information request may request information about accessing the gateway of the EHR system 114.

At 3804, the process 3800 may include generating an update value based at least in part on the information request. This may be performed by the provider subscription system 112. The update value may represent a time period (e.g., a hour, a day, a week, a month, etc.) and may be generated based at least in part on characteristics of the EHR system 114. In some examples, the time period is expressed in seconds. Relevant characteristics of the EHR system 114 may include those that are related to network load capabilities of the EHR system 114.

At 3806, the process 3800 may include accessing a data object associated with the gateway of the EHR system 114. This may be performed by the provider subscription system 112. The data object may include configuration information useable by the user device 104 for accessing the gateway. For example, the configuration information may include application programming interface (API) information that is particular to the gateway. Later, the user device 104 may use the API information for connecting to the gateway of the EHR system 114 and downloading health record data. The data object may include a universal user identifier for the gateway.

At 3808, the process 3800 may include providing the update value and the data object. This may be performed by the provider subscription system 112. In some examples, the update value and the data object are provided to the user device 104 in response to the information request.

At 3810, the process 3800 may include receiving the update value and the data object. This may be performed by the user device 104. The update value and the data object may be received from the provider subscription system 112.

At 3812, the process 3800 may include determining a random clock value. This may be performed by the user device 104. This may be performed by the user device 104. The random clock value may be a value that is between zero and the update value. The random clock value may correspond to a clock time within the time period. For example, the update value may be 86,400 seconds, which corresponds to a period of one hour. Given a current clock time of, e.g., 13:22:00, a random clock value may be determined that is within 86,400 seconds of 13:22:00. For example, if the random clock value were determined to be 43,200 seconds, then the clock time may be 13:52:00, e.g., half an hour later. The clock time may be used to schedule future requests (e.g., access requests that request downloading) to the gateway of the EHR system 114.

At 3814, the process 3800 may include sending an access request to the gateway at a clock time corresponding to the clock value and in accordance with the data object. This may be performed by the user device 104. The access request may request to download health record data maintained by the EHR system 114. In some examples, the data object may store configuration information for accessing the gateway of the EHR system 114. This configuration information may include API information, URLs, authentication information, etc.

At 3816, the process 3800 may include receiving the access request. This may be performed by the EHR system 114. Assuming that the access request was sent by the user device 104 at the clock time, the access request may be received by the EHR system 114 shortly after the clock time.

At 3818, the process 3800 may include generating a data package including health record data. This may be performed by the EHR system 114. The health record data may be generated using the Fast Healthcare Interoperability Resources (FHIR) standard or any other suitable standard such as those promulgated by the HL7 standard body and/or other standard bodies.

At 3820, the process 3800 may include sending the data package in accordance with the request. This may be performed by the EHR system 114. Sending the data package may include sending the data package to the user device 104. As described herein, the user device 104 may be associated with a user (e.g., a patient) to whom the health record data belongs.

At 3822, the process 3800 may include storing a portion of the health record data. This may be performed by the user device 104. The user device 104 may store the health record data in any suitable format. Part of storing the health record data may include indexing medical terms from the health record.

In some examples, the process 3800 may further include sending an additional information request from the user device 104 and to the provider subscription system 112 in preparation for sending an additional access request to the gateway of the EHR system 114. In this example, the process 3800 may further include receiving an additional communication from the provider subscription system 112. The additional communication may include a status indicator for the gateway. When the status indicator indicates that the gateway is available, the user device 104 may send additional access requests to the gateway of the EHR system 114. When the status indicator indicates that the gateway is unavailable, the user device 104 may refrain from sending the additional access requests.

Figure 39:
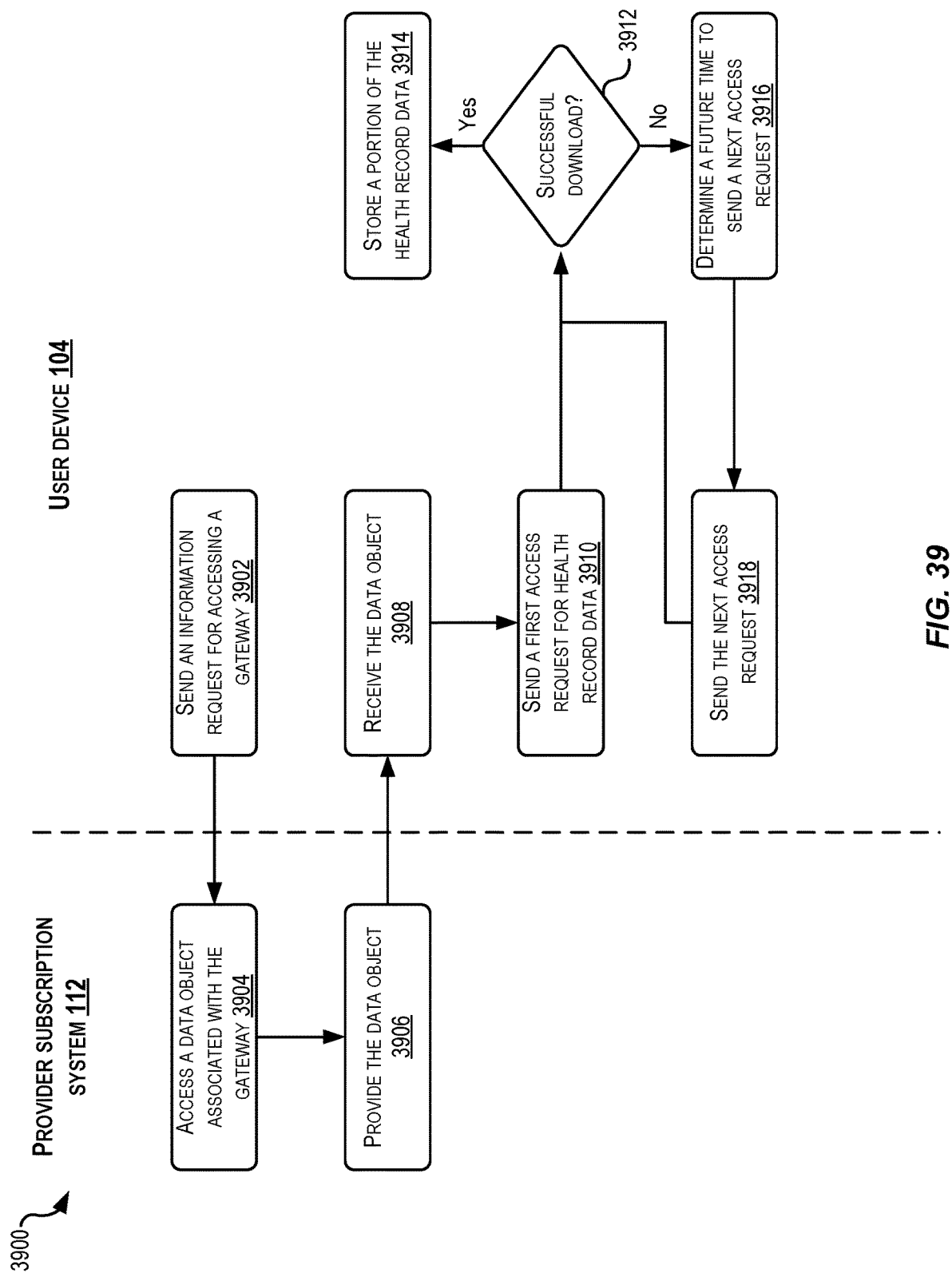
FIG. 39 illustrates an example flow chart showing a process for a user-device based approach for managing access to a gateway of an electronic health record system, according to at least one example.

FIG. 39 illustrates an example flow chart showing the process 3900 for a user-device based approach for managing access to a gateway entity, according to at least one example. The process 3900 may be performed by the provider subscription system 112 and the user device 104.

The process 3900 may begin at 3902 by sending an information request for accessing a gateway, e.g., of the EHR system 114. This may be performed by the user device 104. The request may be sent to a server, e.g., the provider subscription system 112. The information request may request information about accessing a gateway of an electronic health record system, e.g., the EHR system 114. In some examples, the information request includes information identifying a medical provider associated with the EHR system 114 and a plurality of other medical providers associated with at least one of the EHR system 114 or a different EHR system.

At 3904, the process 3900 may include accessing a data object associated with the gateway, e.g., of the EHR system 114. The data object may include access information and configuration information for the gateway.

At 3906, the process 3900 may include providing the data object. This may be performed by the provider subscription system 112. Providing the data object may include providing the data object to the user device 104.

At 3908, the process 3900 may include receiving the data object. This may be performed by the user device 104. The data object may be received in a communication from the provider subscription system 112. The configuration information may be useable by the user device 104 for accessing the gateway. For example, the configuration information may include application programming interface (API) information that is particular to the gateway.

At 3910, the process 3900 may include sending a first access request for health record data. This may be performed by the user device 104. The first access request may be sent to the provider subscription system 112. The first access request may, in particular, request downloading of health record data for a user of the user device 104 that is maintained by the EHR system 114.

At 3912, the process 3900 may determine whether the download was successful. This may include determining whether the user device 104 was able to connect to the gateway and/or whether the user device 104 received the requested health record data. In some examples, this may be based at least in part on receiving a connection timeout error from the gateway.

If the answer at 3912 is YES, the process 3900 proceeds to 3914 at which the process 3900 may include storing a portion of the health record data. In some examples, this may be performed by the user device 104. The user device may store the portion of the health record data using a first data model. Storing the portion of the health record data may include receiving a FHIR data package, unpacking the data, and storing the data.

If the answer at 3912 is NO, the process 3900 proceeds to 3916 at which the process 3900 may include determining a future time to send a next access request. This may be performed by the user device 104. The second access request may be an access request to be sent to the gateway. This determination may be based on a predefined route available on the user device 104. For example, the predefined routine may be configured to determine the conditions under which the user device 104 can attempt to connect to the gateway and/or other remote devices. In some examples, determining the future time may be based at least in part on characteristics of the user device. For example, the characteristics of the user device may include at least one of locked state, battery life, network connectivity, available processing capabilities, available storage, and/or any other suitable characteristic.

At 3918, the process 3900 may including sending the next access request. This may be performed by the user device 104. Sending the next access request may include sending to the gateway at the future time determined at 3916.

In some examples, the process 3900 may further include sending an additional information request to the provider subscription system 112 in preparation for sending an additional access request to the gateway. In this example, the process 3900 may further include receiving an additional communication from the provider subscription system 112. The additional communication may include a status indicator for the gateway. In this example, the process 3900 may further include refraining from sending the additional access request when the status indicator indicates that the gateway is unavailable. In this manner, the user device 104 may check in with the provider subscription system 112 to obtain updated status information for the gateway. This may minimize the situation in which the user device 104 attempts to contact the gateway, but cannot obtain information because the gateway is unavailable. If the gateway is available, then the user device 104 may contact the gateway.

Figure 40:
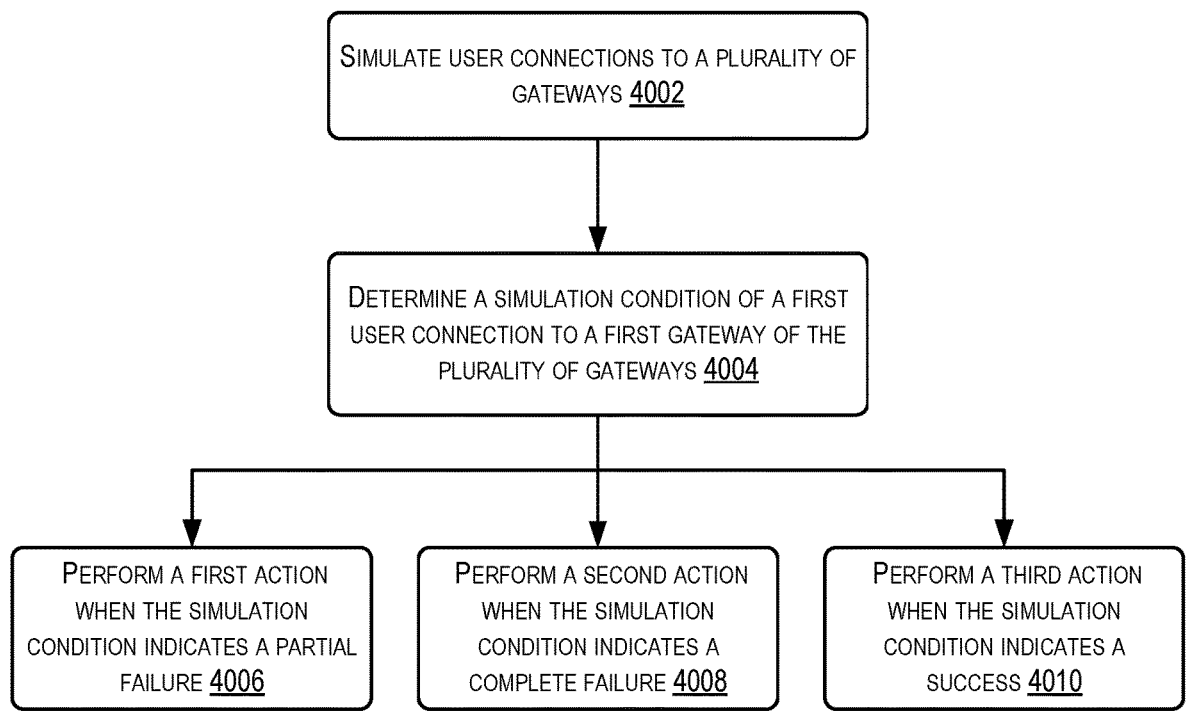
FIG. 40 illustrates an example flow chart showing a process for simulating user connections to gateways of electronic health record systems, according to at least one example.

FIG. 40 illustrates an example flow chart showing the process 4000 for simulating user connections to gateways of electronic health record systems, according to at least one example. The process 4000 may be performed by the provider subscription system 112.

The process 4000 may begin at 4002 by simulating user connections to a plurality of gateways. The simulation may be performed during a first period. The plurality of gateways may be associated with a plurality of electronic health record systems configured to maintain electronic health records for a plurality of users (e.g., patients). In some examples, simulating the user connections to the plurality of gateways may include using test user credentials to connect to test user profiles maintained by the plurality of EHR systems. The process 4000 may also include texting the gateway.

At 4004, the process 4000 may include determining a simulation condition of a first user connection to a first gateway of the plurality of gateways. The simulation condition may be identified while simulating the user connections to the plurality of gateways at 4002. The simulation condition includes at least one of a partial failure condition, a complete failure condition, or a success condition.

At 4006, the process 4000 may include performing a first action when the simulation condition indicates a partial failure. The first action may include simulating a second user connection to the first gateway during a second period. The first action may also include determining that the first gateway is inactive based at least in part on the second user connection failing during the second period. The first action may also include notifying a set of user devices that the first gateway is inactive. For example, the provider subscription system 112 may maintain a registry of user devices that maintain connections to the first gateway. Using this registry, the provider subscription system 112 may send a status message to the user devices. In some examples, the notifying the user devices may include publishing a status of the first gateway to a network location accessible by the user devices. For example, the provider subscription system 112 may update a record in the provider database 118 in which the information about the first gateway is saved. When the user devices "check in" with the provider subscription system 112 prior to connecting to the first gateway, the provider subscription system 112 can share the updated status information.

At 4008, the process 4000 may include performing a second action when the simulation condition indicates a complete failure. In this example, the second action may include notifying the set of user devices that the first gateway is inactive without simulating the second user connection. For example, the simulation condition may be so severe that the user devices should not even try to connect to the first gateway. Notifying the set of user devices may be performed as discussed with reference to block 4006.

At 4010, the process 4000 may include performing a third action when the simulation condition indicates a success. In this example, the third action may include enabling the set of user devices to connect to the first gateway. This may include updating an availability status of the gateway and allowing the user devices to access the availability status. In some examples, the third action may include enabling the set of user devices to connect to the first gateway in accordance with an update value. The update value may be defined as a future time window in which the set of user devices randomly connect to the first gateway.

Figure 41:
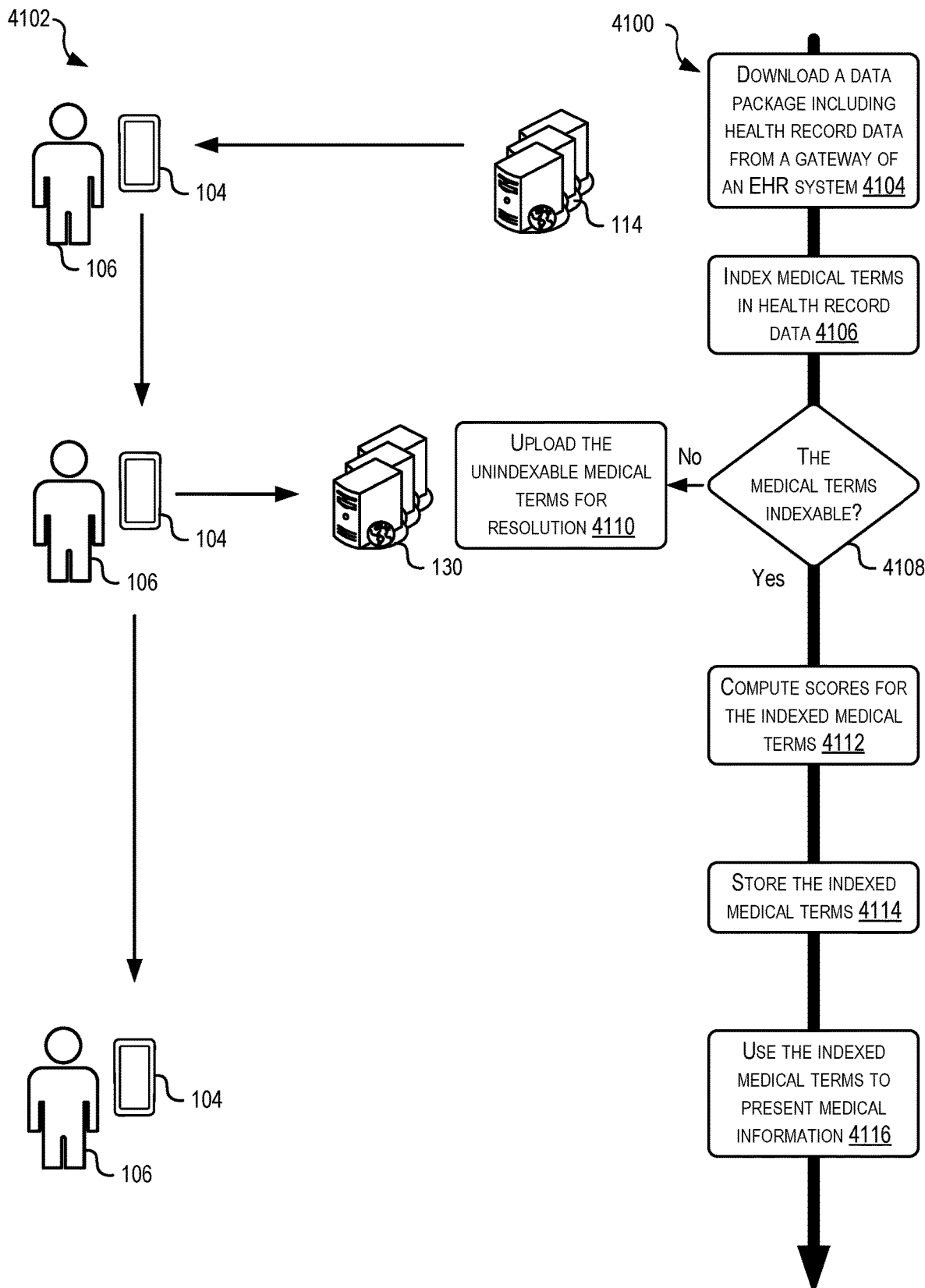
FIG. 41 illustrates a block diagram and a flow chart for indexing medical terms from an electronic health record, according to at least one example.

FIG. 41 illustrates a block diagram 4102 and a flow chart illustrating the process 4100 for indexing medical terms from an electronic health record, according to at least one example. The block diagram 4102 may include the user device 104, the EHR system 114, and the terminology management system 130. In some examples, the terminology management system 130 performs at least a portion of the process 4100. For example, the terminology management system 130 may index terms in a similar manner as the user device 104. In some examples, the terminology management system 130 may obtain access to many electronic health records (e.g., from a clinical data warehouse or other storage location). Using the electronic health records, the terminology management system 130 can build the term base 132.

The process 4100 may begin at 4104 by downloading a data package including health record data from a gateway of the EHR system 114. This may be performed by the user device 104. The health record data may be in any suitable format including, for example, the FHIR® standard, Clinical Documentation Architecture (CDA®), other standards promulgated by the Argonaut® project, or any other suitable standard. The health record data may include a personal electronic health record of a patient associated with a medical provider that is associated with the EHR system 114. In some examples, the personal electronic health record represents a portion of the user's 106 personal health record. Downloading the data package may include storing the electronic health record data according to a first data model.

At 4106, the process 4100 may include indexing medical terms in the health record data. This may be performed by the user device 104. The medical terms may be text in the health record data that describes aspects of the user's 106 health. For example, the medical terms may be text strings that describe a visit to a doctor, a prescription, results from a lab test, results from an imagery test, vital sign data, and any other suitable structure or unstructured data item from the electronic health record. As an additional example, the medical terms may be industry standard codes (e.g., RxNorm™, LOINC®, SNOMED™, and other suitable standard codes). Indexing the medical terms may include generating a medical term expression for the medical terms. The medical term expression is composed of medical term primitives that represent parts of the medical term. When a medical term is indexed, the corresponding medical term expression can be saved off and used for many different purposes described herein. Other information can be saved off that allows reproduction of the original medical term based on the medical term expression. Indexing medical terms will be described in more detail herein (e.g., FIG. 43-44). In some examples, the medical term expression may be generated using an industry standard code At 4108, the process 4100 may include determining whether the medical terms are indexable. This may be performed by the user device 104. A term is indexable if the user device can generate a medical term expression for the medical term. If medical terms are unidexable, at 4110, the process 4100 may include uploading the unidexable medical terms for resolution. This may include uploading the unidexable medical terms to the terminology management system 130. Receipt of the unidexable medical terms by the terminology management system 130 may trigger a workflow for resolving the medical terms. This workflow may include presenting the medical terms to medical professionals to determine a meaning for each of the medical terms. In some examples, the medical professionals may compare the medical terms with the proposed indexed terms to see if an association is improper.

Once the terminology management system 130 has resolved the unidexable medical terms, these terms may be send to the user device 104 using the updater service 204. For example, the updater service 204 may send the resolved terms as an over-the-air update to the user device 104. The user device 204 may then add the resolved terms to the term base 214. In some examples, the resolved terms may be provided to the user device 104 as part of an operating system update. In this example, the user may perform some action to initiate the operating system update. In the over-the-air update example, the updates may happen in the background when certain device conditions are met (e.g., connected to a WiFi network, plugged in, etc.), but without the user having to perform an action.

If the term is indexable, the process 4100 may proceed to 4112, at which, the process 4100 may include computing scores for the indexed medical terms. This may be performed by the user device 104 as part of a finalization process. The scores may represent how well the terms were indexed. The scores may include a completion score representing how well a particular medical term corresponds to an ideal medical term. The completion score may be based at least in part on a medical category to which the indexed medical term belongs. The scores may also include a coverage score representing a ratio of how much of the particular medical term was indexed (e.g., 75% of the words from the particular medical term are represented by the indexed medical term). The scores for the indexed medical terms may be shared with the terminology management system 130.

At 4114, the process 4100 may include storing the indexed medical terms. This may be performed by the user device 104. The indexed terms may be stored in a term base according to a second data model that is different from the first data model.

At 4116, the process 4100 may include using the indexed medical terms to present medical information. This may be performed by the user device 104. This may include presenting the medical information in a uniform or otherwise normalized manner, sorting and organizing a personal health record, searching other databases for medical data, supplementing the personal health record with metadata that enhances the user experience of interacting with her personal health record. For example, medical terms that are sourced from many different medical providers can be indexed. To achieve uniformity in how the data is organized and presented, the indexed medical terms can be used. Doing so essentially allows the user device 104 to compare raw medical terms from the different medical providers to determine that the medical providers are referring to the same thing, even though they may be using different language.

Figure 42:
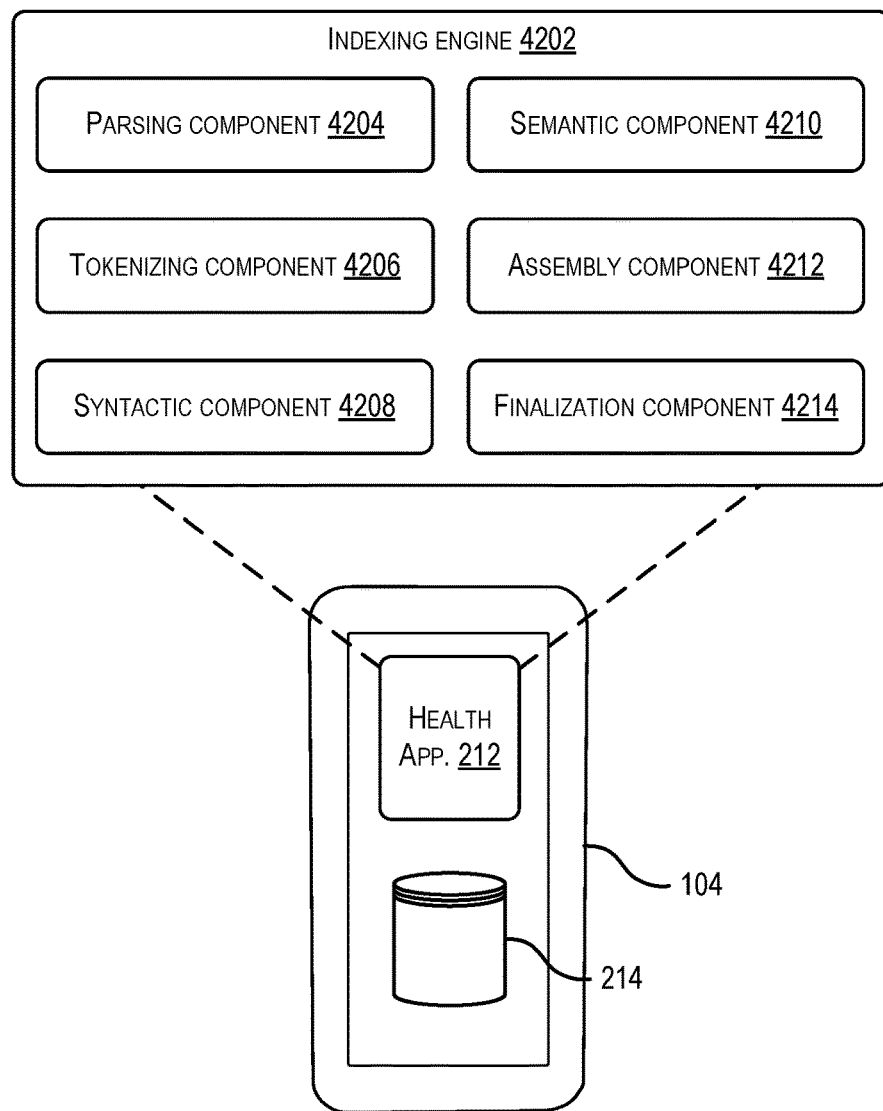
FIG. 42 illustrates a block diagram depicting a user device useable for indexing medical terms from an electronic health record, according to at least one example.
Figure 43:
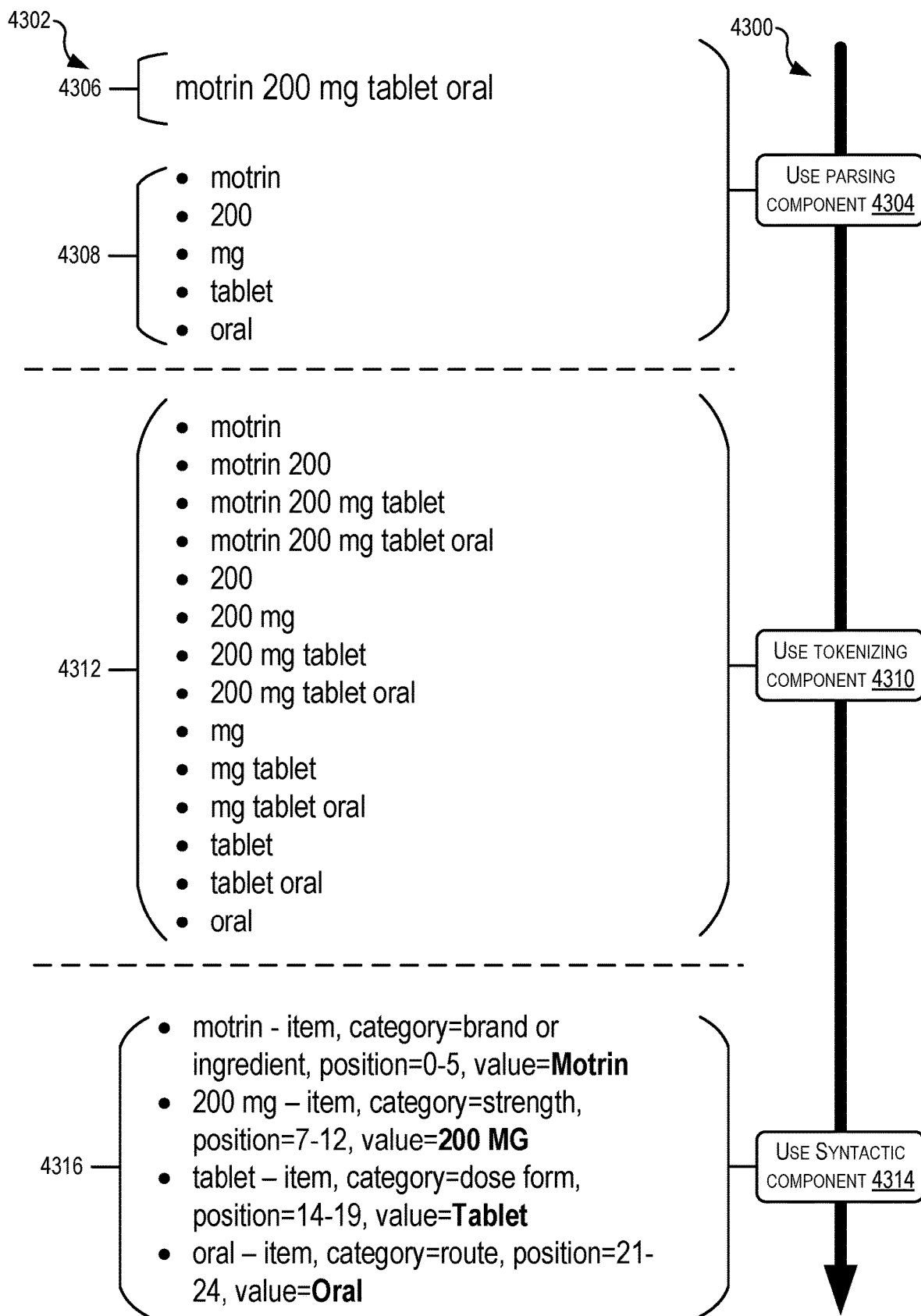
FIG. 43 illustrates a flow chart and associated depictions for indexing medical terms from an electronic health record, according to at least one example.
Figure 44:
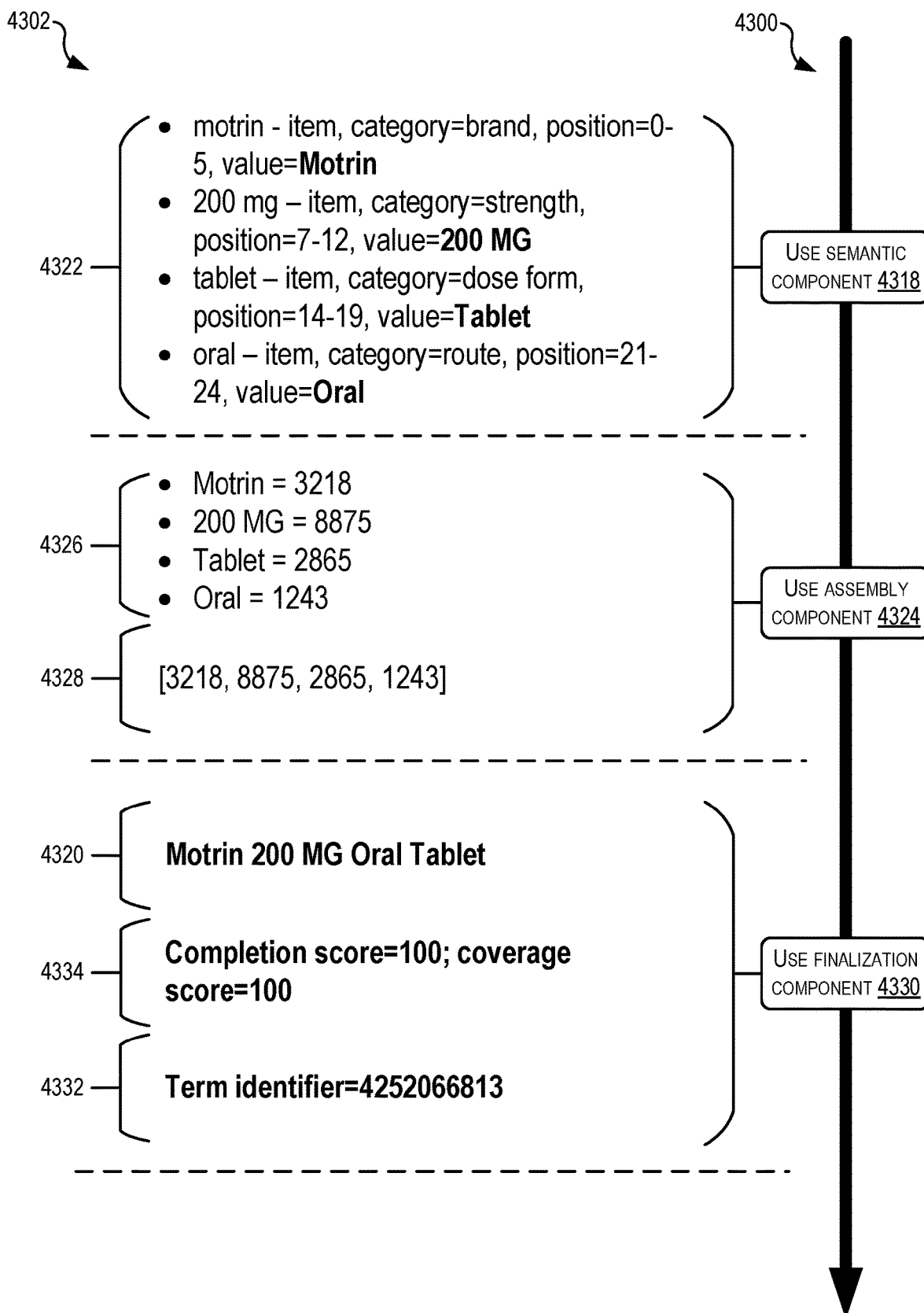
FIG. 44 illustrates a continuation of the flow chart from FIG. 43, according to at least one example.

FIG. 42 illustrates a block diagram 4200 depicting the user device 104 useable for indexing medical terms from an electronic health record, according to at least one example. As introduced herein, the user device 104 may include the health application 212 and the term base 214. The health application 212 may include an indexing engine 4202 that includes a plurality of components 4202-4214. Generally, the indexing engine 4202 may include an indexing algorithm adapted to achieve the function described herein. The function of these components will be discussed with reference to a flow chart and associated depictions in FIGS. 43 and 44. The flow chart in FIGS. 43 and 44 shows the process 4300 relating to indexing medical terms, according to at least one example.

The indexing engine 4202 operates with respect to an information model including a plurality of data types including, for example, medical topics, medical categories, items, and synonyms. In addition, metadata may be associated with medical terms using three different data types including, for example, classifications, facts, and expressions.

A medical topic, sometimes referred to as a medical grammar, may define the data characteristics (e.g., medical categories) that are unique to a particular medical topic. Examples of medical topics include, for example, allergies, conditions, immunizations, labs, medications, procedures, units, vitals, and other similar descriptive medical topics.

A medical category is a classification of a quantifiable value that may be extracted from a term and is associated with one or more categories. Thus, a medical category further defines a medical topic. Examples medical categories for the medical topics of allergies, conditions, immunizations, labs, medications, procedures, units, and vitals are presented below respectively in Tables 1, 2, 3, 4, 5, 6, 7, and 8. Examples of the medical categories are also shown below. For example, "hypersensitivity to" is an example of a medical category of "disposition" in the medical topic of "Allergies" shown in Table 1.

TABLE 1

Medical Topic: Allergies

| Medical Category | Example |
| --- | --- |
| disposition | "hypersensitivity to" |
| substance | "Dog hair" |
| reaction | "hives" |

TABLE 1-continued

Medical Topic: Allergies

| Medical Category | Example |
| --- | --- |
| severity | "mild" |
| ignore | "allergy" |

TABLE 2

Medical Topic: Conditions

| Medical Category | Example |
| --- | --- |
| bodySite | "breast" |
| bodySystemOrRegion | "genitourinal" |
| finding | "Fracture" |
| laterality | "left" |
| position | "top" |
| observable | "Glucose tolerance test" |
| organism | "*Leucocytozoon*" |
| substance | "1,3-beta-glucan synthase" |
| process | "Sting", "Life event" |
| physicalForce | "Gravity" |
| procedure | "Hysterectomy" |
| device | "Pacemaker battery" |
| category | "First degree" |
| findingQualifier | "Unruptured" |
| course | "Chronic" |
| severity | "Severe" |
| occurrence | "Congenital" |
| ignore | "(disorder)", "of", "for" |

TABLE 3

Medical Topic: Immunizations

| Medical Category | Example |
| --- | --- |
| brandName | "Fluvax" |
| vaccine | "Influenza" |
| formulation | "adjuvant", "2015-16" |
| route | "Nasal" |
| ageRange | "adolescent", ">10 years old" |
| ignore | "dialysis" |

TABLE 4

Medical Topic: Labs

| Medical Category | Example |
| --- | --- |
| analyte | "Advil" |
| analyteQualifier | "Ibuprofen" |
| analyteSubQualifier | "150 MG" |
| challenge | "20M post collection" |
| adjustment | "corrected for albumin" |
| property | "Number fraction" |
| timeAspect | "Point in time" |
| specimen | "urine" |
| bodySite | "cervix" |
| valueType | "Quantitative" |
| method | "Agar diffusion" |
| ignore | "Result", "see emr for details" |

TABLE 5

Medical Topic: Medications

| Medical Category | Example |
| --- | --- |
| brandName | "Advil" |
| ingredient | "Ibuprofen" |
| strength | "150 MG" |
| route | "Oral" |
| doseForm | "Tablet" |
| doseFormQualifier | "Extended Release" |
| releasePeriod | "12 HR" |
| ignore | "(bulk)", "(USP)" |

TABLE 6

Medical Topic: Procedures

| Medical Category | Example |
| --- | --- |
| procedure | "EKG" |
| device | "Pacemaker" |
| substance | |

TABLE 7

Medical Topic: Units

| Medical Category | Example |
| --- | --- |
| unit | "mg/ml" |

TABLE 8

Medical Topic: Vitals

| Medical Category | Example |
| --- | --- |
| vital | "Heart rate" |
| ignore | "oral" |

A medical data item may be a quantifiable value that may be extracted from a medical item (e.g., for the brand name category in a medication topic, medical items may include Motrin, Advil, Tylenol, etc.). Thus, medical data items may be grouped by the medical category to which they belong. Medical data items may always be unique to their associated category. In some examples, medical data items may represent the most precise way to describe the quantifiable value it represents, which often is not an abbreviation or synonym. In the event that a symbol associated with a medical data item is valid for multiple medical categories (e.g., Motrin), a unique medical item with the same symbol could exist in all relevant medical categories.

A synonym may be a quantifiable value that is an alternative to its corresponding medical item (e.g., "Mot." may be a synonym to "Motrin"). Synonyms may be associated with a specific medical item, in the event that the symbol (e.g., Mot.) associated with the synonym is valid for multiple medical items and/or medical categories. In some examples, a unique synonym with the same symbol may exist within all relevant medical items and/or medical categories.

In addition to the core ontology from above, metadata may be associated with medical terms using three different data types including, for example, classifications, facts, and expressions. A classification may define a predicate (e.g., classification [pain reliever, anti-inflammatory, cancer drug], color, usage/directions, etc.). A fact may be a Web Ontology Language (OWL) triple and that associates classification, medical term expressions, and a value. An expression specifies a medical term (e.g., Motrin 200 Mg Oral Tablet) as an index (e.g., [100, 101, 102, 2000]. The techniques described herein relate to converting medical terms to expressions and using those expressions to perform various other operations.

In some examples, another data type is used for indexing. For example, a rule describes a context-specific operation to be performed during the indexing process. Rules are often scoped to a medical topic, and sub-scoped to a medical category. In this manner, a rule may be triggered for a specific medical topic and medical category, but not for other topic/category combinations. Using rules may allow the indexing engine 4202 to produce customized results. In some examples, the rules contain both a scope and sub-scope, an evaluation order (in the event that multiple rules are defined for a step/phase), as well as operation-specific parameters.

Generally, the indexing engine 4202 may be configured to implement a process of transforming raw medical terms into quantifiable values (e.g., medical term expressions including expression primitives) that are well suited for storage in a database. These quantifiable values may be queried and/or otherwise manipulated in a manner that produces unique benefits for the users of this technology. The output from the indexing engine 4202 after indexing a raw medical term may include a term index for the medical term and an accompanying data structure that describes in detail each medical category, medical data item, synonyms, etc. that were identified in the raw medical term. The term index is a fingerprint of the medical term referred to as a term expression. The term expression is made up of multiple expression primitives that each map to a medical data item or synonym of a medical data item in the term base. In this manner, the term index represents the raw medical term.

Two raw medical terms that result in the same medical term expression may be considered equivalent even though the structure and content of each of the medical terms is different. For example, indexing the terms "Motrin 200 mg Oral Tablet" and "mot. or. tab. 200 mg" using the indexing engine 4202 will produce the same medical term expressions and are therefore equivalent even though they are visibly different. The more information extracted from the medical term, the longer the medical term expression will be. For example, "Motrin Ibuprofen 200 mg Oral Tablet" will have a longer medical term expression than the example above because Ibuprofen maps to an ingredient (e.g., a medical category) in the medications topic (e.g., a medical topic).

The plurality of components 4202-4214 may include a parsing component 4204, a tokenizing component 4206, a syntactic component 4208, a semantic component 4210, an assembly component 4212, and a finalization component 4214. Generally, the process of indexing medical terms may include pre-processing, in-processing, and post-processing. For example, at any of these stages, rules, as described herein, may be implemented to alter the stage. Because the rules may be applied in the data, they may be applied in an efficient and agile manner. New rule types may be added at any time, without impacting the underlying algorithm that constitutes the plurality of components 4202-4214. For example, when a new pattern is recognized in multiple medical records or something is not displaying correctly, a new rule type may be added at any point in the processes described below to adjust the indexing of the medical terms.

As illustrated in FIG. 43, the process 4300 may begin at 4304 by using the parsing component 4204. This may be performed by the indexing engine 4202. The parsing component 4204 may be configured to extract and parse raw, original medical terms from health record data (e.g., a FHIR data package including an electronic health record). For example, the parsing component 4204 may parse a raw medical term 4306. This parsing subdivides the medical term 4360 into a plurality of individual words, referred to as medical data sections 4308 or more simply sections.

Rules applied at this stage may focus on string manipulation. For example, the rules may adjust the order of the words in the string, ignore certain words, etc. In some examples, the rules may include pre-processing delimiting rules. These rules may set topic-specific delimiters to be used to split the raw medical delimiters. The topic-specific delimiters may be used to split the raw medical term 4306 into the individual medical data sections 4308. In some examples, the rules may include pre-processing replacing rules. These rules may define a regular expression that is used to replace content in the raw medical term 4306 with other content. In some examples, this rule may result in simplified processing downstream since it can be used to normalize otherwise complex character sequences.

At 4310, the process 4300 may include using the tokenizing component 4206. This may be performed by the indexing engine 4202. The tokening component 4206 may be configured to transform the medical data sections 4308 into a plurality of composite medical data sections 4312 or simply composite sections. The plurality of composite medical data sections 4312 include the medical data sections 4308 and possible combinations of multiword sequences of medical data sections 4308 found in the raw medical term 4306.

Rules applied at this stage may focus on manipulation of the composite medical data sections 4312. For example, the rules may adjust multiword sequences, add and/or remove certain words, and cause other changes to the composite medical data sections 4312. In some examples, the rules may include post-processing expanding rules. These rules may be used to identify and add composite medical data sections 4312 that are based on existing composite medical data sections 4312 that have been expanded to include leading and trailing delimiters characters. In some examples, the purpose of this rule may be to accommodate the storage of medical data items in the term base that include this punctuation. In some examples, the rules may include post-processing replacing rules. These rules may be used to identify and add new composite medical data sections 4312 that are based on existing composite medical data sections 4312 that have been transformed to exclude text that matches a certain pattern.

At 4314, the process 4300 may include using the syntactic component 4314. This may be performed by the indexing engine 4202. The syntactic component 4314 may be configured to identify candidate medical data items and synonyms present in the raw medical term 4306 (e.g., Motrin, 200 MG, Tablet, Oral). In table 4316, these medical data items are presented together with other information about the identified sections. For example, the table 4316 may include the raw sections from the raw medical term 4306 (e.g., motrin, 200 mg, tablet, oral), a medical category assigned to each raw section (e.g., brand, ingredient, strength, dose form, route), a position of the raw section in the raw medical term 4306 (e.g., 0-5, 7-12, 14-19, and 21-24). The candidate medical data items and synonyms may be represented as item descriptors.

Rules applied at this stage may focus on inclusion and/or exclusion of additional medical categories and adding, changing, and/or removing item descriptors. In some examples, the rules may include pre-processing rules based on medical categories. These rules may be used to specify additional categories to be used when searching for medical data items and/or synonyms.

At 4318, the process 4300 may include using the semantic component 4210. This may be performed by the indexing engine 4202. The semantic component 4210 may be configured to determine which item descriptors (e.g., items and synonyms) should be included in a uniform medical term 4320 (e.g., Motrin, 200 MG, Tablet, Oral). In this example, the semantic component 4210 identifies the same item descriptors to be included in the uniform medical term 4320 because there were no overlapping words or phrases identified.

The semantic component 4210 may also configured to determine the best combination of item descriptors based on rules. For example, a rule may define what are the necessary elements to fully define a medication (e.g., brand, ingredient, strength, dose form, and route). The rules may indicate when brand names should be replaced by generic names or ingredients, and may indicate any other suitable distinction.

In some examples, the rules may include pre-processing relating to uncategorized medical data sections. These rules may include adding item descriptors that have no corresponding medical category. For example, this may mean that the word/phrase was not in the term base/database. This may affect scoring of the indexed term.

In some examples, the rules may include pre-processing that removes overlaps by category. These rules may function to remove large item descriptors that overlap a smaller expression primitive and for which another alternative, smaller item descriptors, which occupies the same part of the raw term and has the same medical category, exists.

In some examples, the rules may include pre-processing rules that remove overlaps by size. These rules may function to remove overlapping item descriptors from the list of item descriptors extracted from the raw medical terms. An item descriptor may overlap another item descriptor if any part of the text occupies the same location within the medical term expression.

At 4324, the process 4300 may include using the assembly component 4212. This may be performed by the indexing engine 4202. The assembly component 4212 may be configured to generate expression primitives 4326 that correspond to each of the medical data items (e.g., item descriptors) identified previously. For example, the expression primitive for "Motrin" may be "3218", for 200 MG "8875", and so on and so forth. The assembly component 4212 may also be configured to generate a medical term expression 4328 that includes the expression primitives 4326 and corresponds to the uniform medical term 4320. The medical term expression 4328 may function as a parse tree that represents the uniform medical term 4320.

Rules applied at this stage may focus on altering the parse tree. In some examples, the rules may include in-processing rules to exclude categories. The item descriptors may be associated with the medical categories from the medical term expression 4328.

In some examples, the rules may include pre-processing rules to group items. For example, these rules may group item descriptors in the parse tree. For example, grouping may be used to explicitly group ingredient and strength within a medications medical term expression. In some examples, these rules may be used to create parse trees containing multiple, separate medical topics (e.g., notes entered by a doctor or nurse may be indexed, resulting in multiple types of data, including diagnosis and treatment).

In some examples, the rules may include post-processing sorting. These rules may sort the parse tree by medical category. For example, this rule may be used to order the term index so that the more important medical categories are first in the term index.

At 4330, the process 4300 may include using the finalization component 4214. This may be performed by the indexing engine 4202. The finalization component 4214 may be configured to generate additional information from the data contained in the parse tree generated at 4324. In this example, this additional information may include the uniform medical term 4320, a term identifier 4332, and one or more scores. In some examples, the scores 4334 may include a coverage score and a completion score. The coverage score may represent how much of the raw medical term 4306 was indexed. In this example, the coverage score may be 100 because the entire raw medical term 4306 is represented by the medical term expression 4328 and the uniform medical term 4320. The completion score may represent how complete the uniform medical term 4320 is compared to a defined complete score. In this example, the completion score may be 100 because the medical term expression 4328 and the uniform medical term 4320 include the necessary components of a medication.

As described herein, the indexing engine 4202 may be used to quantify/fingerprint raw medical terms extracted from health records downloaded on to user devices. The term index associated with these terms may be stored in the health application 212 and/or the term base 214. In some examples, the term index can be stored in other locations such as a database associated with the health application 212. Information from this database can be accessed by first and third party applications. The indexing engine 4202 may identify and remove personally identifiable information (PII) from raw terms explicitly sent by user devices to a server. In some examples, the indexing engine 4202 may combine the term index with term base metadata. This information can be exposed to APIs to allow digital assistants to convey health care related information to users. In some examples, the indexing engine 4202 can be used in other domains where users ask questions that need to be precisely interpreted in a context-sensitive manner and for which additional fact and/or metadata is often available that will enrich the result of the query.

Figure 45:
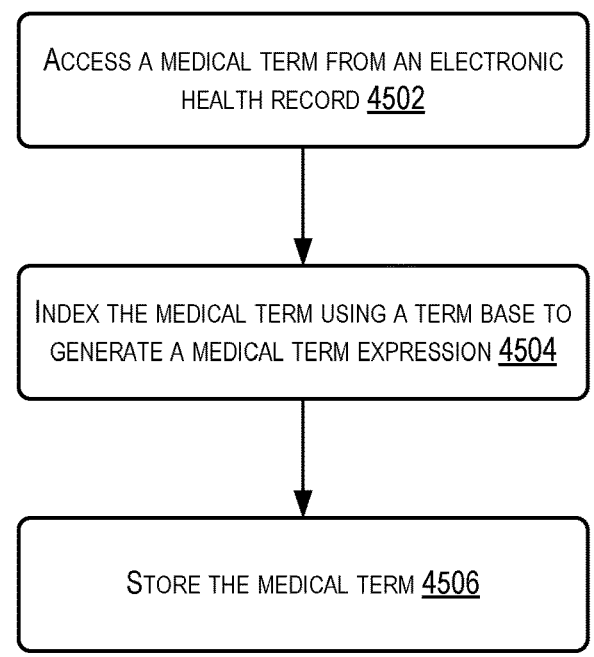
FIG. 45 illustrates an example flow chart showing a process for indexing medical terms from an electronic health record, according to at least one example.

FIG. 45 illustrates an example flow chart showing the process 4500 for indexing medical terms from an electronic health record, according to at least one example. The process 4500 may be performed by the user device 104. In some examples, the provider subscription system 112 may perform the process 4500.

The process 4500 may begin at 4502 by accessing a medical term from an electronic health record. The electronic health record may be stored on a user device.

At 4504, the process 4500 may include indexing the medical term using a term base to generate a medical term expression. In some examples, indexing the medical term may include parsing the medical term to identify one or more medical data sections present in the medical term. Each medical data section may represent a constitute part of the medical term. In some examples, indexing the medical term may include assigning the one or more medical data sections to one or more medical categories of a plurality of medical categories represented in the term base. In some examples, each medical category may include a logical grouping of the medical data sections. In some examples, indexing the medical term may include generating a medical term expression comprising one or more expression primitives based at least in part on information associated with the one or more medical categories. The medical term expression may be useable for generating a uniform medical term corresponding to the medical term.

At 4506, the process 4500 may include storing the medical term expression on the user device. In some examples, the term base may be stored on the user device. In this example, storing the medical term expression on the user device may include storing the medical term expression in the term base.

In some examples, the medical term expression may constitute a term index for accessing the term base.

In some examples, the medical term expression may include a computer-quantifiable expression.

In some examples, the process 4500 may further include determining one or more uniform item descriptors corresponding to the one or more medical data items sections based at least in part on the one or more medical categories. In this example, generating the one or more expression primitives may be based at least in part on the one or more uniform item descriptors.

In some examples, the process 4500 may further include receiving, by the user device and from an endpoint of an electronic health record system, a data package including the electronic health record.

In some examples, the process 4500 may further include a computing completion score representing a completeness of the medical term expression based at least in part on a medical category to which the medical term expression belongs.

In some examples, the process 4500 may further include computing a coverage score representing a ratio of the one or more medical data items sections with respect to the one or more expression primitives. In this example, the process 4500 may further include sending information about the medical term expression to a terminology management system when the coverage score falls below a coverage threshold. The terminology management system may be configured to resolve the term and improve future indexing.

Figure 46:
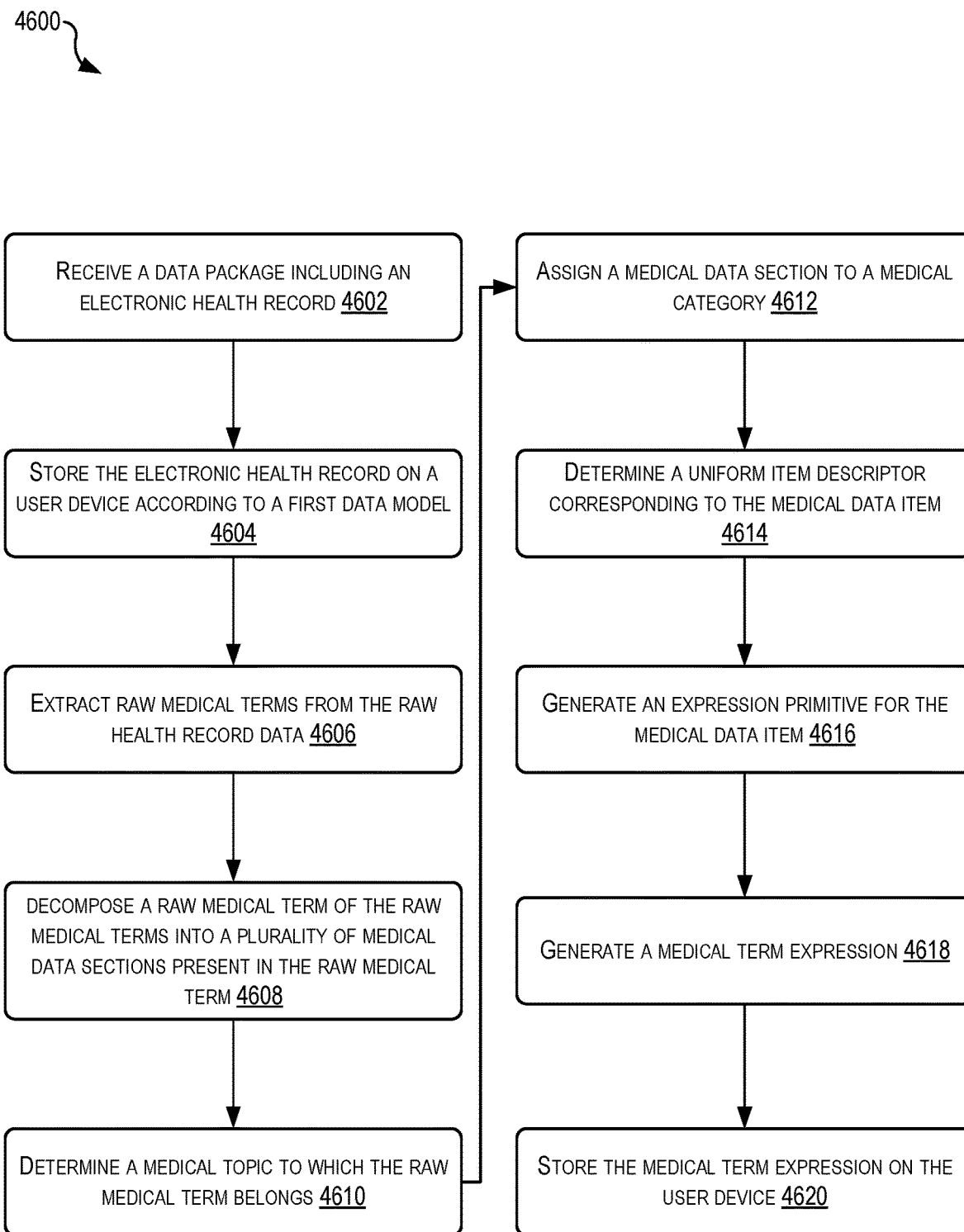
FIG. 46 illustrates an example flow chart showing a process for indexing medical terms from an electronic health record, according to at least one example.

FIG. 46 illustrates an example flow chart showing the process 4600 for indexing medical terms from an electronic health record, according to at least one example. The process 4600 may be performed by the user device 104. In some examples, the provider subscription system 112 may perform the process 4600.

The process 4600 may begin at 4602 by receiving a data package including an electronic health record. The electronic health record may include raw medical data. Receiving may be by a user device and from a gateway of an electronic health record system.

At 4604, the process 4600 may include storing the electronic health record on the user device according to a first data model.

At 4606, the process 4600 may include extracting raw medical terms from the raw health data. In some examples, each raw medical term may include a text string.

At 4608, the process 4600 may include decomposing a raw medical term of the raw medical terms into a plurality of medical data sections present in the raw medical term.

At 4610, the process 4600 may include determining a medical topic to which the raw medical term belongs. In some examples, the medical topic may include a plurality of medical categories.

At 4612, the process 4600 may include, for a medical data section of the plurality of medical data sections, assigning the medical data section to a medical category of plurality of medical categories based at least in part on a comparison of the medical data item with other medical data items represented in the medical category.

At 4614, the process 4600 may include determining a uniform item descriptor corresponding to the medical data item based at least in part on the medical category.

At 4616, the process 4600 may include generating an expression primitive for the medical data item based at least in part on the uniform item descriptor.

At 4618, the process 4600 may include generating a medical term expression. In some examples, this may be based at least in part on the expression primitive. The medical term expression may represent the raw medical term in a quantifiable format and may be formed from the expression primitive and a plurality of other expression primitives.

In some examples, the expression primitive may be a term base identifier representing terms stored in a term base on the user device. The medical term expression may be a medical term index comprising more than one term base identifier.

At 4620, the process 4600 may include storing the medical term expression on the user device according to a second data model. The second data model may distinct from the first data model.

In some examples, the process 4600 may further include generating a data structure that associates constitute parts of the raw medical term with the medical term expression. The data structure may be useable to reproduce the raw medical term from the medical term expression.

In some examples, the process 4600 may further include tokenizing the plurality of medical data sections to create a plurality of composite medical data sections representing sequence groupings of the plurality of medical data sections. In this example, the process 4600 may further include generating the medical term expression based at least in part on the plurality of composite medical data sections.

In some examples, the process 4600 may further include using the medical term expression to generate a uniform medical term corresponding to the raw medical term.

In some examples, the second data model may include a relational graph.

In some examples, the process 4600 may further include identifying a plurality of item descriptors present in the medical category. In this example, each item descriptor may correspond to a section.

In some examples, the plurality of other expression primitives correspond to at least some of the medical data items sections of the plurality of medical data sections.

Figure 47:
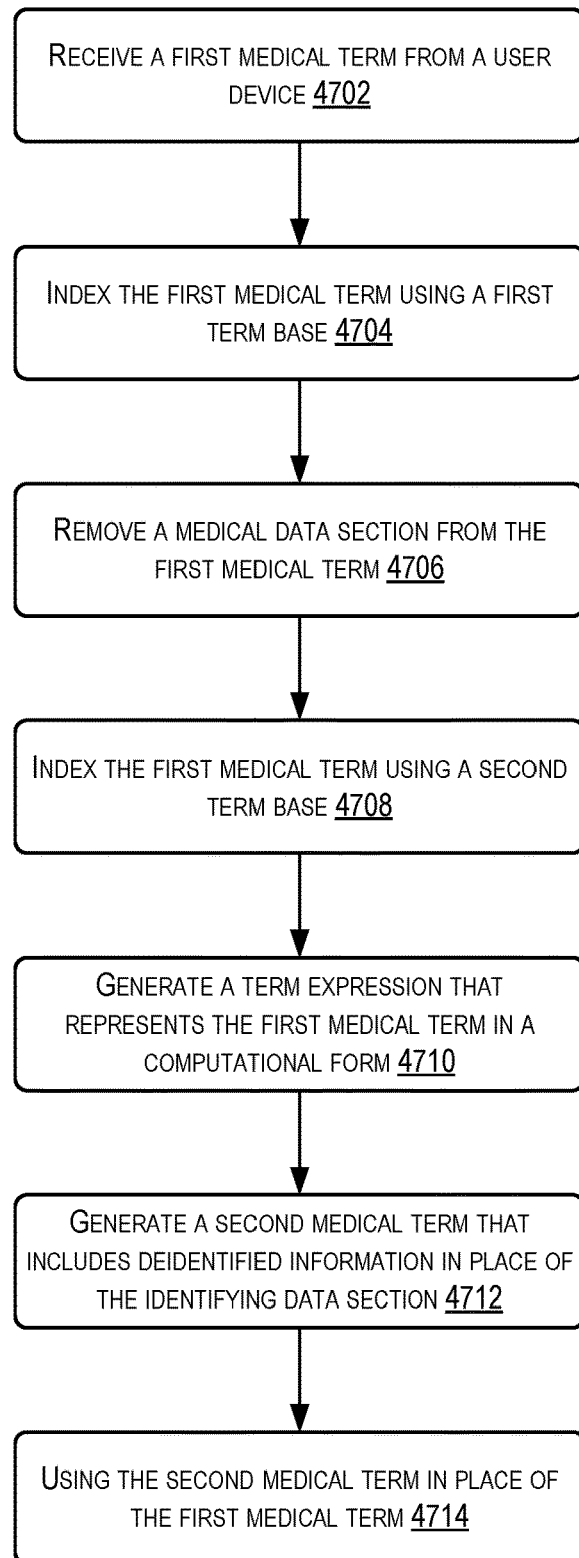
FIG. 47 illustrates an example flow chart showing a process for removing personally identifying information using an indexing engine, according to at least one example.

FIG. 47 illustrates an example flow chart showing the process 4700 for removing personally identifying information using an indexing engine, according to at least one example. The process 4700 may be performed by the provider subscription system 112 or other suitable system. In some examples, the user device 104 may perform the process 4700.

The process 4700 may begin at 4702 by receiving a first medical term from a user device. The first medical term may include personally identifying information that identifies a user (e.g., a user of the user device or other suitable user).

In some examples, receiving the first medical term from the user device may include receiving the first medical term in connection with other medical terms found in an electronic health record stored on the user device and associated with the user.

At 4704, the process 4700 may include indexing the first medical term using a first term base. In some examples, indexing may be performed by at least parsing the first medical term to identify a medical data section present in the first medical term. The medical data section may describe a medical aspect of the first medical term.

At 4706, the process 4700 may include removing the medical data section from the first medical term.

At 4708, the process 4700 may include indexing the first medical term using a second term base. In some examples, this may be performed by at least parsing the first medical term to identify an identifying data section present in the first medical term. The identifying data section may include a portion of the personally identifying information.

At 4710, the process 4700 may include generating a term expression that represents the first medical term in a computational form. The term expression may include a medical term primitive corresponding to the medical data section and an identifying primitive corresponding to the identifying data section.

In some examples, generating the term expression may include assigning the medical data sections and the identifying data section to one or more categories. In this example, generating the term expression may further include generating the medical term primitive and the identifying primitive based at least in part on the one or more categories.

At 4712, the process 4700 may include generating a second medical term that includes deidentified information in place of the identifying data item. This may be performed based at least in part on the term expression.

At 4714, the process 4700 may include using the second medical term in place of the first medical term.

In some examples, the medical term primitive is a first term base identifier corresponding to the first term base. In some examples, the identifying primitive is a second term base identifier corresponding to the second term base. In some examples, the term expression is a term index comprising the first term base identifier and the second term base identifier.

Figure 48:
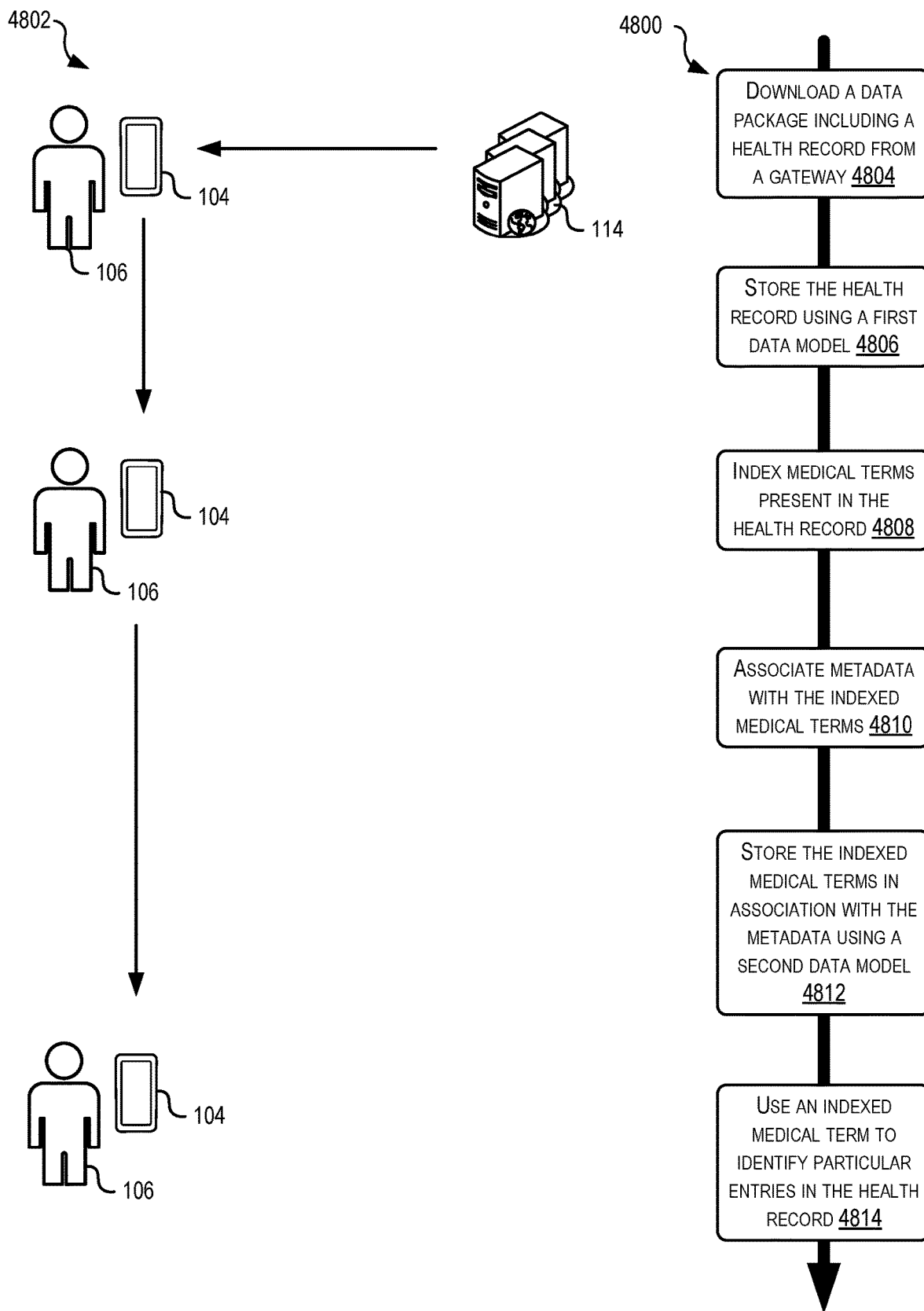
FIG. 48 illustrates a block diagram and a flow chart for enhancing a health record using indexed medical terms, according to at least one example.

FIG. 48 illustrates a block diagram 4802 and a flow chart showing the process 4800 for enhancing a health record using indexed medical terms, according to at least one example. The block diagram 4802 includes the user device 104 and the EHR system 114. The process 4800 may be performed by the user device 104.

The process 4800 may begin at 4804 by downloading a data package including a health record from a gateway. The gateway may be associated with the EHR system 114. In some examples, the health record may be associated with the user 106.

At 4806, the process 4800 may include storing the health record using a first data model. The first data model may be a model configured to store the health record more or less in its raw form. For example, the data package may be downloading using the FHIR standard in XML, JSON, Turtle, or any other suitable format. The first data model may correspond to the FHIR standard data model that relies on four categories of data types: simple/primitive types (e.g., single elements with a primitive value), general purpose complex types (e.g., reusable clusters of elements), complex data types for metadata, and special purpose data types (e.g., reference, narrative, extension, meta, and dosage).

At 4808, the process 4800 may include indexing medical terms present in the health record. This may include generating medical term expressions (e.g., term indexes) for each of the medical terms. Examples of this process are discussed with reference to FIGS. 41-47.

In some examples, an on-device term base is provided in which the medical term expressions are stored. The on-device term based may be prepopulated with a first number of medical concepts. For example, the top one thousand medical concepts may be added to the on-device term base when the user device 104 first ships, as part of an operating system update, or over the air. In this way, the on-device term base is prepopulated with relationships between medical terms. This may be considered a generic or base relational graph. As the medical terms are indexed as described herein, they are added to this base relational graph, which begins to transform the base relational graph into a personalized relational graph that is unique to the user 106. Over time the personalized relational graph is able to not only represent the user's 106 electronic health record, but may do so in a way that provides additional insights into the electronic health record that would be impossible by the user 106 simply viewing her record using a patient portal. For example, as described at 4810, metadata may be added to the record that enhances the base relational graph. Similarly, additional medical concepts can be downloaded, when requested and/or as pushed updates, from a Cloud-based service such as the terminology management service 130 and/or the provider subscription system 112. Storing the personalized relational graph on the user device 104 may be desirable as given that the overall relational graph from the other term base may be much too large to store on the device.

At 4810, the process 4800 may include associating metadata with the indexed medical terms. In some examples, the metadata may be obtained from the provider subscription system 112, the terminology management system 130, or may be local to the user device 104. The metadata may be associated with the indexed medical terms in a manner that enables efficient assembly of user interface elements relating to the indexed medical terms. The type of metadata may depend on the medical topic to which an indexed medical term belongs. For example, if the medical topic were medication, example metadata may include images of medication, general dosage instructions, chemical ingredients, color, links to information about the medication, a link to and/or image of a prescription relating to the medication, and any other suitable information. This metadata may be tagged or otherwise identified as being relevant to the indexed medical terms.

At 4812, the process 4800 may include storing the indexed medical terms in association with the metadata using a second data model. This data may be stored in the term base on the user device 104. In some examples, the indexed medical terms are stored in their indexed form (e.g., as medical term expressions) and the metadata is also stored therewith.

At 4814, the process 4800 may include using an indexed medical term to identify particular entries in the health record. The indexed medical term used at 4814 may correspond to one of the medical terms from the health record. In this example, the indexed medical term may be used to filter, sort, or otherwise organize the health record based on the indexed medical term. For example, a user may select the indexed term "beta blocker" from a list of medication types. This selection may identify all entries in the health record relating to beta blocker by searching for beta blockers in the term base. In particular, this search will be performed by searching medical term expressions in the term base, instead of searching in the raw health record data. The entries may be pulled from instances of the user's 106 electronic health record that were downloaded to the user device 104 from multiple disparate sources (e.g., different gateways of the EHR systems 114).

The indexed medical term used at 4814 may also correspond to a new search term input by the user 106. For example, a user interface may be provided to allow the user 106 to search her electronic health record (e.g., one or more instances of her electronic health record that have been downloaded to the user device 104 from multiple different gateways of the EHR systems 114). Such queries may be indexed using the techniques described herein to generate a search term expression. The search term expression may then be used to easily identify any medical terms expressions that include primitives similar to those in the search term expression. In this manner, such searching is performed in the term base without necessarily having to access the raw version of the electronic health record that is also saved on the user device 104. In some examples, searching the medical term expressions may prove more efficient than conventional searching methods.

Figure 49:
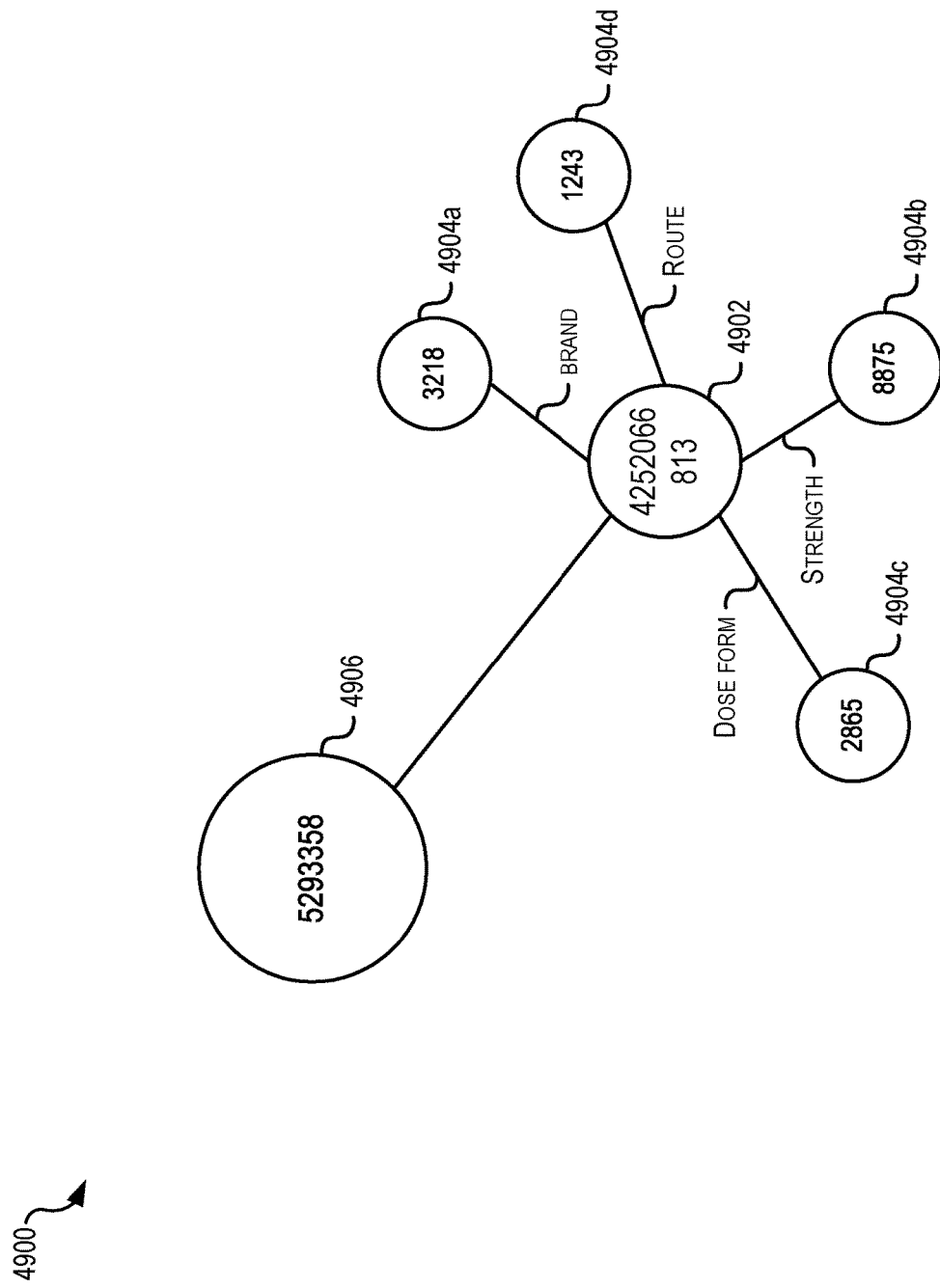
FIG. 49 illustrates an example diagram depicting a relational graph relating to a medical term expression, according to at least one example.

FIG. 49 illustrates an example diagram depicting a relational graph 4900 relating to the medical term expression 4328 from FIG. 44, according to at least one example. The relational graph 4900 may correspond to the medication type medical topic. The relational graph 4900 may include medical term expression primary node 4902. The primary node 4902 may represent the term identifier 4332 that represents the medical term expression 4328. Sub-nodes 4904a-4904d may be associated with the primary node 4902. The sub-nodes 4904a-4904d represent the expression primitives 4326 of the medical term expression 4328. For example, the sub-node 4904a represents the expression primitive 4326 relating to the brand category and which has a value of "Motrin." The sub-node 4904b represents the expression primitive 4326 relating to the strength category and which has a value of "200 MG." The sub-node 4904c represents the expression primitive 4326 relating to the dose form category and which has a value of "tablet." The sub-node 4904d represents the expression primitive 4326 relating to the route category and which has a value of "oral." In some examples, the primary node 4902 is also associated with a class node 4908. The class node 4908 may associate other relational graphs that reference anti-inflammatory medications. The class node 4908 may include a class node identifier that is unique to the class node 4908.

Figure 50:
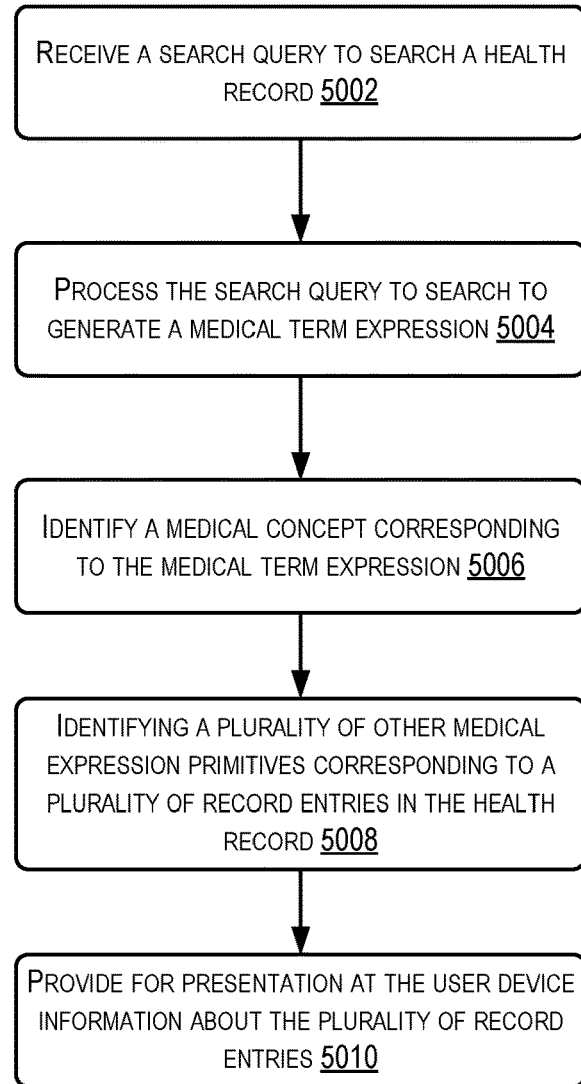
FIG. 50 illustrates an example flow chart showing a process for searching an electronic health record using a medical term expression, according to at least one example.

FIG. 50 illustrates an example flow chart showing the process 5000 for searching an electronic health record using a medical term expression, according to at least one example. The process 5000 may be performed by the user device 104. The provider subscription system 112 may also perform the process 5000.

The process 5000 may begin at 5002 by receiving a search query to search a health record. The health record may be associated with a user account. The search query may include at least one search term. In some examples, at least part of the health record may be stored on a user device (e.g., the user device 104). In some examples, the health record may include a plurality of medical sub-records sourced from one or more gateways of one or more electronic health record systems.

At 5004, the process 5000 may include processing the search query to generate a medical term expression. The medical term expression may be representative of the search query and may include at least one expression primitive corresponding to the at least one search term. In some examples, the medical term expression may be a medical term index usable for accessing a database in which the at least one expression primitive is stored. In some examples, processing the search query to generate the medical term expression may include indexing the at least one search term using an indexing algorithm.

At 5006, the process 5000 may include identifying a medical concept corresponding to the medical term expression. In some examples, identifying the medical concept corresponding to the medical term expression may include identifying the medical concept based at least in part on the at least one expression primitive.

At 5008, the process 5000 may include identifying a plurality of other medical expression primitives corresponding to a plurality of record entries in the health record. In some examples, this may be based at least in part on the at least one expression primitive and the medical concept. The plurality of record entries may be associated with the medical concept. In some examples, identifying the plurality of other medical expression primitives corresponding to the plurality of record entries in the health record may include using the at least one expression primitive as an index to access a database in which information about the health record is stored.

At 5010, the process 5000 may include providing for presentation at the user device information about the plurality of record entries. In some examples, providing for presentation information about the plurality of record entries may include grouping the information about the plurality of record entries under a heading corresponding to the medical concept.

In some examples, the process 5000 may further include using the medical term expression to generate a uniform medical term corresponding to the at least one search term.

In some examples, the process 5000 may further include associating, in a database stored on the user device, metadata with medical term expressions representing the medical terms from the health record. In this example, the metadata may be descriptive of the medical terms represented by the medical term expressions. In this example, the process 5000 may further include generating an index that associates the medical term expressions with reference identifiers of the medical terms from the electronic health record. In this example, the process 5000 may further include receiving a request for information about a particular medical term found in the electronic health record. In this example, the process 5000 may further include, in response to receiving the request, accessing the database using a particular medical term expression associated with the particular medical term and the index to retrieve the information about the particular medical term. The information about the particular medical term may include certain metadata that is descriptive of the particular medical term. In this example, the process 5000 may further include providing the information about the particular medical term for presentation at the user device. The information about the particular medical term may provide contextual information about the particular medical term that was not originally present in the electronic health record.

Figure 51:
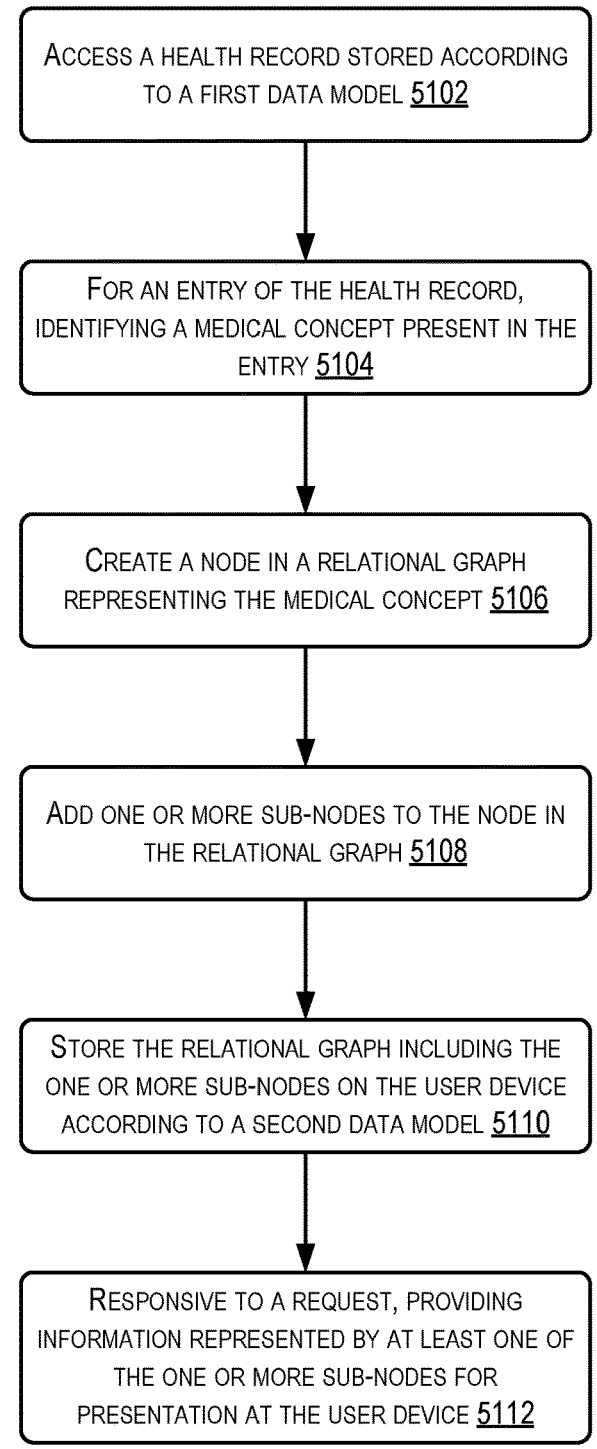
FIG. 51 illustrates an example flow chart showing a process for searching a relational graph representing a medical concept, according to at least one example.

FIG. 51 illustrates an example flow chart showing the process 5100 for searching a relational graph representing a medical concept, according to at least one example. The process 5100 may be performed by the user device 104. The provider subscription system 112 may also perform the process 5100.

The process 5100 may begin at 5102 by accessing a health record stored according to a first data model. The health record may be stored on a user device associated with a user account. The user account may belong to a user of the user device.

At 5104, the process 5100 may include, for an entry of the health record, identifying a medical concept present in the entry. This may be performed based at least in part on a medical term expression generated to represent at least a portion of the entry.

At 5106, the process 5100 may include creating a node in a relational graph representing the medical concept. The relational graph may be unique to the user account. In this manner, each user may include her own personalized relational graph stored on her user device.

At 5108, the process 5100 may include adding one or more sub-nodes to the node in the relational graph. This may be performed based at least in part on additional information relating to the medical concept. In some examples, adding the one or more sub-nodes to the node in the relational graph may include receiving an additional health record, indexing medical terms found in the additional health record to generate medical term expressions, identifying one or more medical concepts based at least in part on the medical term expressions, and for those medical term expressions having the same medical concept as the medical concept, adding additional sub-nodes to the node.

At 5110, the process 5100 may include storing the relational graph including the one or more sub-nodes on the user device according to a second data model.

At 5112, the process 5100 may include responsive to a request, providing information represented by at least one of the one or more sub-nodes for presentation at the user device. In some examples, the request may be at least one of a search request or a filter request. The search request may request searching of the health record. The filter request may request filtering of a portion of the health record.

In some examples, the process 5100 may further include adding additional sub-nodes to the node based at least in part on detecting updates to a global term base. The global term base may be stored by a server computer.

In some examples, the process 5100 may further include adding additional sub-nodes to the node based at least in part on identifying, in a remote database, metadata associated with the medical concept.

Figure 52:
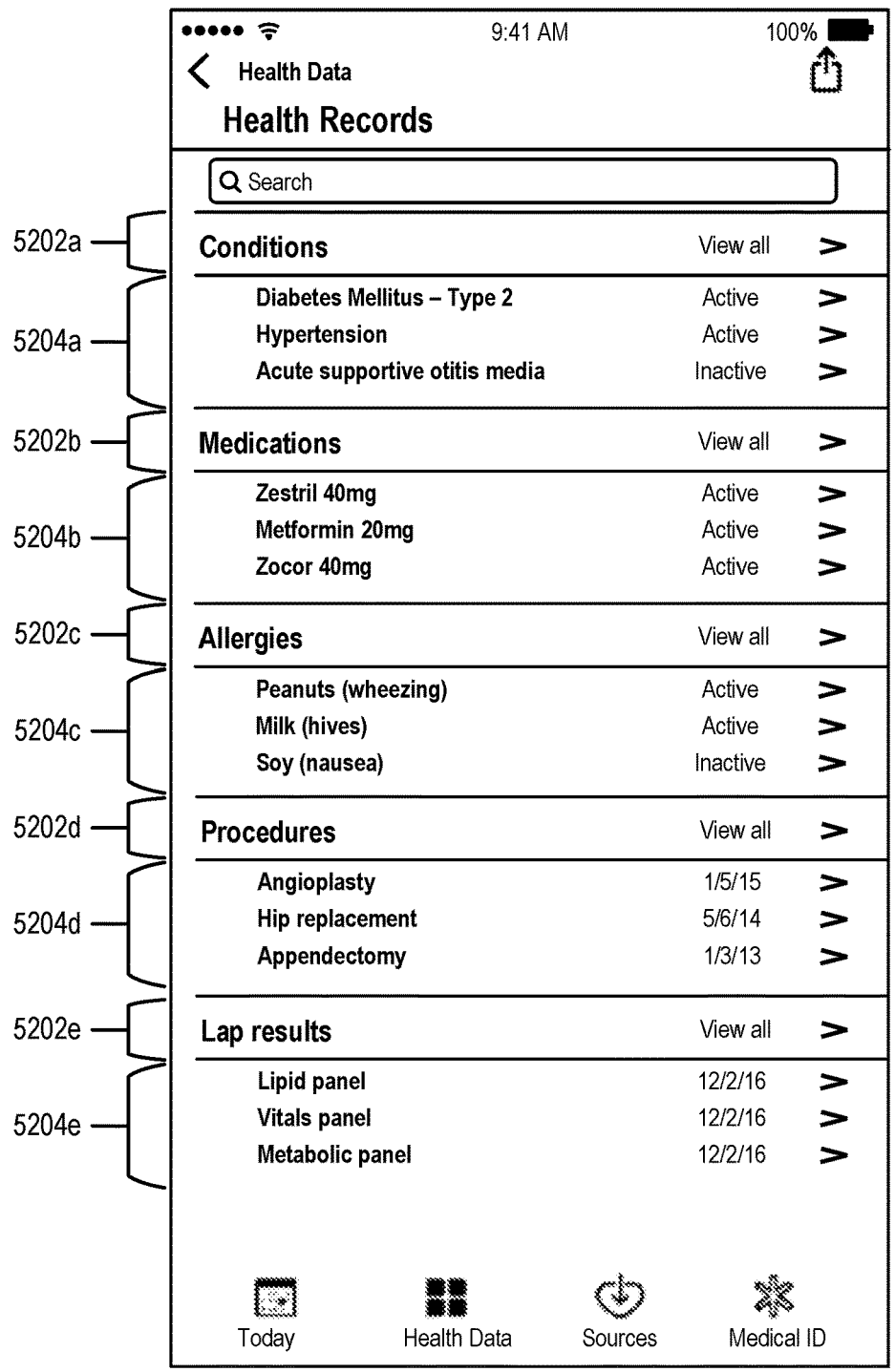
FIG. 52 illustrates an example user interface view illustrating a portion of an electronic health record organized according to medical concepts, according to at least one example.

FIG. 52 illustrates an example user interface (UI) view 5200 illustrating a portion of an electronic health record organized according to medical concepts, according to at least one example. The UI view 5200, which may be presented on the user device 104, is an example of UI views (1)-(25). In particular the UI view 5200 may be presented after the user has downloaded at least one electronic health record to her device (e.g., one connection with an EHR gateway has been established).

The UI view 5200 includes a plurality of medical concepts 5202a-5202e according to which is organized a plurality of medical records entries 5204a-5204e. The medical concepts 5202 may be fixed, as described herein. The medical record entries 5204, which represent medical terms, may be associated with the medical concepts 5202 as part of the indexing process described herein. In particular, these associations between medical terms from the user's electronic health record and the medical concepts may be stored in the user's personalized relational graph in the on-device term base.

The medical record entries 5204 may be sourced from one or more electronic health records, but may be presented in the same UI view 5200. By default, the medical record entries 5204 may be sorted based on any suitable factor. For example, the medical record entries 5204*a* may be sorted based on whether the condition is "active" or "inactive." Similarly, the medical record entries 5204*d* may be sorted based on date of procedure.

Selection of the "view all>" UI element on any of the medical concepts 5202 may reveal other medical record entries 5204 associated with the relevant medical concept 5202. For example, selection of the "view all" UI element associated with the medical concept 5202*a* (conditions), may reveal additional medical record entries 5204*a* in addition to the three listed. In some examples, this may provide a more complete picture of the user's health record.

Selection of the ">" UI element following one of the labels (e.g., active, inactive, date, etc.) may reveal additional information about the particular medical record entry 5204. For example, selection of the medical record entry 5204*b* for "Zestril" may reveal additional information about this prescription. A first portion of the additional information may have been sourced from the medical record (e.g., a prescribing doctor, a pharmacy where it was filled, etc.). A second portion of the additional information may have been added using the techniques described herein. For example, the additional information may include metadata downloaded from the off-device term base that is associated with the prescription Zestril (e.g., images of the pill, ingredients, etc.).

In some examples, the techniques described herein, may be used to associate medical record entries 5204 across different medical categories 5202. For example, assume that a first medical term identifies the medical record entry 5204*a* for hypertension and a second medical term identifies the medical record entry 5204*b* for Zestril. The relational graph on the device may include an association between a condition of hypertension and a prescription for Zestril. This may be because Zestril is prescribed to treat hypertension. If the medical record from which the condition and prescription were obtained did not already include this association, the techniques described herein may add this association and present information about it. For example, continuing with the example above, selection of "Zestril" may reveal that additional information that indicates that it is being used to treat the condition of hypertension.

Figure 53:
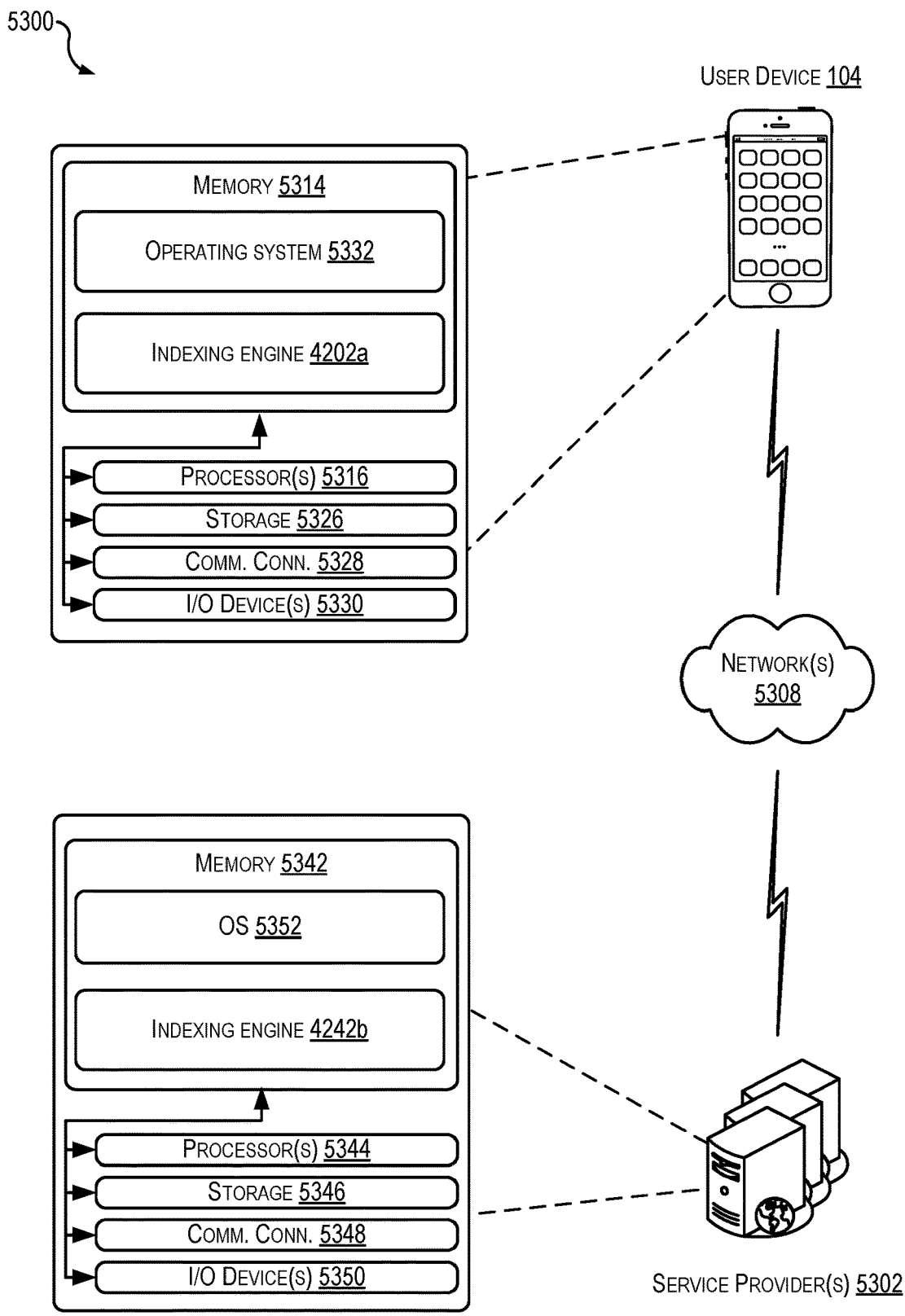
FIG. 53 illustrates a simplified block diagram depicting an example architecture for implementing the techniques described herein, according to at least one example.

FIG. 53 illustrates an example architecture or environment 5300 configured to implement techniques described herein, according to at least one example. In some examples, the example architecture 5300 may further be configured to enable the user device 104, service provider computers 5302 to share information. The service provider computers 5302 are examples of the business subscription system 206, the provider subscription system 112, the EHR systems 114, and the terminology management system 130. In some examples, the devices may be connected via one or more networks 5308 (e.g., via Bluetooth, WiFi, the Internet, or the like). In some examples, the service provider computers 5302 may be configured to implement at least some of the techniques described herein with reference to the user device 104.

In some examples, the networks 5308 may include any one or a combination of many different types of networks, such as cable networks, the Internet, wireless networks, cellular networks, satellite networks, other private and/or public networks, or any combination thereof. While the illustrated example represents the user device 104 accessing the service provider computers 5302 via the networks 5308, the described techniques may equally apply in instances where the user device 104 interacts with the service provider computers 5302 over a landline phone, via a kiosk, or in any other manner. It is also noted that the described techniques may apply in other client/server arrangements (e.g., set-top boxes, etc.), as well as in non-client/server arrangements (e.g., locally stored applications, peer to peer configurations, etc.).

As noted above, the user device 104 may be any type of computing device such as, but not limited to, a mobile phone, a smartphone, a personal digital assistant (PDA), a laptop computer, a desktop computer, a thin-client device, a tablet computer, a wearable device, or the like. In some examples, the user device 104 may be in communication with the service provider computers 5302 via the network 5308, or via other network connections.

In one illustrative configuration, the user device 104 may include at least one memory 5314 and one or more processing units (or processor(s)) 5316. The processor(s) 5316 may be implemented as appropriate in hardware, computer-executable instructions, firmware, or combinations thereof. Computer-executable instruction or firmware implementations of the processor(s) 5316 may include computer-executable or machine-executable instructions written in any suitable programming language to perform the various functions described. The user device 104 may also include geo-location devices (e.g., a global positioning system (GPS) device or the like) for providing and/or recording geographic location information associated with the user device 104.

The memory 5314 may store program instructions that are loadable and executable on the processor(s) 5316, as well as data generated during the execution of these programs. Depending on the configuration and type of the user device 104, the memory 5314 may be volatile (such as random access memory (RAM)) and/or non-volatile (such as read-only memory (ROM), flash memory, etc.). The user device 104 may also include additional removable storage and/or non-removable storage 5326 including, but not limited to, magnetic storage, optical disks, and/or tape storage. The disk drives and their associated non-transitory computer-readable media may provide non-volatile storage of computer-readable instructions, data structures, program modules, and other data for the computing devices. In some implementations, the memory 5314 may include multiple different types of memory, such as static random access memory (SRAM), dynamic random access memory (DRAM), or ROM. While the volatile memory described herein may be referred to as RAM, any volatile memory that would not maintain data stored therein once unplugged from a host and/or power would be appropriate.

The memory 5314 and the additional storage 5326, both removable and non-removable, are all examples of non-transitory computer-readable storage media. For example, non-transitory computer readable storage media may include volatile or non-volatile, removable or non-removable media implemented in any method or technology for storage of information such as computer-readable instructions, data structures, program modules, or other data. The memory 5314 and the additional storage 5326 are both examples of non-transitory computer storage media. Additional types of computer storage media that may be present in the user device 104 may include, but are not limited to, phase-change RAM (PRAM), SRAM, DRAM, RAM, ROM, Electrically Erasable Programmable Read-Only Memory (EEPROM), flash memory or other memory technology, compact disc read-only memory (CD-ROM), digital video disc (DVD) or other optical storage, magnetic cassettes, magnetic tape, magnetic disk storage or other magnetic storage devices, or any other medium that can be used to store the desired information and that can be accessed by the user device 104. Combinations of any of the above should also be included within the scope of non-transitory computer-readable storage media. Alternatively, computer-readable communication media may include computer-readable instructions, program modules, or other data transmitted within a data signal, such as a carrier wave, or other transmission. However, as used herein, computer-readable storage media does not include computer-readable communication media.

The user device 104 may also contain communications connection(s) 5328 that allow the user device 104 to communicate with a data store, another computing device or server, user terminals, and/or other devices via the network 5308. The user device 104 may also include I/O device(s) 5330, such as a keyboard, a mouse, a pen, a voice input device, a touch input device, a display, speakers, a printer, etc.

Turning to the contents of the memory 5314 in more detail, the memory 5314 may include an operating system 5332 and/or one or more application programs or services for implementing the features disclosed herein including the indexing engine 4202. The service provider computer 5302 may also include a memory 5342 that includes an indexing engine 4202*b*. In this manner, the techniques described herein may be implemented by any one, or a combination of more than one, of the computing devices (e.g., the user device 104 or the service provider computer 5302).

The service provider computers 5302 may also be any type of computing device such as, but not limited to, a mobile phone, a smartphone, a PDA, a laptop computer, a desktop computer, a thin-client device, a tablet computer, a wearable device, a server computer, a virtual machine instance, etc. In some examples, the service provider computers 5302 may be in communication with the user device 104 via the network 5308, or via other network connections.

In one illustrative configuration, the service provider computers 5302 may include at least one memory 5342 and one or more processing units (or processor(s)) 5344. The processor(s) 5344 may be implemented as appropriate in hardware, computer-executable instructions, firmware, or combinations thereof. Computer-executable instruction or firmware implementations of the processor(s) 5344 may include computer-executable or machine-executable instructions written in any suitable programming language to perform the various functions described.

The memory 5342 may store program instructions that are loadable and executable on the processor(s) 5344, as well as data generated during the execution of these programs. Depending on the configuration and type of service provider computer 5302, the memory 5342 may be volatile (such as RAM) and/or non-volatile (such as ROM, flash memory, etc.). The service provider computer 5302 may also include additional removable storage and/or non-removable storage 5346 including, but not limited to, magnetic storage, optical disks, and/or tape storage. The disk drives and their associated non-transitory computer-readable media may provide non-volatile storage of computer-readable instructions, data structures, program modules, and other data for the computing devices. In some implementations, the memory 5342 may include multiple different types of memory, such as SRAM, DRAM, or ROM. While the volatile memory described herein may be referred to as RAM, any volatile memory that would not maintain data stored therein once unplugged from a host and/or power would be appropriate. The memory 5342 and the additional storage 5346, both removable and non-removable, are both additional examples of non-transitory computer-readable storage media.

The service provider computer 5302 may also contain communications connection(s) 5348 that allow the service provider computer 5302 to communicate with a data store, another computing device or server, user terminals and/or other devices via the network 5308. The service provider computer 5302 may also include I/O device(s) 5350, such as a keyboard, a mouse, a pen, a voice input device, a touch input device, a display, speakers, a printer, etc.

Turning to the contents of the memory 5342 in more detail, the memory 5342 may include an operating system 5352 and/or one or more application programs or services for implementing the features disclosed herein including the indexing engine 4224*b*.

The various examples further can be implemented in a wide variety of operating environments, which in some cases can include one or more user computers, computing devices or processing devices which can be used to operate any of a number of applications. User or client devices can include any of a number of general purpose personal computers, such as desktop or laptop computers running a standard operating system, as well as cellular, wireless and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems, and other devices capable of communicating via a network.

Most examples utilize at least one network that would be familiar to those skilled in the art for supporting communications using any of a variety of commercially-available protocols, such as TCP/IP, OSI, FTP, UPnP, NFS, CIFS, and AppleTalk. The network can be, for example, a local area network, a wide-area network, a virtual private network, the Internet, an intranet, an extranet, a public switched telephone network, an infrared network, a wireless network, and any combination thereof.

In examples utilizing a network server, the network server can run any of a variety of server or mid-tier applications, including HTTP servers, FTP servers, CGI servers, data servers, Java servers, and business application servers. The server(s) may also be capable of executing programs or scripts in response to requests from user devices, such as by executing one or more applications that may be implemented as one or more scripts or programs written in any programming language, such as Java®, C, C# or C++, or any scripting language, such as Perl, Python or TCL, as well as combinations thereof. The server(s) may also include database servers, including without limitation those commercially available from Oracle®, Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of examples, the information may reside in a storage-area network (SAN) familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as RAM or ROM, as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a non-transitory computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or browser. It should be appreciated that alternate examples may have numerous variations from that described above. For example, customized hardware might also be used and/or particular elements might be implemented in hardware, software (including portable software, such as applets) or both. Further, connection to other computing devices such as network input/output devices may be employed.

Non-transitory storage media and computer-readable media for containing code, or portions of code, can include any appropriate media known or used in the art, including storage media, such as, but not limited to, volatile and non-volatile, removable and non-removable media implemented in any method or technology for storage of information such as computer-readable instructions, data structures, program modules, or other data, including RAM, ROM, EEPROM, flash memory or other memory technology, CD-ROM, DVD or other optical storage, magnetic cassettes, magnetic tape, magnetic disk storage or other magnetic storage devices, or any other medium which can be used to store the desired information and which can be accessed by a system device. Based at least in part on the disclosure and teachings provided herein, a person of ordinary skill in the art will appreciate other ways and/or methods to implement the various examples.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated examples thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a" and "an" and "the" and similar referents in the context of describing the disclosed examples (especially in the context of the following claims) are to be construed to cover both the singular and the plural, unless otherwise indicated herein or clearly contradicted by context. The terms "comprising," "having," "including," and "containing" are to be construed as open-ended terms (e.g., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate examples of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is otherwise understood within the context as used in general to present that an item, term, etc., may be either X, Y, or Z, or any combination thereof (e.g., X, Y, and/or Z). Thus, such disjunctive language is not generally intended to, and should not, imply that certain examples require at least one of X, at least one of Y, or at least one of Z to each be present.

Preferred examples of this disclosure are described herein, including the best mode known to the inventors for carrying out the disclosure. Variations of those preferred examples may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

As described above, one aspect of the present technology is the gathering and use of data available from various sources to provide a comprehensive and complete window to a user's personal health record. The present disclosure contemplates that in some instances, this gathered data may include personal information data that uniquely identifies or can be used to contact or locate a specific person. Such personal information data can include demographic data, location-based data, telephone numbers, email addresses, twitter ID's, home addresses, data or records relating to a user's health or level of fitness (e.g., vital signs measurements, medication information, exercise information), date of birth, or any other identifying or personal or health information.

The present disclosure recognizes that the use of such personal information data, in the present technology, can be used to the benefit of users. For example, the personal information data can be used to provide enhancements to a user's personal health record. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services or other services relating to health record management, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data.

What is claimed is:

1. A user device, comprising: a memory configured to store computer-executable instructions; and a processor in communication with the memory and configured to execute the computer-executable instructions to at least:
    send an information request to a server, the information request requesting information about accessing a gateway of an electronic health record system, wherein the server is implemented by a first computer system that is configured to maintain configuration information of a plurality of electronic health record systems including the electronic health record system, wherein the electronic health record system is implemented by a second computer system that is logically and physically isolated from the first computer system, wherein the second computer system is configured to maintain electronic health records for a population of users including a user associated with the user device;
    receive, from the server, in response to the information request, a communication comprising an update value and a data object associated with the gateway, the update value representing a time period and being generated based at least in part on characteristics of the electronic health record system, and the data object comprising particular configuration information useable by the user device for accessing the gateway;
    determine a random clock value that is between zero and the update value, the random clock value corresponding to a clock time within the time period; and
    send an access request to the gateway at the clock time based at least in part on the particular configuration information, the access request to request downloading of medical record data maintained by the electronic health record system.

2. The user device of claim 1, wherein the particular configuration information comprises application programming interface (API) information that is particular to the gateway.

3. The user device of claim 1, wherein the memory is configured to store additional computer-executable instructions and the processor is further configured to execute the additional computer-executable instructions to at least:
    send an additional information request to the server in preparation for sending an additional access request to the gateway;
    receive an additional communication from the server, the additional communication comprising a status indicator for the gateway; and
    refrain from sending the additional access request when the status indicator indicates that the gateway is unavailable.

4. The user device of claim 1, wherein the medical record data is downloaded according to Fast Healthcare Interoperability Resources (FHIR) standard.

5. The user device of claim 1, wherein the data object further comprises a universal user identifier for the gateway.

6. A computer-implemented method, comprising:
sending, by a user device, an information request to a first server operated by a first entity, the information request requesting information about accessing a gateway of an electronic health record system operated by a second entity and implemented using a second server that is logically and physically isolated from the second server, wherein the first server is configured to maintain configuration information of a plurality of electronic health record systems including the electronic health record system, and wherein the second server is configured to maintain electronic health records for a population of users including a user associated with the user device;
receiving, from the first server, in response to the information request, a communication comprising a data object associated with the gateway, the data object comprising particular configuration information useable by the user device for accessing the gateway;
sending, by the user device, a first access request to the gateway based at least in part on the particular configuration information, the first access request to request downloading of medical record data maintained by the electronic health record system; and
when the first access request fails,
determining a future time to send a second access request to the gateway;
sending, by the user device and at the future time, the second access request to the gateway; and
receiving a data package from the gateway based at least in part on the second access request, the data package comprising medical record data.

7. The computer-implemented method of claim 6, wherein the particular configuration information comprises application programming interface (API) information that is particular to the gateway.

8. The computer-implemented method of claim 6, wherein determining the future time is based at least in part on characteristics of the user device.

9. The computer-implemented method of claim 8, wherein the characteristics of the user device comprise at least one of locked state, battery life, network connectivity, available processing capabilities, or available storage.

10. The computer-implemented method of claim 6, wherein determining the future time is based at least in part on a predefined routine defined in the user device, the predefined routine useable by the user device for contacting remote resources.

11. The computer-implemented method of claim 6, wherein the information request includes information identifying a medical provider associated with the electronic health record system and a plurality of other providers associated with at least one of the electronic health record system or a different electronic health record system.

12. The computer-implemented method of claim 6, further comprising:
sending an additional information request to the first server in preparation for sending an additional access request to the gateway;
receiving an additional communication from the first server, the additional communication comprising a status indicator for the gateway; and
refraining from sending the additional access request when the status indicator indicates that the gateway is unavailable.

13. The user device of claim 1, wherein the memory is configured to store additional computer-executable instructions and the processor is further configured to execute the additional computer-executable instructions to at least:
after sending the access request, receive a data package comprising the medical record data maintained according to a first format; and
store the medical record data on the user device according to the first format.

14. The user device of claim 13, wherein the memory is configured to store additional computer-executable instructions and the processor is further configured to execute the additional computer-executable instructions to at least:
after receiving the data package, convert at least a portion of the medical record data from the first format to a second format that comprises a set of predefined data categories; and
store the portion of the medical record data on the user device according to the second format and using the set of predefined data categories.

15. The user device of claim 1, wherein sending the information request comprises sending the information request responsive to a user input of the user received associated with the user device.

16. The user device of claim 1, wherein the information request requests connection information relating to a time window for the user device to (i) connect to the gateway of the electronic health record system, and (ii) download the medical record data.

17. The user device of claim 16, wherein the time period defines the time window, and the clock time defines the time at which the user device sends the access request.

18. The computer-implemented method of claim 6, further comprising establishing a persistent data connection with the gateway for periodically downloading other medical record data maintained by the electronic health record system.

19. The computer-implemented method of claim 6, further comprising, after receiving the data package from the gateway, periodically sending additional data access requests to the gateway to request downloading of other medical record data maintained by the electronic health record system and that are associated with the user.

* * * * *